(12) United States Patent
Ling et al.

(10) Patent No.: US 10,006,049 B2
(45) Date of Patent: Jun. 26, 2018

(54) HAIRPIN MRNA ELEMENTS AND METHODS FOR THE REGULATION OF PROTEIN TRANSLATION

(71) Applicant: University of Florida Research Foundation, Incorporated, Gainesville, FL (US)

(72) Inventors: Chen Ling, Gainesville, FL (US); Arun Srivastava, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days. days.

(21) Appl. No.: 14/890,705

(22) PCT Filed: May 16, 2014

(86) PCT No.: PCT/US2014/038460
§ 371 (c)(1),
(2) Date: Nov. 12, 2015

(87) PCT Pub. No.: WO2014/186746
PCT Pub. Date: Nov. 20, 2014

(65) Prior Publication Data
US 2016/0102321 A1 Apr. 14, 2016

Related U.S. Application Data

(60) Provisional application No. 61/824,319, filed on May 16, 2013.

(51) Int. Cl.
*C12N 15/86* (2006.01)
*A61K 35/76* (2015.01)
*C12N 7/00* (2006.01)

(52) U.S. Cl.
CPC .............. *C12N 15/86* (2013.01); *A61K 35/76* (2013.01); *C12N 7/00* (2013.01); *C12N 2750/14022* (2013.01); *C12N 2750/14143* (2013.01); *C12N 2830/50* (2013.01); *C12N 2840/105* (2013.01)

(58) Field of Classification Search
None
See application file for complete search history.

(56) References Cited

U.S. PATENT DOCUMENTS

| | | | | |
|---|---|---|---|---|
| 5,932,210 A | * | 8/1999 | Gregory | C07K 14/4746 424/93.2 |
| 6,106,824 A | | 8/2000 | Kaplitt et al. | |
| 2012/0232133 A1 | * | 9/2012 | Balazs | C07K 16/1045 514/44 R |

FOREIGN PATENT DOCUMENTS

| | | | | |
|---|---|---|---|---|
| WO | WO 2012/115980 A1 | | 8/2012 | |
| WO | WO 2012115980 A1 | * | 8/2012 | C07K 16/1045 |

OTHER PUBLICATIONS

International Search Report and Written Opinion for International Application No. PCT/US2014/038460 dated Oct. 20, 2014.
International Preliminary Report on Patentability for International Application No. PCT/US2014/038460 dated Nov. 26, 2015.
Alex et al., DNA-binding activity of adeno-associated virus Rep is required for inverted terminal repeat-dependent complex formation with herpes simplex virus ICP8. J Virol. Mar. 2012;86(5):2859-63. doi: 10.1128/JVI.06364-11. Epub Dec. 28, 2011.
Arruda et al., Lack of germline transmission of vector sequences following systemic administration of recombinant AAV-2 vector in males. Mol Ther. Dec. 2001;4(6):586-92.
Kahvejian, Mammalian poly(A)-binding protein is a eukaryotic translation initiation factor, which acts via multiple mechanisms. Genes Dev. Jan. 1, 2005;19(1):104-13.
Zhang et al., to polyadenylate or to deadenylate: that is the question. Cell Cycle. Nov. 15, 2010;9(22):4437-49. Epub Nov. 15, 2010.

* cited by examiner

*Primary Examiner* — Antonio Galisteo Gonzalez
(74) *Attorney, Agent, or Firm* — Wolf, Greenfield & Sacks, P.C.

(57) ABSTRACT

The present invention provides novel mRNA elements capable of forming hairpin, double-stranded RNA structures independent of other non-coding RNAs. These mRNAs are stably expressed, lack polyadenylation tails, and allow minimal protein translation except when in the presence of specific proteins. Also provided, are compositions and kits comprising the mRNA element, as well as methods for its use in the regulation of protein translation. Advantageously, the disclosed elements represent a novel tool useful in regulating the expression of a wide variety of proteins of interest.

23 Claims, 33 Drawing Sheets

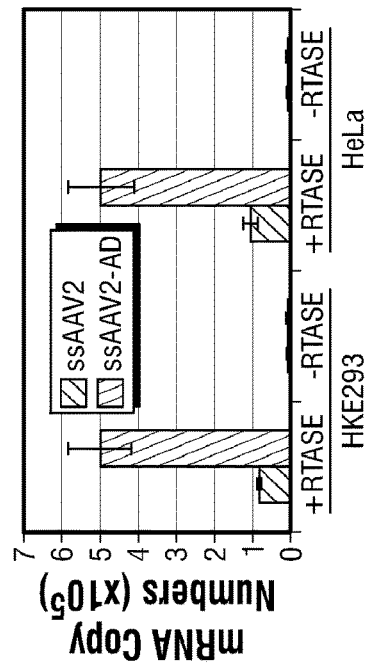
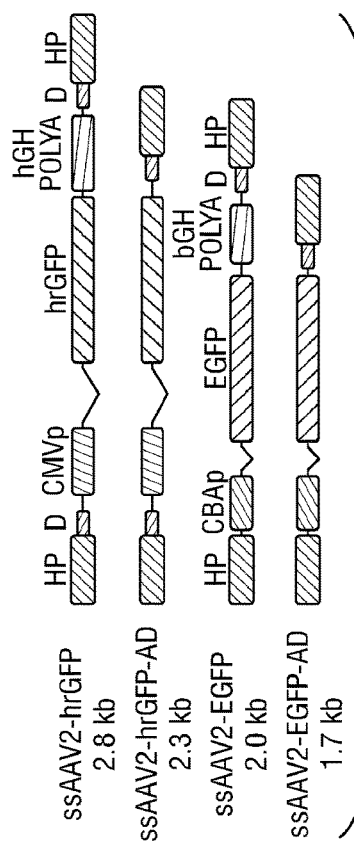
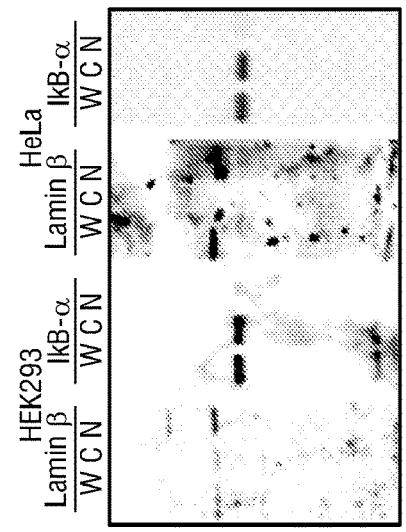
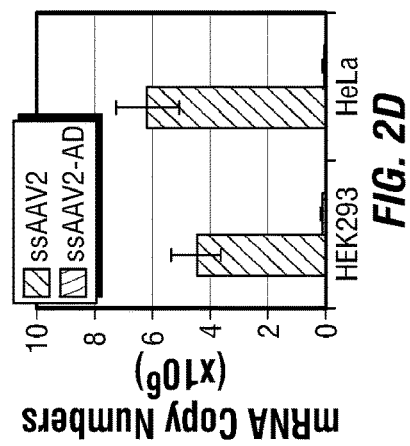
FIG. 2A
FIG. 2B
FIG. 2C
FIG. 2D
FIG. 2E

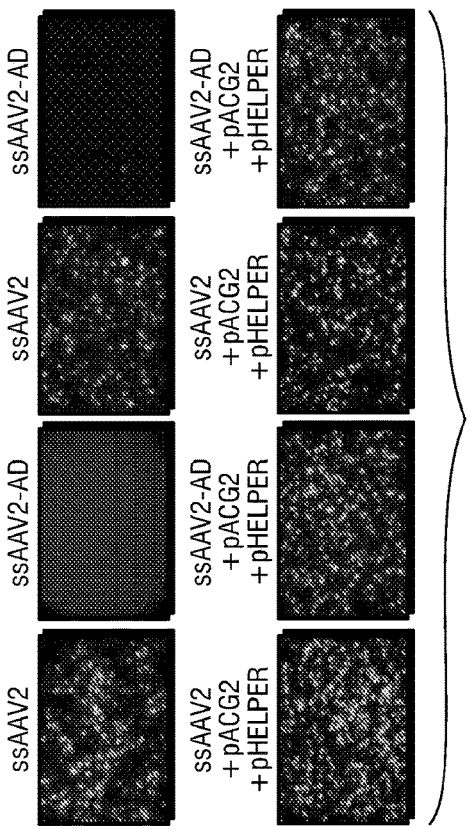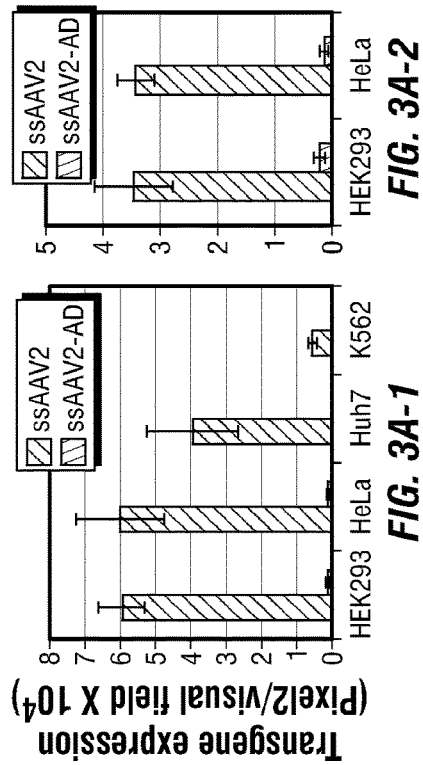
FIG. 3A-1  FIG. 3A-2  FIG. 3B  FIG. 3C  FIG. 3D

HEK293

HeLa

K562

Huh7

HEK293

HeLa

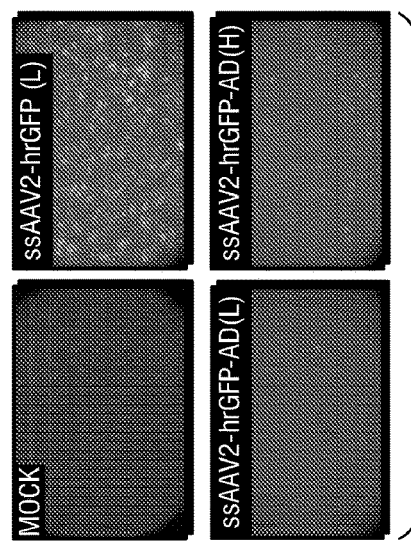
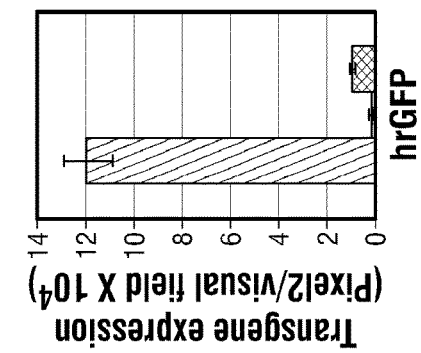
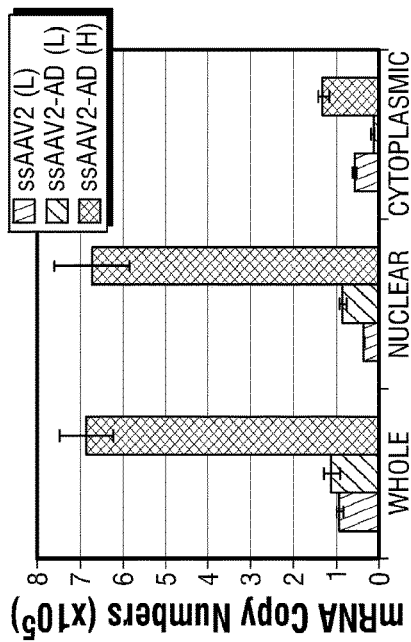
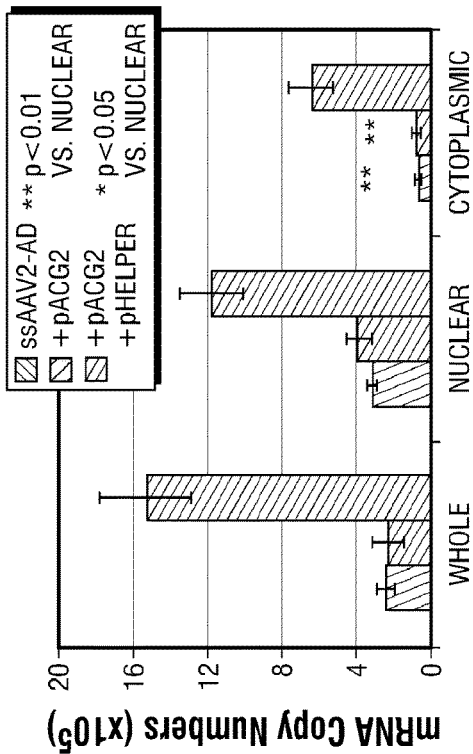
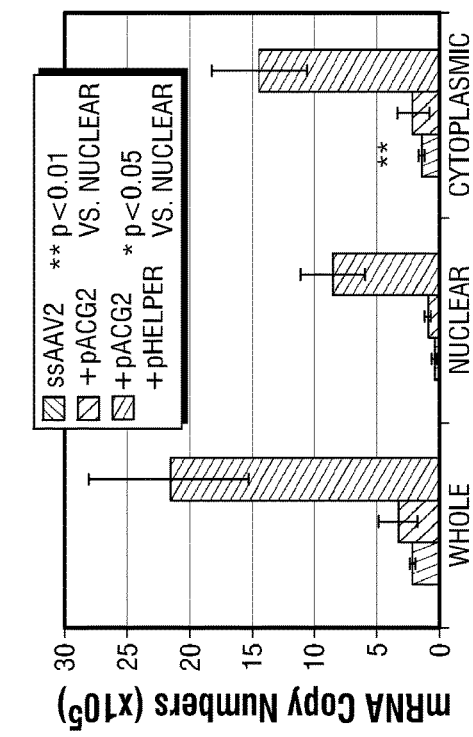

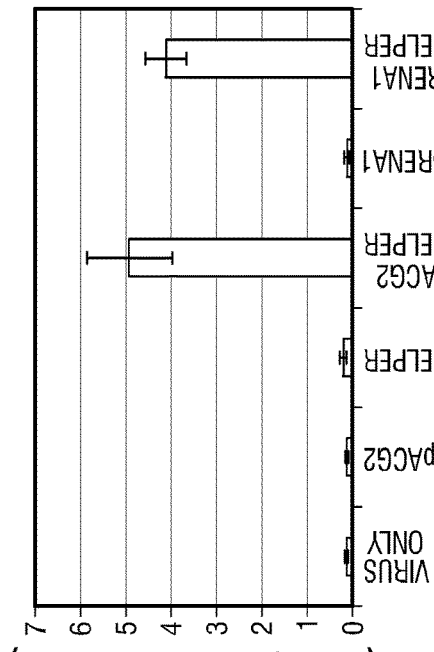
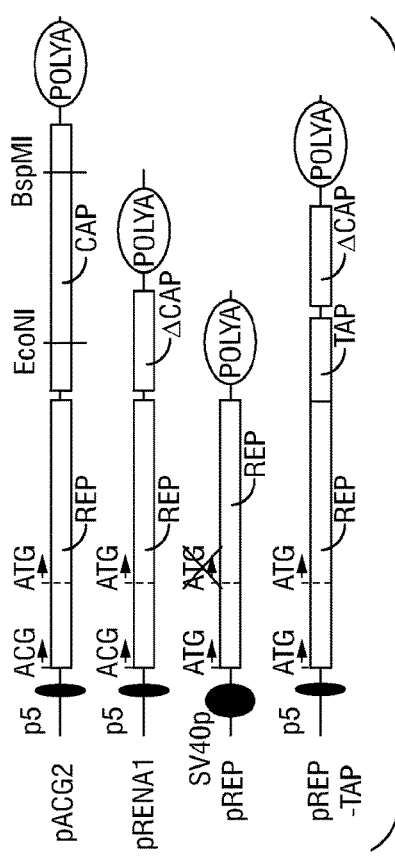
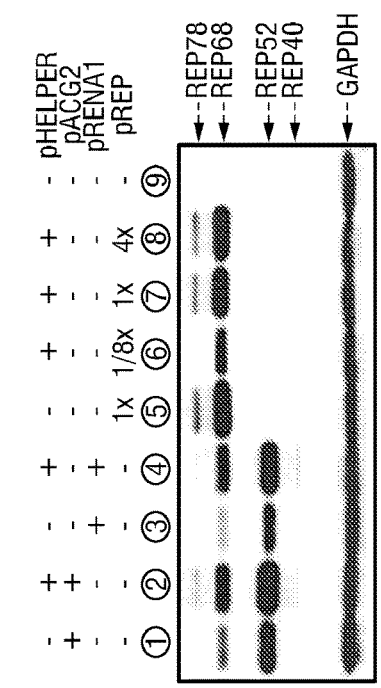
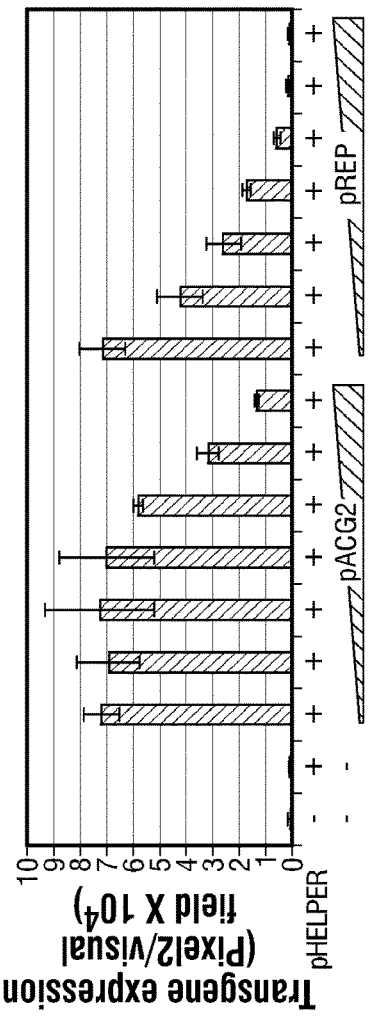
FIG. 6A
FIG. 6B
FIG. 6C
FIG. 6D

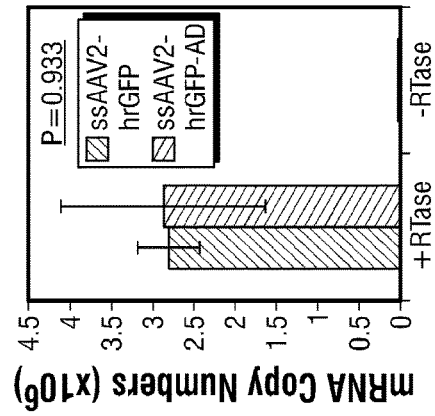
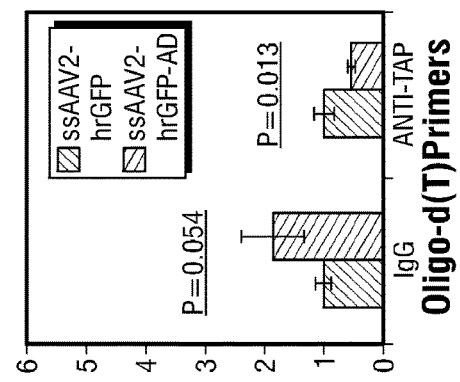
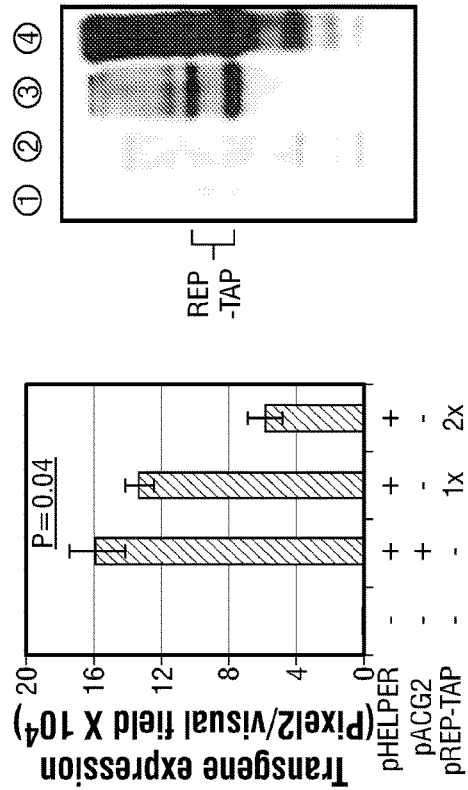
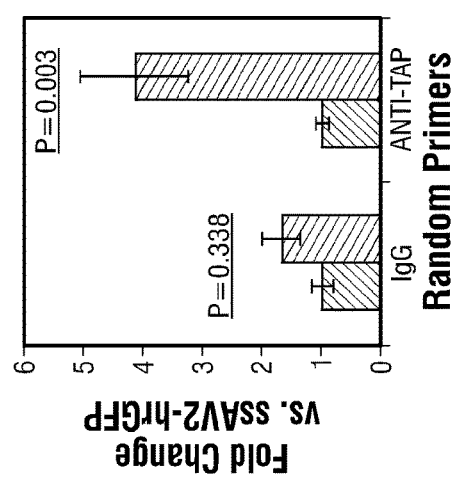
FIG. 6E  FIG. 6F  FIG. 6G  FIG. 6H  FIG. 6I

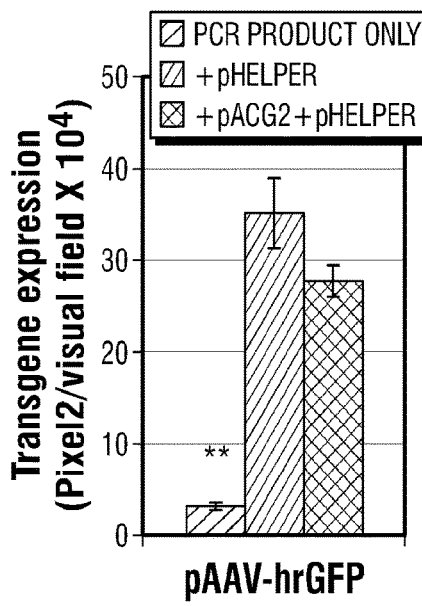
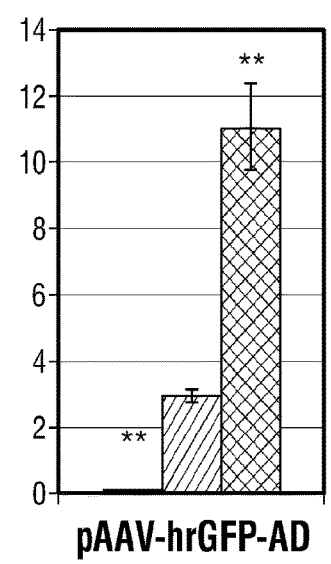
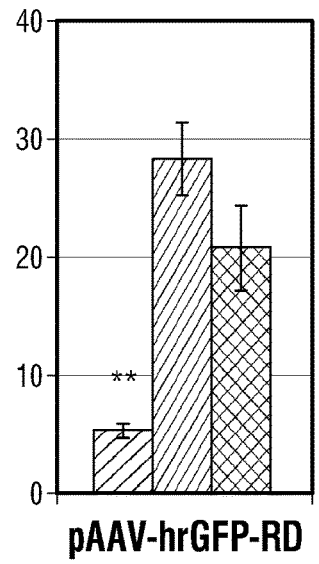
FIG. 7C-1    FIG. 7C-2    FIG. 7C-3
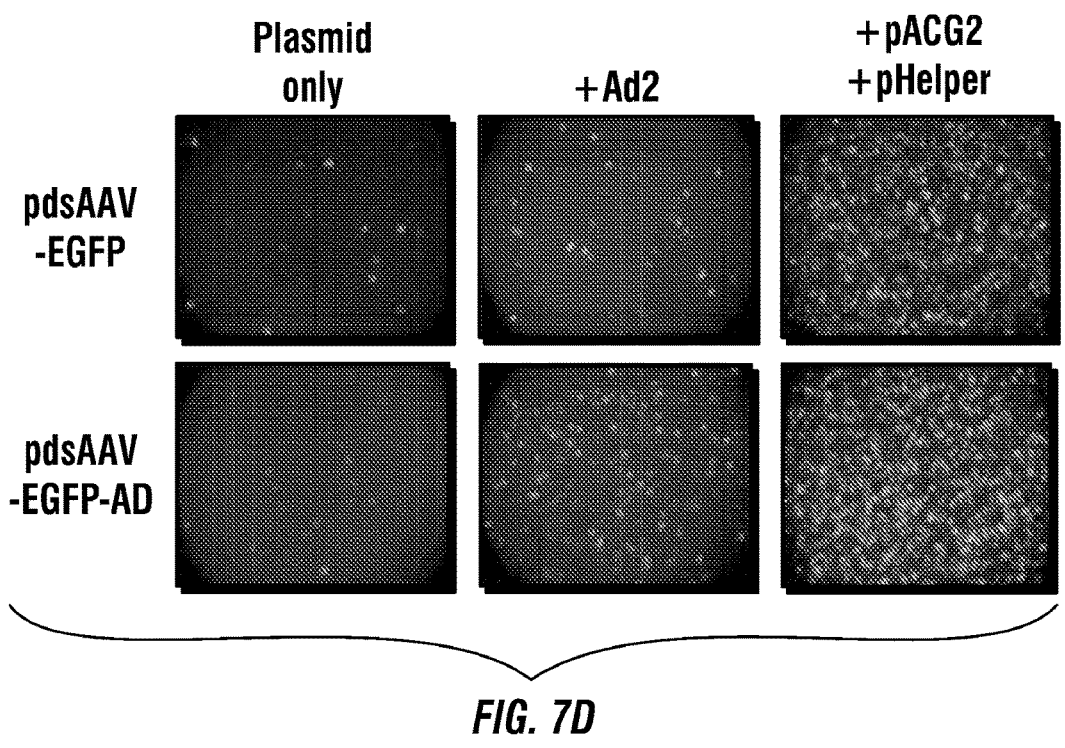
FIG. 7D

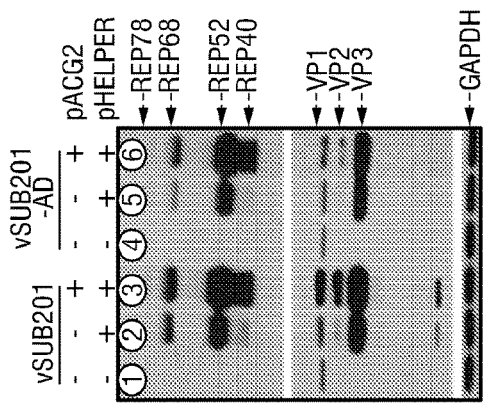
*FIG. 9A*
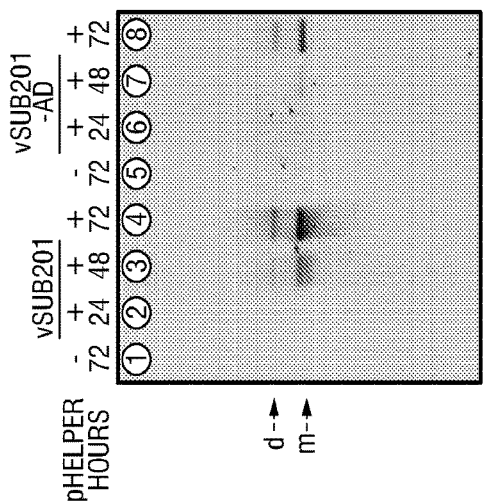
*FIG. 9B*
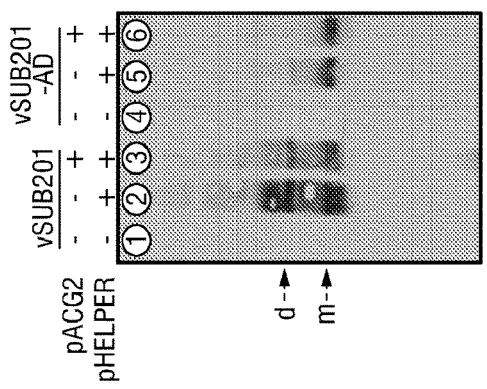
*FIG. 9D*
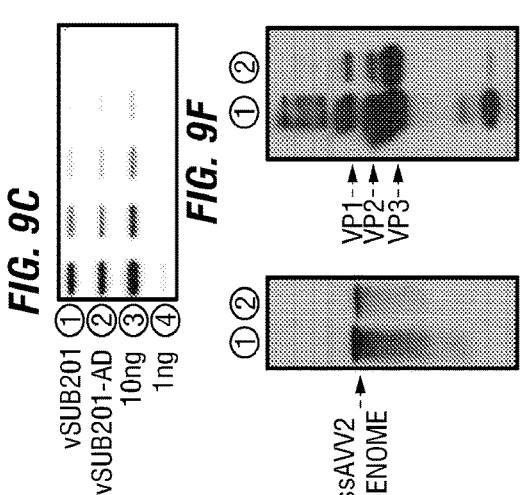
*FIG. 9C*
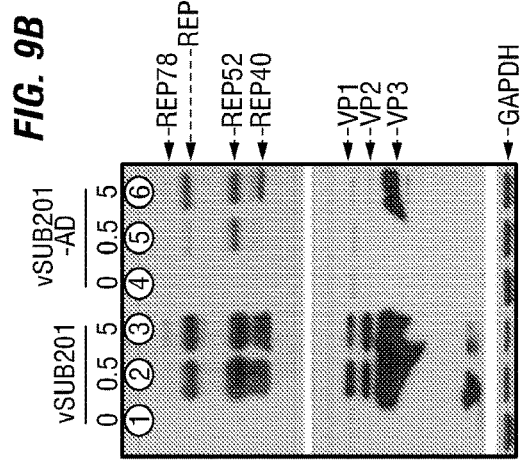
*FIG. 9E*
*FIG. 9F*
*FIG. 9G*
*FIG. 9H*

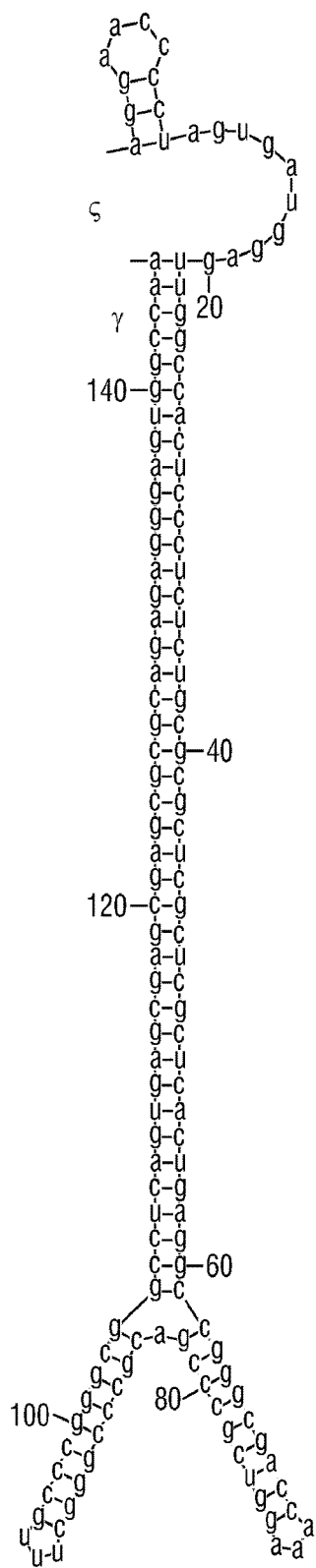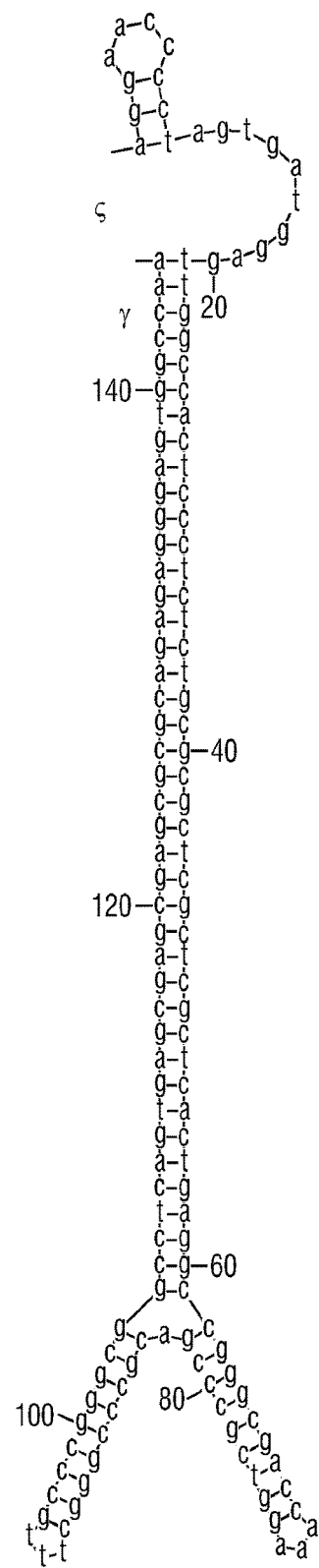
*FIG. 10A*   *FIG. 10B*

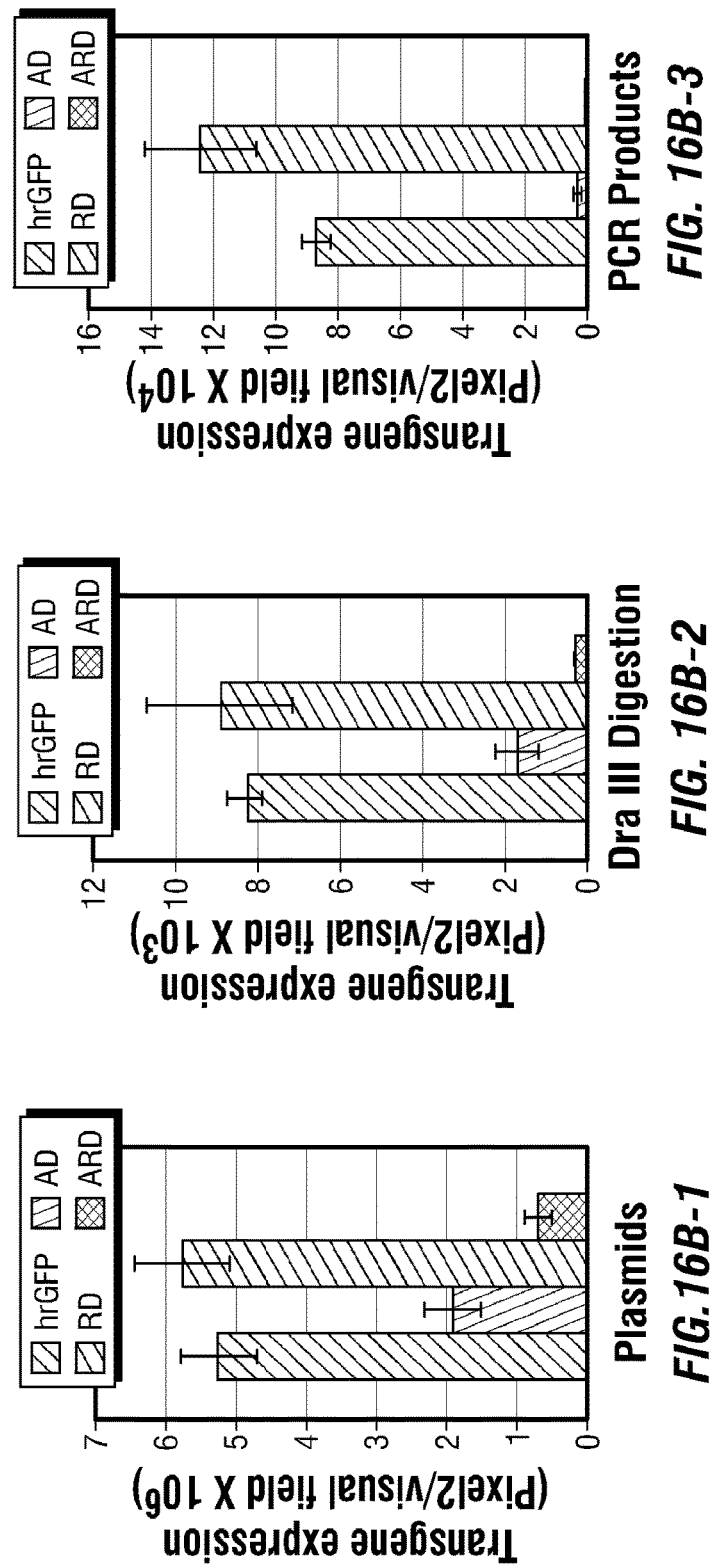

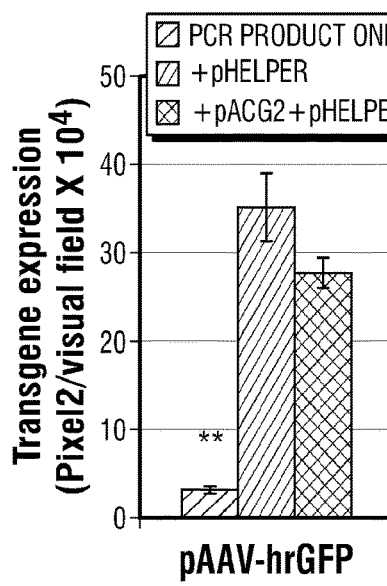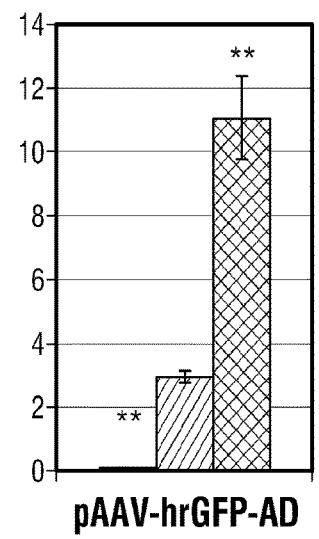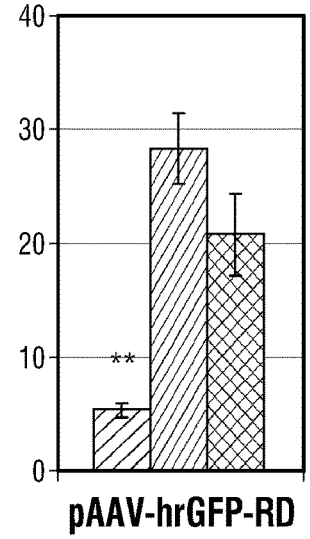
pAAV-hrGFP
FIG. 16C-1
pAAV-hrGFP-AD
FIG. 16C-2
pAAV-hrGFP-RD
FIG. 16C-3
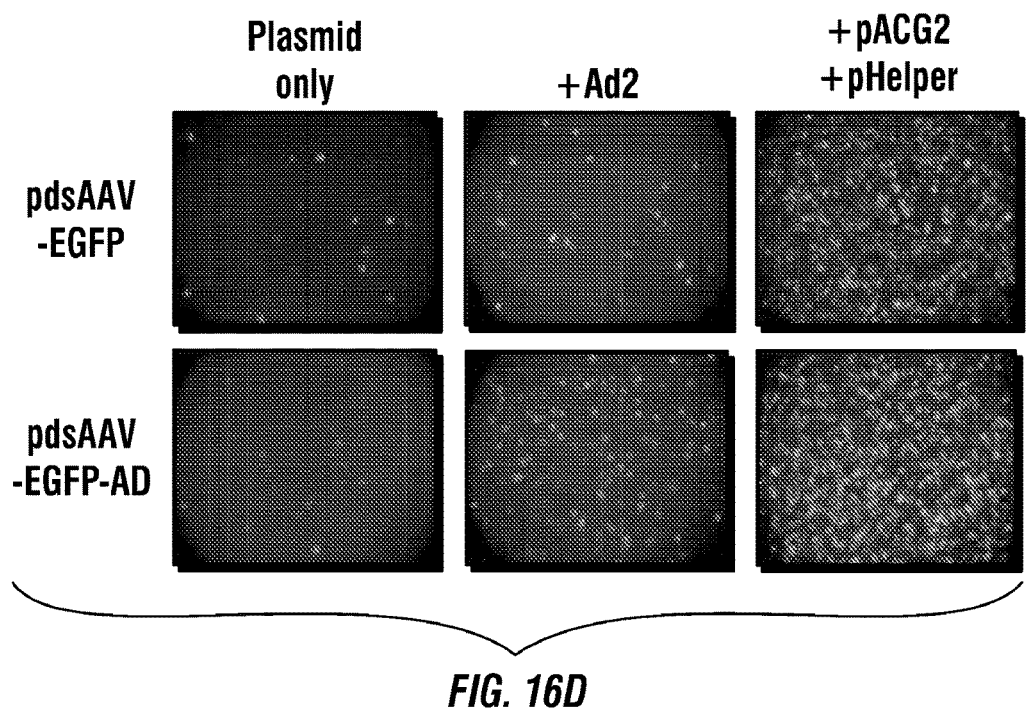
FIG. 16D

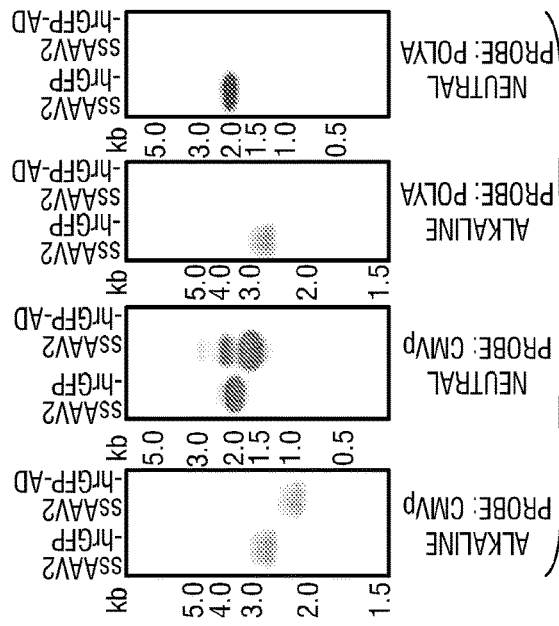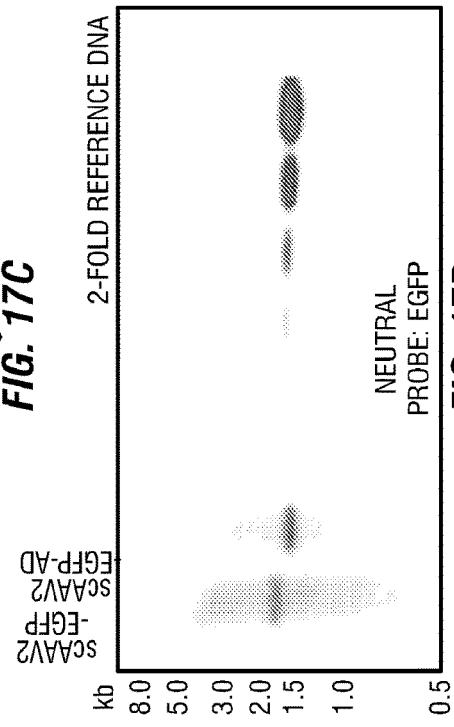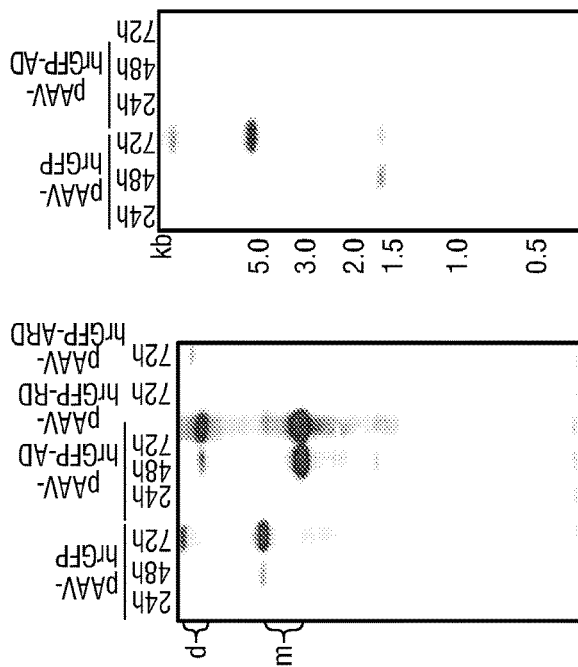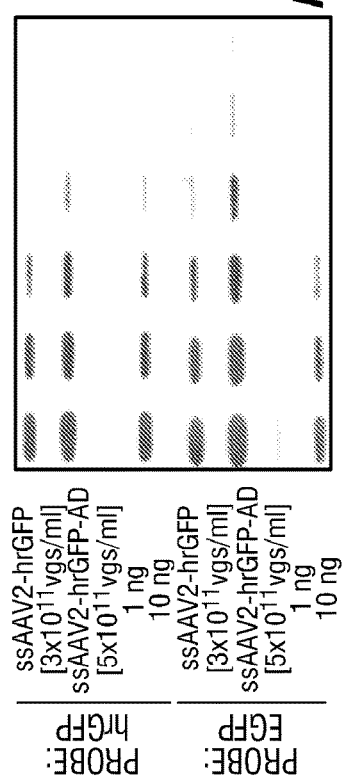
FIG. 17A-1
FIG. 17A-2
FIG. 17B
FIG. 17C
FIG. 17D

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1
gcggccgcac gcgtctagtt atta                                              24

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 2
agaaaatacc gcatcaggcg                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tgatcgagga gatgttcgtg                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
ccggtgatgg tcttcttcat                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
ttggccactc cctctctgcg                                                  20

<210> SEQ ID NO 6
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 6
cgatgcggcc gctgtagtta atgatta                                          27

<210> SEQ ID NO 7
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 7
cgatgcggcc gcttacagat tacgagtca                                        29

<210> SEQ ID NO 8
<211> LENGTH: 15
<212> TYPE: RNA
<213> ORGANISM: Adeno-associated virus 2

<400> SEQUENCE: 8
cauugcauug cauug                                                       15

<210> SEQ ID NO 9
<211> LENGTH: 12
<212> TYPE: DNA
<213> ORGANISM: Adeno-associated virus 2
```

```
<400> SEQUENCE: 9
catgcatgca tg                                                        12

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
ctgtaagcgg ccgcaggaac c                                              21

<210> SEQ ID NO 11
<211> LENGTH: 145
<212> TYPE: RNA
<213> ORGANISM: Artificial Sequence
<220> FEATURE:
<223> OTHER INFORMATION: Synthetic Polynucleotide

<400> SEQUENCE: 11
aggaaccccu agugauggag uuggccacuc ccucucugcg cgcucgcucg cucacugagg     60
ccgggcgacc aaaggucgcc cgacgcccgg gcuuugcccg ggcggccuca gugagcgagc    120
gagcgcgcag agagggagug gccaa                                         145

<210> SEQ ID NO 12
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 12
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag agagggagtg gccaa                                         145

<210> SEQ ID NO 13
<211> LENGTH: 6
<212> TYPE: DNA
<213> ORGANISM: Artificial Sequence
<220> FEATURE:
<223> OTHER INFORMATION: Synthetic Polynucleotide

<400> SEQUENCE: 13 aataaa                                                                6

<210> SEQ ID NO 14
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 14
cgatgcggcc gctgtagtta atgatta                                        27

<210> SEQ ID NO 15
<211> LENGTH: 29
<212> TYPE: DNA
<213> ORGANISM: Artificial Sequence
<220> FEATURE:
<223> OTHER INFORMATION: Synthetic Polynucleotide
```

```
<400> SEQUENCE: 15
cgatgcggcc gcttacagat tacgagtca                                        29
```

HAIRPIN MRNA ELEMENTS AND METHODS FOR THE REGULATION OF PROTEIN TRANSLATION

CROSS-REFERENCE TO RELATED APPLICATIONS

The present application is a national stage filing under 35 U.S.C. § 371 of International PCT application PCT/US2014/038460, filed May 16, 2014 which claims priority to U.S. Provisional Patent Appl. No. 61/824,319, filed May 16, 2013; the contents of each of which are hereby incorporated in their entirety herein by reference.

BACKGROUND OF THE INVENTION

Field of the Invention

The present invention relates to the fields of molecular biology, virology, protein synthesis, gene therapy, and medicine. The invention provides novel mRNA regulatory elements and methods for controlling protein expression in selected mammalian host cells. In particular embodiments, the invention provides compositions including polyA-deleted rAAV vectors that express a stably-produced mRNA that includes an inverted terminal repeat sequence at its 3-end, which forms an element having the ability to form a hairpin, double-stranded RNA structure that is independent of other non-coding RNAs such as micoRNA, siRNA, etc. mRNAs containing the stable hairpin structure lack polyadenylation signals, which allow minimal protein translation. In the presence of specific proteins, however, high levels of protein translation can be obtained, and precisely controlled. The resulting vectors are particularly useful in diagnostic and/or therapeutic regimens, including, for example, the treatment of one or more mammalian disorders or diseases, and in particular, for treating defects resulting from a decrease in, or an absence of expression of one or more particular polypeptides. Also provided are methods for preparing rAAV vector-based medicaments for use in viral vector-based gene therapies.

Description of Related Art

Two major mechanisms or strategies exist for controlling protein expression in mammalian cells. One is the use of tissue-specific promoters; the other is the use of siRNA. However, these methods rely upon regulation at the transcriptional level (i.e., the process of synthesizing mRNA from its DNA template), and not upon regulation at the translational level (i.e., synthesizing the encoded protein from the mRNA message). Conventional siRNA-based methods have focused on the inhibition of translation of mRNA into protein (i.e., decreasing the amount of protein produced).

What is lacking in the prior art, however, are methods that permit the enhancement, i.e., an increase, of protein translation from mRNAs.

BRIEF SUMMARY OF THE INVENTION

The present invention overcomes these and other limitations inherent in the prior art by providing novel hairpin mRNA elements that are useful in the regulation of protein translation in selected mammalian cells. In particular, the novel compositions of the present invention can be utilized in conjunction with the use of one or more regulatable promoters, and/or one or more siRNAs to achieve different levels of gene expression, either transcriptionally (from DNA to mRNA), or translationally (from mRNA to its encoded protein).

The formation of the double-stranded RNA structure at the 3'-end untranslated region (UTR) of a messenger RNA (mRNA), for example, by the binding of microRNA, can halt the protein translation from this mRNA. The present invention provides a novel method for introducing an RNA element into the 3'UTR of an mRNA of interest. This mRNA element has the ability to form a hairpin, double-stranded, RNA structure independent of other non-coding RNAs, such as microRNA, siRNA, and the like. mRNAs containing this element are stably expressed, lack polyadenylation tails, and allow minimal protein translation. However, the protein translation can be significantly enhanced to high levels in the presence of specific proteins. Thus, through the introduction of a novel hairpin RNA element at the 3'UTR of an mRNA, the translation of protein products can be precisely regulated.

The invention further provides a vector comprising an mRNA regulatory element that contains a first polyA-deleted, ITR-containing transgene cassette that is capable of altering protein translation from an mRNA segment operably linked thereto. Preferably, the vector further comprises at least a first promoter operably linked to the mRNA segment wherein the promoter is capable of expressing the segment in a selected host cell, and in particular, in a mammalian, and preferably, human host cell.

The vectors of the present invention preferably further include at least a first contiguous nucleic acid segment isolated from a first AAV2 right ITR sequence that is sufficient to mediate detectable levels of transgene expression in a polyA-deleted expression cassette.

In certain embodiments, the vector will be preferably comprised within an adeno-associated viral particle, virion, or infectious virion, or within an isolated mammalian host cell, such as a human cell.

The invention further provides isolated nucleic acid molecules that encode a double-stranded mRNA hairpin regulatory element as described herein.

Also provided are compositions that include (a) one or more of the disclosed vectors and (b) a pharmaceutically-acceptable buffer, diluent, or vehicle. Such compositions may preferably be included within a kit for diagnosing, preventing, treating or ameliorating one or more symptoms of a mammalian disease, injury, disorder, trauma or dysfunction. The mRNA regulatory elements and compositions comprising them find particular utility in gene expression constructs, and particularly for use in diagnosis, therapy, prevention, or amelioration of one or more symptoms of cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, ischemia, eating disorder, $\alpha_1$-antitrypsin (AAT) deficiency, Batten's disease, Alzheimer's disease, Huntington's disease, Parkinson's disease, skeletal disease, trauma, or pulmonary disease in a mammal.

Use of a composition as disclosed herein in the manufacture of a medicament for diagnosing, treating, preventing or ameliorating one or more symptoms of a disease, a disorder, a dysfunction, an injury, an abnormal condition, a congenital defect, or trauma in a mammal is also an important aspect of the present invention.

The invention also provides a method for regulating protein expression in a mammalian host cell. The method, in an overall and general sense includes introducing into one or more cells of the population, a composition that comprises an effective amount of one or more of the protein translation regulatory vectors as described herein. Preferably, the methods of the present invention are useful in the regulation and expression of proteins from one or more mRNA sequence in mammalian host cells, and in human host cells in particular. Exemplary host cells include, without limitation, endothelial, epithelial, vascular, liver, lung, heart, pancreas, intestinal, kidney, muscle, bone, dendritic, cardiac, neural, blood, brain, fibroblast, and cancer cells.

In one embodiment, the invention concerns expression vectors that comprise at least a first nucleic acid segment operably linked to one or more mRNA regulatory elements that are capable of regulating translation of protein from an mRNA segment. Preferably the construct comprises at least a first nucleic acid region that encodes one or more diagnostic or therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the overexpression of an endogenous biological compound, while in other embodiments still; the defect may be caused by the under-expression or even lack of one or more endogenous biological compounds.

When the use of such vectors is contemplated for introduction of one or more exogenous proteins, polypeptides, peptides, ribozymes, siRNAs, and/or antisense oligonucleotides, to a particular cell transfected with the vector, one may employ the modified AAV vectors disclosed herein by incorporating into the vector at least a first exogenous polynucleotide operably positioned downstream and under the control of at least a first heterologous promoter that expresses the polynucleotide in a cell comprising the vector to produce the encoded therapeutic agent, including for example, peptides, proteins, polypeptides, antibodies, ribozymes, siRNAs, and antisense oligo- or polynucleotides. Such constructs may employ one or more heterologous promoters to express the therapeutic agent of interest. Such promoters may be constitutive, inducible, or even cell- or tissue-specific. Exemplary promoters include, but are not limited to, a CMV promoter, a β-actin promoter, a hybrid CMV promoter, a hybrid β-actin promoter, an EF1 promoter, a U1a promoter, a U1b promoter, a Tet-inducible promoter, a VP16-LexA promoter, a joint-specific promoter and a human-specific promoter.

The genetically-modified rAAV vectors or expression systems of the invention may also further comprise a second nucleic acid segment that comprises, consists essentially of, or consists of, one or more enhancers, regulatory elements, transcriptional elements, to alter or effect transcription of the heterologous gene cloned in the rAAV vectors. For example, the rAAV vectors of the present invention may further comprise a second nucleic acid segment that comprises, consists essentially of, or consists of, at least a first CMV enhancer, a synthetic enhancer, or a cell- or tissue-specific enhancer. The second nucleic acid segment may also further comprise, consist essentially of, or consist of one or more intron sequences, post-transcriptional regulatory elements, or such like. The vectors and expression systems of the invention may also optionally further comprise a third nucleic acid segment that comprises, consists essentially of, or consists of, one or more polylinker or multiple restriction sites/cloning region(s) to facilitate insertion of one or more selected genetic elements, polynucleotides, and the like into the rAAV vectors at a convenient restriction site.

In aspects of the invention, the exogenous polynucleotides that are comprised within one or more of the improved rAAV vectors disclosed herein are preferably of mammalian origin, with polynucleotides encoding polypeptides and peptides of human, primate, murine, porcine, bovine, ovine, feline, canine, equine, epine, caprine, or lupine origin being particularly preferred.

As described above, the exogenous polynucleotide will preferably encode one or more proteins, polypeptides, peptides, enzymes, antibodies, siRNAs, ribozymes, or antisense polynucleotides, oligonucleotides, PNA molecules, or a combination of two or more of these therapeutic agents. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the invention also provides genetically-modified rAAV vectors that are comprised within an infectious adeno-associated viral particle or a virion, or pluralities of such particles, which themselves may also be comprised within one or more diluents, buffers, physiological solutions or pharmaceutical vehicles, formulated for administration to a mammal such as a human for therapeutic, and/or prophylactic gene therapy regimens. Such vectors, virus particles, virions, and pluralities thereof may also be provided in excipient formulations that are acceptable for veterinary administration to selected livestock, exotic or domesticated animals, companion animals (including pets and such like), as well as non-human primates, zoological or otherwise captive specimens, and such like, wherein the use of such vectors and related gene therapy is indicated to produce a beneficial effect upon administration to such an animal.

The invention also concerns host cells that comprise at least one of the disclosed rAAV vectors, virus particles, or virions. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle. Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or subsynovium tissue, tendons, ligaments, cartilages, bone, periarticular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathorascic, intravascular, or intracerebroventricular delivery.

Other aspects of the invention concern recombinant adeno-associated virus virion particles, compositions, and host cells that comprise, consist essentially of, or consist of, one or more of the rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed rAAV vectors, virions, viral particles, transformed host cells or pharmaceutical compositions comprising such; and instructions for using the kit in a therapeutic, diagnostic, or clinical embodiment also represent preferred aspects of the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Such kits may be therapeutic kits for treating, preventing, or ameliorating the symptoms of a disease, deficiency, dysfunction, and/or injury, and may comprise one or more of the modified rAAV vector constructs, expression systems, virion particles, or a plurality of such particles, and instructions for using the kit in a therapeutic and/or diagnostic medical regimen. Such kits may also be used in large-scale production methodologies to produce large quantities of the viral vectors themselves (with or without a therapeutic agent encoded therein) for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for preventing, treating or ameliorating the symptoms of various diseases, dysfunctions, or deficiencies in an animal, such as a vertebrate mammal. Such methods generally involve administration to a mammal, or human in need thereof, one or more of the disclosed vectors, virions, viral particles, host cells, compositions, or pluralities thereof, in an amount and for a time sufficient to prevent, treat, or lessen the symptoms of such a disease, dysfunction, or deficiency in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

In other embodiment, the invention also concerns the disclosed rAAV vectors comprised within an infectious adeno-associated viral particle, comprised within one or more pharmaceutical vehicles, and may be formulated for administration to a mammal such as a human for therapeutic, and/or prophylactic gene therapy regimens. Such vectors may also be provided in pharmaceutical formulations that are acceptable for veterinary administration to selected livestock, domesticated animals, pets, and the like.

The invention also concerns host cells that comprise the disclosed rAAV vectors and expression systems, particularly mammalian host cells, with human host cells being particularly preferred.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Other aspects of the invention concern recombinant adeno-associated virus virion particles, compositions, and host cells that comprise one or more of the AAV vectors disclosed herein, such as for example pharmaceutical formulations of the vectors intended for administration to a mammal through suitable means, such as, by intramuscular, intravenous, or direct injection to cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed vectors, virions, host cells, viral particles or compositions; and (ii)

instructions for using the kit in therapeutic, diagnostic, or clinical embodiments also represent preferred aspects of the present disclosure. Such kits may further comprise one or more reagents, restriction enzymes, peptides, therapeutics, pharmaceutical compounds, or means for delivery of the compositions to host cells, or to an animal, such as syringes, injectables, and the like. Such kits may be therapeutic kits for treating or ameliorating the symptoms of particular diseases, and will typically comprise one or more of the modified AAV vector constructs, expression systems, virion particles, or therapeutic compositions described herein, and instructions for using the kit.

Another important aspect of the present invention concerns methods of use of the disclosed vectors, virions, expression systems, compositions, and host cells described herein in the preparation of medicaments for treating or ameliorating the symptoms of various polypeptide deficiencies in a mammal. Such methods generally involve administration to a mammal, or human in need thereof, one or more of the disclosed vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 2A, FIG. 2B, FIG. 2C, FIG. 2D, FIG. 2E, FIG. 2F, and FIG. 2G show the characterization of 3'-end of rAAV2 transcripts and their cellular distribution. FIG. 2A: Schematic structures of rAAV2 vectors containing various indicated rAAV vector genomes. Total RNAs from HEK293 or HeLa cells were extracted 24 hrs post-transduction with rAAV2 vectors at 5,000 vgs/cell. RNAs were subjected to reverse transcription using (FIG. 2B) ITR primers, (FIG. 2C) random primers or (FIG. 2D) oligo-d(T) primers, and subsequent qPCR assays specific for hrGFP. FIG. 2E: The distribution of cytosolic and nuclear proteins in subcellular fractions. The purity of samples was demonstrated by probing with antibodies directed against IκB and Lamin B, respectively. W: whole cell; C: cytoplasmic; N: nuclear. $5 \times 10^5$ HEK293 (FIG. 2F) and $5 \times 10^5$ HeLa (FIG. 2G) cells were transduced with either ssAAV2 or ssAAV2-AD vectors at 5,000 vgs/cell. Total RNA from either fraction was extracted 24 hrs post-infection. RNA samples were reverse transcribed using random primers and then subjected to qPCR analysis;

FIG. 3A, FIG. 3B, FIG. 3C, FIG. 3D, and FIG. 3E show polyA-deleted rAAV2 vector-mediated transgene expression. FIG. 3A: Cells were transduced with rAAV2 vectors at 2,000 vgs/cell. FIG. 3B: HEK293 cells were transduced with rAAV2 at 5,000 vgs/cell, followed by transfection with either pACG2 and/or pHelper plasmids. Representative images are shown. FIG. 3C: Quantitative analyses of the data from FIG. 3B. FIG. 3D: Fold-change in transgene expression compared with virus only group (rAAV2) as a function of time after vector transduction. FIG. 3E: Cells were transduced with ssAAV2-AD vectors at 5,000 vgs/cell, followed by transfection with either pACG2 and/or pHelper plasmids. All transgene expression was detected by fluorescence microscopy 72 hrs post-transduction and images from three independent experiments were analyzed quantitatively by ImageJ analysis software;

(FIG. 4A) HEK293 and (FIG. 4B) HeLa cells were transduced with scAAV2 vectors, followed by transfection with pACG2 or/and pHelper plasmids. Plasmid pdsAAV-CBAp-EGFP was used as a positive control. Low-$M_r$ DNA was isolated 72 hrs post-transfection, and was digested extensively with DpnI. Southern blots were performed using $^{32}$P-labeled EGFP-specific DNA probe. The exposure time was 4 hrs and 24 hrs for FIG. 4A and FIG. 4B, respectively. The monomeric and dimeric forms of replicative DNA intermediates are denoted as m and d, respectively;

FIG. 5A, FIG. 5B, FIG. 5C, and FIG. 5D show functions of AAV2 and adenoviral genes in polyA-deleted rAAV2 mRNA transcription, cellular distribution and translation. FIG. 5A: HEK293 cells were either transduced with ssAAV2 (L) or ssAAV2-AD (L) at 5,000 vgs/cell or ssAA2-AD (H) at 50,000 vgs/cell. Transgene expression was detected by fluorescence microscopy 24 hrs post-transduction. Representative images are shown. FIG. 5B: Total RNAs from FIG. 5A were extracted from whole cells, nuclear, and cytoplasmic fractions. RNAs were then subjected to reverse transcription using random primers followed by qPCR assays. HEK293 cells were transduced with either (FIG. 5C) ssAAV2 or (FIG. 5D) ssAAV2-AD vectors at 5,000 vgs/cell, followed by mock-transfection or transfection with pACG2 and/or pHelper plasmids. Total RNAs were extracted 24 hrs post-transfection from whole cells, nuclear, and cytoplasmic fractions. RNAs were then subjected to reverse transcription using random primers followed by qPCR assays;

FIG. 6A, FIG. 6B, FIG. 6C, FIG. 6D, FIG. 6E, FIG. 6F, FIG. 6G, FIG. 6H, and FIG. 6I show the role of AAV2 Rep genes in transgene expression from polyA-deleted mRNA transcripts. FIG. 6A: Schematic structures of plasmids containing WT AAV2 genes. FIG. 6B: HeLa cells were transduced with ssAAV2-hrGFP-AD vectors at 5,000 vgs/cell, followed by transfection with the indicated plasmids. FIG. 6C: HeLa cells were transduced with ssAAV2-hrGFP-AD at 5,000 vgs/cell, followed by transfection with pHelper plasmid and increasing amount of pACG2 or pRep plasmids (12.5 ng to 400 ng per 96-well). FIG. 6D: HeLa cells were transfected with 3 μg of pHelper, 1.5 μg pACG2, 1.5 μg pRena1, and increasing concentrations (0.2 μg, 1.5 μg, and 6 μg) of pRep plasmids, respectively, together with transduction with ssAAV2-hrGFP-AD vectors. Western blot analysis was performed with 1F antibody. Anti-GAPDH monoclonal antibody was used to quantify the protein loading. FIG. 6E: HEK293 cells were transduced with ssAAV2- hrGFP-AD vectors at 5,000 vgs/cell, followed by transfection with the indicated plasmids. FIG. 6F: The efficiency of co-IP assays. IP was performed with anti-TAP antibody and Western blot analysis was performed with 1F antibody. FIG. 6G: Quantitative RT-PCR results from mRNA extracted from whole cells. FIG. 6H: Co-IP mRNA transcripts were reverse transcribed using random primers. FIG. 6I: Co-IP mRNA transcripts were reverse transcribed using oligo-d(T) primers. qPCR assays were performed using primers specific for hrGFP. All transgene expression was detected by fluorescence microscopy 72 hrs post-transduction and images from three independent experiments were analyzed quantitatively by ImageJ analysis software;

FIG. 7A, FIG. 7B, FIG. 7C, FIG. 7D, and FIG. 7E show double-stranded rAAV plasmid DNA-mediated transgene gene expression with and without a conventional polyA sequence. FIG. 7A: Schematic structures of plasmids containing various indicated rAAV vector genomes. Horizontal arrows: PCR primers; Vertical arrows: DraIII restriction sites. FIG. 7B: HEK293 cells were transfected with either the recombinant plasmids, or DraIII linearized plasmids, or DNA fragments amplified by PCR. FIG. 7C: DNA fragments amplified by PCR were transfected into HEK293 cells, together with pACG2 and pHelper plasmids. FIG. 7D: Plasmids were transfected into HEK293 cells, and co-infection with Ad2 at an MOI of 1, or co-transfection with pACG2 and pHelper plasmids. FIG. 7E: Plasmids were transfected into HeLa cells, together with Ad2 co-infection at an MOI of 1. All transgene expression was detected by fluorescence microscopy or flow cytometry 48 hrs post-transfection and images from three independent experiments were analyzed quantitatively by ImageJ analysis software;

FIG. 8A shows the schematic outline of plasmids containing WT AAV2 genome. Arrows: WT AAV2 promoters; Red letters: Stop codon of cap gene; Blue letters: NotI restriction site; Underlined Letters: ITR sequence. This figure depicts SEQ ID NO: 10. FIG. 8B shows the analysis of the efficiency of the WT AAV2 genomes rescue and replication. The monomeric and dimeric forms of replicative DNA intermediates are marked as m and d, respectively. FIG. 8C illustrates HEK293 cells transfected with indicated plasmids, which was followed by extraction of whole cell proteins 48 hrs post-infection. Western blot analysis was performed with anti-Rep antibody (upper) and anti-Cap antibody (middle). Anti-GAPDH monoclonal antibody was used to quantify the protein loading (lower). FIG. 8D shows quantitative DNA slot-blots for determining the viral titer stocks. pSub201 (1 ng, 10 ng), was also used as an appropriate control. FIG. 8E is a Southern blot analysis of the nature of the WT AAV2 DNA genomes in viral stocks, using alkaline agarose gels. FIG. 8F is a Western blot analysis of denatured viral capsids from viral stocks;

FIG. 9A, FIG. 9B, FIG. 9C, FIG. 9D, FIG. 9E, FIG. 9F, FIG. 9G, and FIG. 9H show gene expression, genome replication and progeny virus production from virus containing polyA-deleted WT AAV2 genome. FIG. 9A: Analysis of the efficiency of the WT AAV2 genomes replication. HEK293 cells were infected with indicated virus, followed by transfection with indicated plasmids. Low-$M_r$ DNA was isolated 72 hrs post-infection and digested intensively by DpnI. Southern blots were performed using Rep-specific probes. FIG. 9B: Time-dependent WT AAV2 genomes replication. Low-$M_r$ DNA was isolated 24, 48 and 72 hrs post-transfection. FIG. 9C: Western blot analysis was performed with anti-Rep antibody (upper) and anti-Cap antibody (middle). Anti-GAPDH monoclonal antibody was used to quantify the protein loading (lower). FIG. 9D: HEK293 cells were infected with WT and polyA-deleted AAV2, and co-infected with Ad2 at various indicated MOIs. Low-$M_r$ DNA was isolated 72 hrs post-infection. FIG. 9E: HEK293 cells were infected with the indicated AAV2, and co-infected with Ad2 at various MOIs. Whole-cell proteins were extracted 48-hours' post-infection. FIG. 9F: Quantitative DNA slot-blots for determining the secondary viral titer stocks. Two-fold serial dilutions of the viral stocks were analyzed on the blot probed with $^{32}$P-labeled Rep-specific DNA probe. pSub201 (1 ng, 10 ng), was also used as an appropriate control. FIG. 9G: Southern blot analysis of the nature of the WT AAV2 DNA genomes in secondary viral stocks, using alkaline agarose gels. FIG. 9H: Western blot analysis of denatured viral capsids from secondary viral stocks;

FIG. 10A, FIG. 10B, FIG. 10C, and FIG. 10D show structural models. FIG. 10A: Structural model of the predicted AAV2 ITR RNA secondary structure and (FIG. 10B) predicted AAV2 ITR DNA secondary structure generated in mFOLD. Structural models of AAV2 Rep78, amino acids 1-193, based on the crystal structure of AAV5 Rep78, PDB accession#1m55, are shown interacting with either an RNA 26-mer (FIG. 10C) or a DNA 26-mer (FIG. 10D) containing the AAV2 Rep Binding Sequence (RBS). Five copies of the AAV2 N-terminal 193 amino acids of Rep78 are shown in light pink, yellow, blue, green and magenta; FIG. 10A depicts SEQ ID NO: 11. FIG. 10B depicts SEQ ID NO: 12.

FIG. 13A: $1 \times 10^4$ HEK293 cells were transduced with rAAV2 vectors at 5,000 vgs/cell, followed by transfection with either pACG2 (100 ng) and/or pHelper (100 ng) plasmid. FIG. 13B: $1 \times 10^4$ HEK293 cells were transduced with rAAV2 vectors at 5,000 vgs/cell. Cells were then transfected with either pACG2 (100 ng) and/or pHelper (100 ng) plasmids 48 hrs' post-infection. FIG. 13C: $1 \times 10^4$ HEK293 cells were transduced with rAAV2 vectors at 200 vgs/cell, followed by transfection with either pACG2 and/or pHelper plasmids. FIG. 13D: $1 \times 10^4$ HeLa cells were transduced with rAAV2 at 500 vgs/cell, followed by mock-transfection or transfection with pACG2 (100 ng) and pHelper (100 ng) plasmid. FIG. 13E: $1 \times 10^4$ HEK293 cells were transduced with increasing MOI of rAAV2 vectors, followed by mock-transfection or transfection with pACG2 (100 ng) and pHelper (100 ng) plasmids. All transgene expression was detected by fluorescence microscopy or flow cytometry 72 hrs post-transduction and images from three independent experiments were analyzed quantitatively by ImageJ analysis software;

FIG. 14A: $1 \times 10^4$ HEK293 cells were transduced with rAAV2 vectors at 2,000 vgs/cell, followed by transfection with increasing amounts of pACG2 (from 50 ng to 200 ng) and pHelper (from 50 ng to 200 ng) plasmids. FIG. 14B: 1×10⁴ HEK293 cells were transduced with rAAV2 vectors at 2,000 vgs/cell, followed by mock-transfection or transfection with pACG2 (100 ng) and pHelper (100 ng) plasmids, using Lipofectamine 2000 (Lipo), or calcium phosphate (CaCl2). Representative images are shown. FIG. 14C: Quantitation of the transduction efficiency in HEK293 cells in FIG. 14B. All transgene expression was detected by fluorescence microscopy 72 hrs post-transduction and images from three independent experiments were analyzed quantitatively by ImageJ analysis software;

FIG. 15A: 1×10⁴ HeLa cells were transduced with ssAAV2-hrGPF-AD vectors at 5,000 vgs/cell, followed by transfection with the indicated plasmids using increasing amounts of transfection agent, PEI. 1×10⁴ HeLa (FIG. 15B) and 1×10⁴ HEK293 cells (FIG. 15C) were transduced with ssAAV2-hrGPF-AD vectors at 5,000 vgs/cell, followed by transfection with the indicated plasmids (100 ng). 1×10⁴ HEK293 cells were transduced with either (FIG. 15D) ssAAV2-hrGPF-AD or (FIG. 15E) scAAV2-EGFP-AD vectors at 5,000 vgs/cell, followed by transfection with pHelper (100 ng) and increased amounts of plasmids pACG2 or pRep (from 12.5 ng to 400 ng). FIG. 15F: 5×10⁵ HEK293 cells were transfected with 3 μg of pHelper, 1.5 μg pACG2, 1.5 μg Renal and increasing concentrations of pRep plasmids, respectively, together with infection with ssAAV2-hrGFP-AD vectors. Whole cell extracts (20 jig) prepared 48-hrs' post-transfection, were electrophoresed on 12% polyacrylamide-SDS gels. Western blot analysis was performed using 1F antibody. Anti-GAPDH monoclonal antibody was used to quantify the protein loading. FIG. 15G: 5×10⁵ HEK293 cells were transfected with 1.5 jig pACG2 (lane 1); 1.5 jig pACG2 and 3 jig pHelper (lane 2); 1.5 jig pRep-TAP (lane 3) or 1.5 jig pRep-TAP and 3 jig pHelper (lane 4) plasmids. Whole cell extracts (20 jig) prepared 48 hrs post-transfection, were electrophoresed on 12% polyacrylamide-SDS gel. Western blot analysis was performed using 1F antibody (left panel) or anti-TAP polyclonal antibody (right panel). Anti-GAPDH monoclonal antibody was used to quantify the protein loading;

FIG. 16A, FIG. 16B, FIG. 16C, FIG. 16D, and FIG. 16E show double-stranded rAAV plasmid DNA-mediated transgene gene expression with and without a conventional polyA sequence. FIG. 16A: Schematic structures of plasmids containing various indicated rAAV vector genomes. Horizontal arrows: PCR primers; Vertical arrows: DraIII restriction sites. FIG. 16B: HEK293 cells were transfected with either the recombinant plasmids, or DraIII linearized plasmids, or DNA fragments amplified by PCR. FIG. 16C: DNA fragments amplified by PCR were transfected into HEK293 cells, together with pACG2 and pHelper plasmids. FIG. 16D: Plasmids were transfected into HEK293 cells, and co-infection with Ad2 at an M.O.I of 1, or co-transfection with pACG2 and pHelper plasmids. FIG. 16E: Plasmids were transfected into HeLa cells, together with Ad2 co-infection at an MOI of 1. All transgene expression was detected by fluorescence microscopy or flow cytometry 48 hrs post-transfection and images from three independent experiments were analyzed quantitatively by ImageJ analysis software;

FIG. 17A, FIG. 17B, FIG. 17C, and FIG. 17D show rescue, replication, and packaging of rAAV genomes. FIG. 17A is an analysis of the efficiency of rAAV genomes rescue and replication. Southern blot analysis was performed using ³²P-labeled hrGFP-specific probe, then de-probed and re-probed with ³²P-labeled polyA-specific probe. The monomeric and dimeric forms of replicative DNA intermediates are marked as m and d, respectively. FIG. 17B is a quantitative DNA slot-blot assay for determining the titers of vector stocks. ss, single-stranded; sc, self-complementary. FIG. 17C and FIG. 17D show the Southern blot analysis of the nature of the rAAV DNA genomes in vector stocks, using alkaline or neutral agarose gels. In FIG. 17C, the blots were first probed with ³²P-labeled hrGFP-specific and then with polyA-specific DNA probes. In FIG. 17D, the blots were probed with ³²P-labeled EGFP-specific DNA probe; and FIG. 18A, FIG. 18B-1 and FIG. 18B-2 show an initial study using a limited number of mice confirmed in vivo reproducibility of the in vitro results described above. Briefly, the polyA-deleted rAAV2 vectors resulted in very little transgene expression in mouse liver (FIG. 18A). However, when the plasmids pACG2 and pHelper are co-administrated, the transgene expression was significantly enhanced (FIG. 18 B).

DESCRIPTION OF POLYNUCLEOTIDE SEQUENCES

Figure 1:
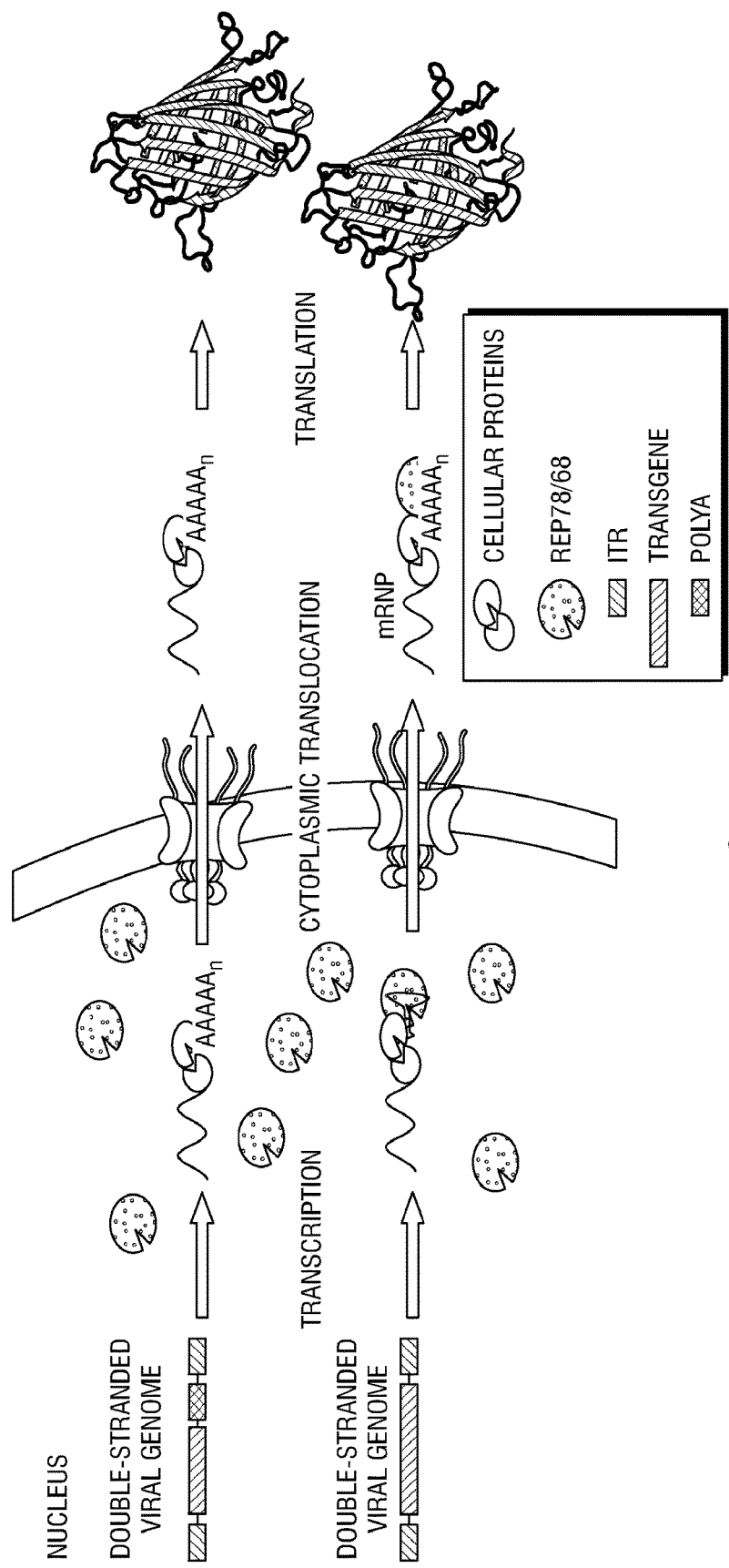
FIG. 1 shows a proposed model for the role of AAV2 ITRs at the 3'-ends of mRNA transcripts produced by polyA-deleted rAAV2 vectors.

SEQ ID NO:1 to SEQ ID NO:15, oligonucleotide primer sequences used in accordance with certain aspects of the present invention, are described in detail in the Examples which follow.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Adeno-Associated Virus 2 (AAV2)

AAV2 is a non-pathogenic human parvovirus that requires co-infection with a helper-virus, such as adenovirus (Ad), for its optimal replication[1]. In the absence of a helper-virus, the wild-type (WT) AAV2 establishes a latent infection, where the viral genome integrates site-specifically into the human chromosome 19[2,3]. The single-stranded AAV2 genome is flanked by inverted terminal repeats (ITRs) of 145 nucleotides (nts), 125-nts of which form double-stranded T-shaped hairpin structures[4]. The ITRs also contain a 20-nts long single-stranded sequence, termed the D-sequence. ITRs are the sole cis-acting elements of the WT AAV2 genome necessary for viral genome replication, encapsidation[5], and integration into as well as rescue from the host chromosomal DNA[6]. The WT AAV2 genome codes for four replication (Rep) and three capsid (Cap) proteins[7]. Several studies have demonstrated that the AAV Rep proteins specifically interact with the ITRs in AAV genome, but only in their hairpin configuration[8,9]. More recently, 188 cellular proteins have been identified that interact with Rep[10]. Some of these proteins may also interact with the AAV ITRs, either directly or indirectly. It was previously reported that a cellular protein, FKBP52, interacts with the single-stranded D-sequence[11]. The nature of this interaction was characterized and it was shown that the phosphorylation pattern of FKBP52 is a crucial determinant in the rate-limiting step of viral second-strand DNA synthesis[12-14]. Two cellular protein phosphatases, T-cell protein tyrosine phosphatase[15-18], and protein phosphatase 5[19-22], have also been identified that catalyze dephosphorylation of FKBP52. However, it is worth noticing that during the past 30 years after the first published AAV genome, all studies focus on AAV gene expression and genome replication treated AAV ITR as a DNA element. Whether the ITR sequence can be transcribed into mRNA and similar interactions occur between proteins and the ITR sequence in RNA remain open questions.

The entire WT AAV2 protein-encoding cassette can be replaced by any sequence of interest within a size limit of approximately 5 kb to generate recombinant AAV vectors (rAAV)[23]. rAAV vectors are currently in use in a number of clinical trials[24]. The most impressive therapeutic successes so far have been obtained in the treatment of Leber's congenital amaurosis[25-27], hemophilia B[28], and aromatic amino acid decarboxylase (AADC) deficiency[29]. All pre-clinical and clinical rAAV vector genomes are flanked by two AAV2 ITRs, one of which is located upstream of the promoter region and the other of which is located downstream of the polyadenylation (Poly A) signal. Two independent studies have previously documented that the left ITR in the promoter-deleted rAAV2 genome possesses enhancer and promoter activities[30-31]. In those studies, it was demonstrated that the left ITR is able to initiate trans-gene expression in a promoter-deleted construct following either plasmid transfection or rAAV2 vector-mediated transduction in cultured cells. It was hypothesized that the right ITR might possesses the function of a poly A signal in a polyA-deleted rAAV2 genome. Although previous studies have documented that all major AAV2 viral transcripts are polyadenylated[32] and subsequently, a potential 250 nucleotides polyA signal, containing the critical sequence 5'-AATAAA-3' (SEQ ID NO: 13), was identified in AAV2 genome[4], it was hypothesized that the right ITR might be transcribed into 3'-end of mRNA transcripts, if the polyA signal is deleted from the viral genome. These studies supported this hypothesis and based on these data, a model (shown in FIG. 1) has been proposed, which provides insights into the functional role of AAV2 ITR as a novel mRNA element capable of mediating efficient protein translation from polyA-deleted rAAV2 vectors and WT AAV2 virus.

Therapeutic Uses

Another aspect of the invention pertains to uses of the mRNA regulatory elements in vectors, including viral vectors such as rAAV and the like, for efficient transduction of cells, tissues, and/or organs of interest, and/or for use in gene therapy.

In one embodiment, the present invention provides a method for transduction of cells, tissues, and/or organs of interest, comprising introducing into a cell, a composition comprising an effective amount of a polynucleotide comprising at least a first mRNA regulatory element of present invention.

In particular embodiments, the mRNA regulatory elements of the present invention may be used to affect control of protein expression from one or more mRNAs encoding one or more gene products, therapeutic agents, proteins, or such like, in suitable host cells. In illustrative embodiments, the mRNA regulatory elements of the present invention may be comprised within one or more vectors, including for example, one or more viral vectors, virions, or infectious viral particles, and such like, and may be used to control, alter, regulate, or affect translation of protein from one or more nucleic acid segments encoding a selected protein of interest. In particular, such constructs may be employed in viral vectors for gene therapy applications, including, for example, in the transduction of selected mammalian host cells, including for example, human, primate, murine, feline, canine, porcine, ovine, bovine, equine, epine, caprine and lupine host cells. In certain embodiments, the rAAV vectors and virions of the invention are used for transduction of endothelial, epithelial, vascular, liver, lung, heart, pancreas, intestinal, kidney, muscle, bone, dendritic, cardiac, neural, blood, brain, fibroblast or cancer cells.

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

In addition, the present invention provides a method for treatment of a disease, wherein the method comprises administering, to a subject in need of such treatment, an effective amount of a composition comprising one or more polynucleotide sequences encoding a selected protein of interest operably positioned with one or more of the mRNA regulatory elements disclosed herein, such that the regulatory element is able to affect, alter, reduce, increase, or otherwise control translation of the encoded protein(s) from the mRNA for which the regulatory element is affecting translation.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "effective amount," as used herein, refers to an amount that is capable of treating or ameliorating a disease or condition or otherwise capable of producing an intended therapeutic effect.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction. Exemplary conditions for which rAAV viral based gene therapy may find particular utility include, but are not limited to, cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, $\alpha_1$-antitrypsin (AAT) deficiency, Batten's disease, ischemia, an eating disorder, Alzheimer's disease, Huntington's disease, Parkinson's disease, skeletal disease and pulmonary disease.

The invention also provides a method for treating or ameliorating the symptoms of such a disease, injury, disorder, or dysfunction in a mammal. Such methods generally involve at least the step of administering to a mammal in need thereof, one or more of the rAAV vectors and virions of the present invention, in an amount and for a time sufficient to treat or ameliorate the symptoms of such a disease, injury, disorder, or dysfunction in the mammal.

Such treatment regimens are particularly contemplated in human therapy, via administration of one or more compositions either intramuscularly, intravenously, subcutaneously, intrathecally, intraperitoneally, or by direct injection into an organ or a tissue of the subject under care.

The invention also provides a method for providing to a mammal in need thereof, a therapeutically-effective amount of the rAAV compositions of the present invention, in an amount, and for a time effective to provide the patient with a therapeutically-effective amount of the desired therapeutic agent(s) encoded by one or more nucleic acid segments comprised within the rAAV vector. Preferably, the therapeutic agent is selected from the group consisting of a polypeptide, a peptide, an antibody, an antigen binding fragment, a ribozyme, a peptide nucleic acid, a siRNA, an RNAi, an antisense oligonucleotide and an antisense polynucleotide.

Pharmaceutical Compositions

The present invention also provides therapeutic or pharmaceutical compositions comprising the active ingredient in a form that can be combined with a therapeutically or pharmaceutically acceptable carrier. The genetic constructs of the present invention may be prepared in a variety of compositions, and may also be formulated in appropriate pharmaceutical vehicles for administration to human or animal subjects.

The nucleic acid molecules of the present invention and compositions comprising them provide new and useful methods for the regulation of protein translation in suitable mammalian cells, and offer new opportunities for the expression of one or more selected genes of interest in such cells, and in particular, provide new methodologies for the diagnosis, treatment, control, and/or amelioration of one or more symptoms of a variety of disorders, and in particular, articular diseases, disorders, and dysfunctions, including for example osteoarthritis, rheumatoid arthritis, and such like in a mammal.

The invention also provides compositions comprising one or more of the disclosed nucleic acid regulatory elements operably linked to one or more nucleic acid molecules that is contained with a suitable vector. Exemplary vectors include, without limitation, plasmids, and viral vectors, such as rAAV vectors, expression systems, virions, viral particles; or mammalian expression systems that comprise them. As described hereinbelow, the compositions of the present invention may further comprise a pharmaceutical excipient, buffer, or diluent, and may be formulated for administration to an animal, and particularly a human being. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Such compositions may be formulated for use in a variety of therapies, such as for example, in the amelioration, prevention, and/or treatment of conditions such as peptide deficiency, polypeptide deficiency, peptide overexpression, polypeptide overexpression, including for example, conditions which result in diseases or disorders such as cancers, tumors, or other malignant growths, neurological deficit dysfunction, autoimmune diseases, articular diseases, cardiac or pulmonary diseases, ischemia, stroke, cerebrovascular accidents, transient ischemic attacks (TIA); diabetes and/or other diseases of the pancreas; cardiocirculatory disease or dysfunction (including, e.g., hypotension, hypertension, atherosclerosis, hypercholesterolemia, vascular damage or disease; neural diseases (including, e.g., Alzheimer's, Huntington's, Tay-Sach's and Parkinson's disease, memory loss, trauma, motor impairment, neuropathy, and related disorders); biliary, renal or hepatic disease or dysfunction; musculoskeletal or neuromuscular diseases (including, e.g., arthritis, palsy, cystic fibrosis (CF), amyotrophic lateral sclerosis (ALS), multiple sclerosis (MS), muscular dystrophy (MD), and such like).

In one embodiment, the nucleic acid regulatory elements of the present invention may be comprised within a vector expression system, including, without limitation, a viral vector system, such as an rAAV vector. In exemplary embodiments, such viral vectors may comprise one or more mRNAs under the control of one or more of the disclosed mRNA regulatory sequences, and as such, may be used to transform one or more populations or pluralities of mammalian cells either in vitro and/or in vivo.

In the practice of the invention, the number of rAAV vector and/or virion particles administered to such a mammal may be on the order ranging from $10^3$ to $10^{13}$ particles/ml, or any values there between, such as for example, about $10^7$, $10^8$, $10^9$, $10^{10}$, $10^{11}$, $10^{12}$, or $10^{13}$ particles/mL. In exemplary embodiments, rAAV vector and/or virion particles of a titer higher than $10^{13}$ particles/mL may be administered to one or more selected cells and/or tissues of a recipient mammal. The rAAV vectors and/or virions can be administered as a single dose, or divided into two or more administrations as may be required to achieve therapy of the particular disease or disorder being treated. In most rAAV-based gene therapy regimens, the inventors believe that a lower titer of infectious particles will be required when using the modified-capsid rAAV vectors, than compared to conventional gene therapy protocols.

In certain embodiments, the present invention concerns formulation of one or more of the disclosed hairpin mRNA regulatory elements comprised within a vector, and operably linked to at least a first mRNA for which regulation of protein translation thereof is desired. Such vectors may be formulated with one or more pharmaceutically acceptable solutions for administration to a cell or an animal, either alone or in combination with one or more other modalities of therapy, and in particular, for therapy of human cells, tissues, and diseases affecting man.

If desired, nucleic acid segments, RNA, DNA or PNA compositions that express one or more diagnostic or therapeutic gene(s) of interest may be operably linked to one or more of the mRNA regulatory elements disclosed herein, and the products thereof may then be administered to an animal (either alone, or in combination with one or more other agents as well, such as, e.g., proteins or polypeptides or various pharmaceutically-active agents, therapeutic polypeptides, biologically active fragments, or variants thereof). In fact, there is virtually no limit to other components that may also be included, given that the additional agents do not cause a significant adverse effect upon contact with the target cells or host tissues. The rAAV-based genetic compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, siRNA, mRNA, tRNA, ribozyme, catalytic RNA molecules, or PNA compositions and such like.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the AAV vector-based therapeutic constructs in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The methods of administration may also include those modalities as described in U.S. Pat. Nos. 5,543,158, 5,641,515 and/or 5,399,363 (each of which is specifically incorporated herein in its entirety by express reference thereto). Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms of the AAV-based viral compositions suitable for injectable use include sterile aqueous solutions or dispersions and sterile powders for the extemporaneous preparation of sterile injectable solutions or dispersions (U.S. Pat. No. 5,466,468, specifically incorporated herein in its entirety by express reference thereto). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present invention can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection. In preferred embodiments, the composition is administered via intranasal, pulmonary, or oral route.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active AAV vector-delivered therapeutic polypeptide-encoding DNA fragments in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV vector compositions disclosed herein may also be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

The amount of AAV compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or a relatively prolonged period of time, as may be determined by the medical practitioner overseeing the administration of such compositions.

Expression Vectors

The present invention contemplates a variety of protein expression systems, and vectors comprising one or more mRNA regulatory elements as disclosed herein. In one embodiment the preferred expression vectors comprise at least a first nucleic acid segment that encodes a therapeutic peptide, protein, or polypeptide operably linked to at least a first mRNA regulatory element that controls the translation of one or more proteins from a given mRNA to which the element is operably linked. In exemplary embodiments, the preferred expression vectors are one or more viral vectors, including, for example, an rAAV vector, that comprises at least a first nucleic acid segment that encodes a first polypeptide, whose translation in a mammalian cell is affected by the presence of one or more of the disclosed hairpin regulatory elements. In certain embodiments, one or more promoters may also be operatively linked to the nucleic acid molecule to drive expression of the mRNA in one or more suitable host cells.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the mRNA to which it and the disclosed regulatory elements are each operatively linked.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

To express a therapeutic agent in accordance with the present invention one may prepare a tyrosine-modified rAAV expression vector that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. Particularly preferred recombinant vector constructs are those that comprise a rAAV vector. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the rAAV vectors or the tyrosine-modified rAAV vectors disclosed herein by genetically modifying the vectors to further comprise at least a first exogenous polynucleotide operably positioned downstream and under the control of at least a first heterologous promoter that expresses the polynucleotide in a cell comprising the vector to produce the encoded peptide, protein, polypeptide, ribozyme, siRNA, RNAi or antisense oligonucleotide. Such constructs may employ heterologous promoters that are constitutive, inducible, or even cell-specific promoters. Exemplary such promoters include, but are not limited to, viral, mammalian, and avian promoters, including for example a CMV promoter, a .beta.-actin promoter, a hybrid CMV promoter, a hybrid .beta.-actin promoter, an EF1 promoter, a U1a promoter, a U1b promoter, a Tet-inducible promoter, a VP16-LexA promoter, and such like.

The vectors or expression systems may also further comprise one or more enhancers, regulatory elements, transcriptional elements, to alter or effect transcription of the heterologous gene cloned in the rAAV vectors. For example, the rAAV vectors of the present invention may further comprise at least a first CMV enhancer, a synthetic enhancer, or a cell- or tissue-specific enhancer. The exogenous polynucleotide may also further comprise one or more intron sequences.

Therapeutic and Diagnostic Kits

The invention also encompasses one or more of the genetically-modified vector compositions described herein together with one or more pharmaceutically-acceptable excipients, carriers, diluents, adjuvants, and/or other components, as may be employed in the formulation of particular vector-based-polynucleotide delivery formulations, and in the preparation of therapeutic agents for administration to a subject, and in particularly, to a human. In particular, such kits may comprise one or more of the disclosed vector compositions in combination with instructions for using the vector in the expression of an encoded protein, or in the administration of such a vector to an animal in need thereof, such as in methods for the treatment and/or amelioration of one or more disorders in a subject. The vectors, regulatory elements, and polynucleotides encoding them may typically further include one or more containers prepared for convenient commercial packaging, and or one or more sets of instructions for using the vectors contained therein.

As such, preferred animals for administration of the pharmaceutical compositions disclosed herein include mammals, and particularly humans. Other preferred animals include murines, bovines, equines, porcines, canines, and felines. The composition may include partially or significantly purified rAAV compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV composition(s) may be placed, and preferably suitably aliquoted. Where a second therapeutic polypeptide composition is also provided, the kit may also contain a second distinct container means into which this second composition may be placed. Alternatively, the plurality of therapeutic biologically active compositions may be prepared in a single pharmaceutical composition, and may be packaged in a single container means, such as a vial, flask, syringe, bottle, or other suitable single container means. The kits of the present invention will also typically include a means for containing the vial(s) in close confine- Exemplary Definitions In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

In accordance with long standing patent law convention, the words "a" and "an" when used in this application, including the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "effective amount," as used herein, refers to an amount that is capable of treating or ameliorating a disease or condition or otherwise capable of producing an intended therapeutic effect.

The term "for example" or "e.g.," as used herein, is used merely by way of example, without limitation intended, and should not be construed as referring only those items explicitly enumerated in the specification.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner. A patient can be of any age at which the patient is able to respond to inoculation with the present vaccine by generating an immune response. In particular embodiments, the mammalian patient is preferably human.

The phrase "pharmaceutically-acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

The term "promoter," as used herein refers to a region or regions of a nucleic acid sequence that regulates transcription.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "1" isomeric form. However, residues in the "d" isomeric form may be substituted for any 1-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present invention also include polypeptides and proteins that are or have been post-translationally modified, and include any sugar or other derivative(s) or conjugate(s) added to the backbone amino acid chain.

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described (Pearson and Lipman, 1988).

As used herein, the term "structural gene" is intended to generally describe a polynucleotide, such as a gene, that is expressed to produce an encoded peptide, polypeptide, protein, ribozyme, catalytic RNA molecule, or antisense molecule.

The term "subject," as used herein, describes an organism, including mammals such as primates, to which treatment with the compositions according to the present invention can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will be greater than about 80 percent complementary (or "% exact-match") to a corresponding nucleic acid target sequence to which the nucleic acid specifically binds, and will, more preferably be greater than about 85 percent complementary to the corresponding target sequence to which the nucleic acid specifically binds. In certain aspects, as described above, it will be desirable to have even more substantially complementary nucleic acid sequences for use in the practice of the invention, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the terms "treat," "treating," and "treatment" refer to the administration of one or more compounds (either alone or as contained in one or more pharmaceutical compositions) after the onset of clinical symptoms of a disease state so as to reduce, or eliminate any symptom, aspect or characteristic of the disease state. Such treating need not be absolute to be deemed medically useful. As such, the terms "treatment," "treat," "treated," or "treating" may refer to therapy, or to the amelioration or the reduction, in the extent or severity of disease, of one or more symptom thereof, whether before or after its development afflicts a patient.

The tern "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

As used herein, "an effective amount" would be understood by those of ordinary skill in the art to provide a therapeutic, prophylactic, or otherwise beneficial effect to a recipient patient.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardt's solution, 5×SSC, 25 mM sodium phosphate, 0.1% SDS and 100 µg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardt's solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third by to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/ detection protocols are well-known to those of ordinary skill in the molecular genetic arts.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1—Functional Role of AAV2 ITRs in polyA-Deleted mRNA Transport and Transgene Expression The genome of wild-type (WT) as well as recombinant AAV vector is flanked by two inverted terminal repeats (ITRs), one of which is located upstream of the promoter region and the other of which is located downstream of the polyadenylation (PolyA) signal. Previous studies have documented that the left ITR in promoter-deleted constructs possesses enhancer and promoter activities, but the role of the right ITR in the polyA-deleted constructs has not been examined. In the present example, it is shown that upon deletion of the conventional polyA signal from the rAAV genome, the extent of transgene expression from polyA-deleted vectors is indistinguishable from that of vectors containing an authentic polyA sequence, in the presence of AAV replication (Rep) proteins and adenoviral proteins. Furthermore, the inventors have shown that WT AAV2 genomes devoid of a conventional polyA signal undergo complete gene expression, genome replication, encapsidation, and progeny virion production. Although it remains to be seen whether polyA-deleted AAVs exist in nature, these findings identify the first eukaryotic organism that can maintain its life cycle without a conventional polyA signal and provide new insights into the roles of AAV ITRs.

Material and Methods

Cell Lines and Cultures:

HEK293, HeLa, Huh7 and K562 cell lines were purchased from American Type Culture Collection (Manassas, Va., USA) and maintained in complete DMEM media (Mediatech, Inc.) supplemented with 10% heat-inactivated fetal bovine serum (FBS, Sigma-Aldrich), 1% penicillin and streptomycin (P/S, Lonza). Cells except K562 were grown as adherent culture in a humidified atmosphere at 37° C. in 5% $CO_2$ and were sub-cultured after treatment with trypsin-versene mixture (Lonza) for 2-5 min at room temperature, washed and re-suspended in complete media. K562 were grown as suspension culture.

Plasmids:

Plasmid pAAV-hrGFP and pHelper were purchased from Agilent Technologies. Plasmid pAAV-hrGFP-AD was produced by enzyme digestion of pAAV-hrGFP with XhoI and RsrII; pAAV-hrGFP-RD by RsrII and KasI; pAAV-hrGFP- ARD by XhoI and KasI; followed by Klenow end-filling reaction, and T4 ligase-mediated self-ligation. Plasmid pdsAAV-EGFP was obtained from Dr. Xiao Xiao (University of North Carolina at Chapel Hill). Plasmid pdsAAV-EGFP-AD was produced by enzyme digestion of pdsAAV-EGFP with HindIII and BbsI, followed by Klenow end-filling reaction and T4 ligase-mediated self-ligation. Plasmid pACG2 and pRep-TAP have been previously described[10,33]. Plasmid pRena1 was produced by enzyme digestion of pACG2 with EcoNI and BspMI, followed by Klenow end-filling reaction and T4 ligase-mediated self-ligation. Plasmid pSub201 was obtained from Dr. R. Jude Samulski (University of North Carolina at Chapel Hill). The whole gene cassette was amplified by NotI site-linked primers 201AD-F and 201AD-R, as indicated below. The amplicons were digested with NotI and T4 ligase-mediated ligation with NotI-digested pAAV-hrGFP, to generate pSub201-AD. All plasmids were sequenced prior to usage.

Primers and Oligonucleotide Probes:

Primers Primer-F (5'-GCGGCCGCACGCGTCTAGTTATTA-3') (SEQ ID NO:1) and Primer-R (5'-AGAAAATACCGCATCAGGCG-3') (SEQ ID NO:2) were used to amplify the transgene cassettes depicted in FIG. 17. Primers hrGFP-F (5'-TGATCGAGGAGATGTTCGTG-3') (SEQ ID NO:3) and hrGFP-R (5'-CCGGTGATGGTCTTCTTCAT-3') (SEQ ID NO:4) were used in qPCR assays. Primer ITR (5'-TTGGCCACTCCCTCTCTGCG-3') (SEQ ID NO:5) was used in reverse transcription assays in FIG. 1. $^{32}$P-labeled oligonucleotide probes (hrGFP, 405-bp) obtained from plasmid pAAV-hrGFP following digestion with PstI; probes (PolyA, 560-bp) obtained from plasmid pAAV-hrGFP following digestion with XhoI and RsrII; probes (EGFP, 732-bp) obtained from plasmid pAAV-hrGFP following digestion with NcoI and HindIII were used for hybridization to vector genomes. Primers 201AD-F (5'-CGATGCGGCCGCTGTAGTTAATGATTA-3') (SEQ ID NO:6) and 201AD-R (5'-CGATGCGGCCGCTTACAGATTACGAGTCA-3') (SEQ ID NO:7) were used to amplify the WT AAV2 gene cassette. $^{32}$P-labeled oligonucleotide probes (Rep2Cap2, 405 bp) isolated from pSub201 by digestion with PstI were used for hybridization to the viral genomes in DNA slot-blot and Southern blot assays.

DNA Transfection Assay:

Cells were seeded in 96-well plates at a concentration of $1 \times 10^4$ cells per well in complete DMEM and incubated at 37° C. overnight before experiments. For PEI-mediated transfection, the plasmids were incubated with linear polyethylenimine (PEI, Polysciences, Inc.) at 37° C. in serum-free and antibiotic-free DMEM for 10 min. The DNA-PEI mixtures were then added into cell culture and incubated at 37° C. for 6 hrs. Cells were then washed with complete DMEM twice and incubated at 37° C. for 48 hrs. Lipofectamine- and $CaCl_2$-mediated transfections were carried out according to the manufacturer's protocol for Lipofectamine™ 2000 (Invitrogen) and ProFection Mammalian Transfection System (Promega), respectively.

Recombinant AAV Vectors:

Viral vectors were packaged using the protocol described previously (34). Briefly, HEK293 cells were co-transfected with the three plasmids in the presence of PEI to produce each of the vector stocks. Re-suspended cells were subjected to 3 rounds of freeze-thaw at 72 hrs' post-transfection, digested with Benzonase (Novage) and purified by iodixanol (OptiPrep) gradient ultra-centrifugation followed by ion exchange chromatography using HiTrap SP HP column (GE Healthcare). The physical particle titers of recombinant vector stocks were determined by quantitative DNA slot-blot analyses, qPCR assays and Southern blot as described previously[34,35].

Viral DNA Rescue and Replication Assay:

PEI-mediated plasmid transfections were carried out as described above with equivalent amounts of each of the rAAV plasmids, together with pACG2 and pHelper plasmids, in 100-mm-diameter dishes containing ~80% confluent HEK293 cells. At various times post-transfection, low molecular weight (low-$M_r$) DNA samples were isolated by the procedure described previously[33], digested extensively with DpnI, and analyzed on Southern blots using $^{32}$P-labeled DNA probes.

Viral DNA Extraction from Purified Viral Stocks:

Equivalent amounts of viral stock were digested with Benzonase at 37° C. for 1 hr in a total volume of 50 µL. An equal volume of 100 mM NaOH was added followed by incubation at 65° C. for 30 min. Viral DNA was then be purified by DNA Clean & Concentrator -25 (ZYMO Research).

Southern Blot Assay:

Viral DNA were purified as stated above and electrophoresed on 1.2% neutral or alkaline agarose gels, followed by transfer to nylon membranes. Briefly, the gel was equilibrated with Solution I (0.25 M HCl) for 20 min, Solution II (1 M NaCl, 0.5 M NaOH) for 40 min and Solution III (1.5 M NaCl, 1.5 M Tris-HCl, pH 7.4) for 40 min at RT. The DNA was transferred to Immobilon-NY+TM membranes (Millipore, Bedford, Mass., USA) in 20×SSC. The membrane were then pre-hybridized for 6 hr at 68° C. in 25 mL hybridization solution containing 6×SSC, 100 µg/mL freshly-boiled herring sperm DNA, 0.5% sodium dodecyl sulfate (SDS), and 5×Denhardt's reagent in a Fisher Isotemp vacuum oven. Subsequently, the membranes were hybridized with freshly-boiled $^{32}$P-labeled DNA probe ($6 \times 10^5$ cpm of probe per mL hybridization solution) in a total volume of 25 mL hybridization solution at 68° C. for 18-20 hr. Membranes were then washed once in 50 mL wash solution 1 (2×SSC, 0.1% SDS) at room temperature (RT) for 15 min, twice in 50 mL wash solution 2 (0.1×SSC, 0.1% SDS) at 68° C. for 30 min, and then exposed to BIOMAX MR™ X-ray films (Kodak, Rochester, N.Y., USA) at -70° C.

Recombinant AAV Vector Transduction Assay:

Cells were seeded in 96-well plates at a concentration of $1 \times 10^4$ cells per well in complete DMEM and incubated at 37° C. overnight before experiments. Adherent cells were washed twice with serum-free and antibiotic-free DMEM (F-DMEM) and then infected at 37° C. for 2 hrs with rAAV2 vectors in F-DMEM. Cells were then washed with complete DMEM twice and incubated at 37° C. for 72 hrs. The expression of GFP was analyzed either by flow cytometry or by direct fluorescence imaging 72 hrs post-transduction by ImageJ analysis software (National Institutes of Health, Bethesda, Md., USA). Transgene expression was assessed as total area of green fluorescence (pixel$^2$) per visual field (mean±SD) for ImageJ.

Cell Compartment Fraction:

Nuclear and cytoplasmic fractions from cells were isolated as described previously (36). Briefly, cell pellets were gently resuspended in 175 µL pre-cooled RLN buffer (50 mM Tris.HCl, pH 8.0; 140 mM NaCl; 1.5 mM $MgCl_2$ and 0.5% Nonidet P-40). The samples were vortexed vigorously for 10 sec. and incubated on ice for 5 min. This was followed by centrifugation at 300×g for 2 min. The supernatant was collected as the cytoplasmic fraction and the pellet as the nuclear fraction. Purity of cellular fractions was assayed by Western blot analysis using the following antibodies from Santa Cruz Biotechnology and appropriate secondary antibodies: anti-IκB polyclonal Ab (C-21) and anti-Lamin B polyclonal Ab (C-20).

Western Blot Assay:

Western blot analyses were performed as described previously (37). Briefly, Cells were harvested and disrupted in a radio-immunoprecipitation assay (RIPA) lysis buffer (50 mM Tris-HCl, pH 8.0, 150 mM NaCl, 0.1% SDS, 1% NP-40, 0.25% sodium deoxycholate and 1 mM EDTA with protease inhibitor cocktail, 1 mM NaF and 1 mM $Na_3VO_4$). Total protein concentration was measured using a Bradford reagent (Bio-Rad, Hercules, Calif., USA). Following normalization for protein concentration, samples were separated using 12% SDS-PAGE electrophoresis, electro-transferred to a nitrocellulose membrane (Bio-Rad), and probed with relevant primary antibodies at 4° C. overnight. The membranes were then incubated with horseradish peroxidase-conjugated secondary antibodies (GE Healthcare, Cat#NA931, 1:5000 dilution), and detected with an enhanced chemi-luminescence substrate (MEMD Millipore, Cat#WBKLS0100). All membranes were stripped and re-probed with anti-GAPDH antibody as a loading control. Antibody against Rep proteins (monoclonal 1F) was provided by Dr. Nicholas Muzyczka (University of Florida). Antibody against GAPDH (polyclonal) was purchased from Thermo Scientific, Cat#PA1-988. Antibody against TAP-tag (polyclonal) was purchased from GenScript, Cat#A00683-40. Antibodies against IκB (polyclonal, C-21) and Lamin B (polyclonal, C-20) were purchase from Santa Cruz Biotechnology.

RNA Isolation, Reverse Transcription and qPCR Assays:

Total RNA from either whole cells, nuclear or cytoplasmic fractions was extracted with the RNeasy Mini Kit (QIAGEN, Cat#79254) and reverse transcribed using Reverse Transcription System (Promega, Cat#A3500) according to the manufacturer's protocol. Real-time qPCR amplification was carried out using SYBR GreenE qPCR SuperMix for iCycler (Invitrogen, Cat#11761) according to the manufacturer's instructions. Intact total RNAs were indicated by sharp 28S and 18S rRNA bands on a neutral agarose gel.

Structure Prediction:

The ITR DNA sequence and the RNA sequence were evaluated for secondary structure prediction using the mFOLD webserver software utilizing the DNA or RNA Folding Forms (38). A model of AAV2 Rep78 was generated using the software Swiss Model and the amino acid sequence of AAV2 Rep78. The AAV2 Rep78 model was based on the crystal structure of AAV5 Rep78, PDB Accession#1m55 and includes amino acids 1 to 193[40]. The model for the AAV2 DNA sequence that comprises the Rep Binding Sequence (RBS) was produced using the software nucleic acid builder, utilizing the make-na server. The software WinCoot was utilized to generate the AAV2 Rep DNA model, as well as the AAV2 Rep RNA model[41]. The software PyMOL, version 1.5.0 was utilized to generate the images of the AAV2 Rep DNA model and the AAV2 Rep RNA models.

Statistical Analysis:

Results are presented as mean±standard deviation (SD). Differences between groups were identified using a grouped-unpaired two-tailed distribution of Student's T test. P values <0.05 were considered statistically significant.

Figure 16A:
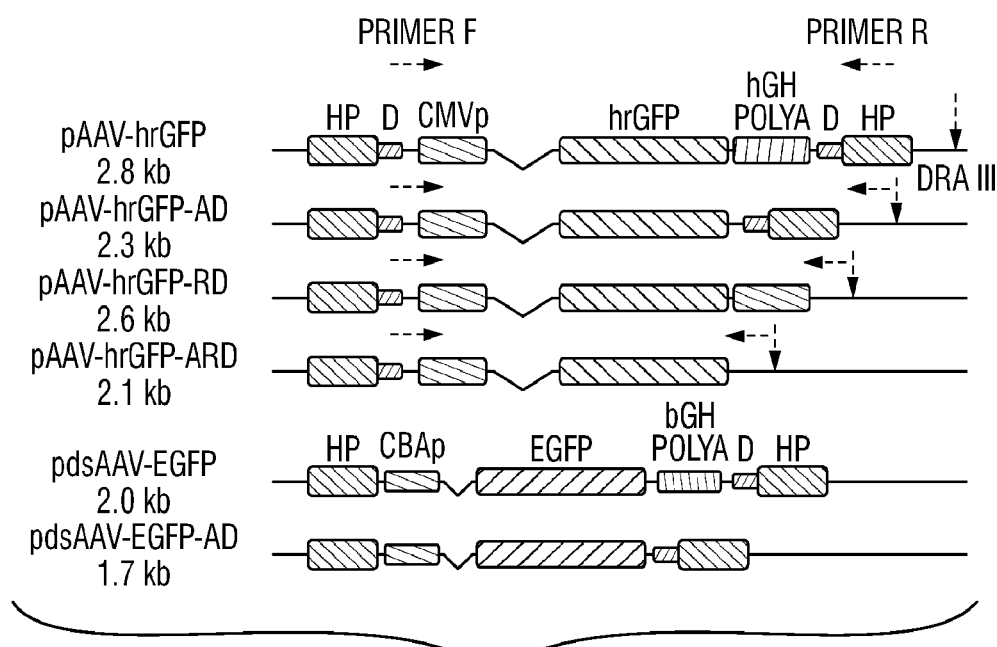

Supplementary Methods:

Recombinant AAV plasmids containing polyA-deleted transgene cassettes express detectable levels of protein products. The following recombinant plasmids were generated from a commercially available plasmid pAAV-hrGFP carrying the humanized green fluorescence protein (hrGFP) driven by the cytomegalovirus promoter (CMVp), and containing the human growth hormone (hGH) polyA signal (FIG. 16A): (i) pAAV-hrGFP-AD, in which the polyA sequence was deleted; (ii) pAAV-hrGFP-RD, in which the AAV right ITR was deleted; and (iii) pAAV-hrGFP-ARD, in which both polyA and the right ITR sequences were deleted. When each of these plasmids were transfected into HEK293 cells, robust transgene expression occurred from the parent plasmid (pAAV-hrGFP) as well as that from which the right ITR was deleted (pAAV-hrGFP-RD) (FIG. 16B, left panel). Surprisingly, however, detectable levels of transgene expression also occurred from the plasmids that lacked the polyA sequence (pAAV-hrGFP-AD), suggesting a minimal polyA-like function mediated by the right ITR. Similar results were obtained when the plasmids were linearized following digestion with DraIII (FIG. 16B, middle panel), or the PCR-amplified DNA products of the expression cassettes from each plasmid (FIG. 16B; right panel). Thus, it was concluded that AAV2 right ITR, in its linear, double-stranded DNA configuration, mediates detectable levels of transgene expression from a polyA-deleted cassette, at ~5 to 10% of that with a conventional hGH polyA sequence.

Substantial protein expression is mediated by the polyA-deleted transgene cassette in the presence of WT AAV2 and adenoviral genes. To examine whether the WT AAV2 or adenovirus early genes could facilitate transgene expression from the polyA-deleted cassettes, PCR amplicons from the three plasmids were transfected into HEK293 cells, with or without plasmids containing the WT AAV2 rep and cap genes (pACG2)[23], and adenoviral E2a, E4orf6 and VA RNA genes (pHelper). The presence of adenoviral genes enhanced transgene expression from each cassette (FIG. 16C), most likely due to augmented transcription and mRNA export. Interestingly, in the presence of AAV2 rep and cap genes, the levels of transgene expression from cassettes lacking the polyA sequence, or both polyA and the ITR sequences, were approximately the same as that from the intact transgene cassette containing a conventional hGH polyA sequence (FIG. 16C).

To further define the role of adenoviral E1a and E1b genes, which are constitutively expressed in HEK293 cells, the same experiments were also conducted in HeLa cells, and similar results were observed. To further substantiate these results, a second polyA-deleted plasmid (pdsAAV-EGFP-AD) was developed from its parent plasmid pdsAAV-EGFP (FIG. 16A), which contains the enhanced green fluorescence protein (EGFP) driven by the chicken beta-actin/CMV hybrid promoter (CBAp). Following transfections of these plasmids in HEK293 cells, the pACG2 and pHelper plasmid-mediated augmentation of transgene expression mediated by both AAV plasmids was readily evident (FIG. 16D). When HeLa cells were mock-transfected, or transfected with pAAV-hrGFP, pAAV-hrGFP-AD, or pAAV-hrGFP-RD plasmids, in the presence of pACG2 and co-infection with adenovirus, similar percentage of cells were GFP-positive, as determined by FACS analysis (FIG. 16E), corroborating that the presence of both WT AAV2 and adenoviral genes significantly enhances transgene expression in each individual cell.

PolyA-deletion does not affect rAAV genome rescue, replication, and vector production. rAAV DNA rescue and replication assays from recombinant plasmids pAAV-hrGFP and pAAV-hrGFP-AD revealed that deletion of the hGH polyA site had no effect on viral genome rescue and replication, as determined by time-dependent accumulation of the monomeric (m) and dimeric (d) forms of AAV DNA replicative intermediates following Southern blot analyses (FIG. 17A), using both hrGFP (left panel) and polyA (right panel) probes. However, deletion of the right ITR completely blocked viral genome rescue and replication (FIG. 17A). Following rescue and replication from plasmids pAAV-hrGFP and pAAV-hrGFP-AD, the viral genomes were successfully packaged into viral capsids at approximately similar titers, as determined by quantitative DNA slot-blots (FIG. 17B). The vector titers generated following three independent production runs, as determined by quantitative PCR (qPCR) are shown in Table 1. A slight overall increase in the titers of the polyA-deleted vectors most likely reflects the relatively shorter length of the vector genome. Southern blot analyses following both neutral and alkaline agarose gel electrophoresis (FIG. 17C) revealed that both single-stranded (ss) AAV genomes migrated at the expected positions using the CMV probe (two left panels), whereas no signal was observed with polyA-deleted vectors using the polyA probe (two right panels). Similar results were obtained with self-complementary (sc) AAV vectors (FIG. 17D). Furthermore, SDS-polyacrylamide gel electrophoresis followed by silver staining revealed the presence of similar levels viral structural proteins VP1, VP2 and VP3, roughly at the same ratio of 1:1:10 in both vector stocks.

TABLE 1

TITERS OF SSAAV2-HRGFP AND SSAAV2-HRGFP-AD VECTORS

| rAAV vectors | Vector Titers (vgs/mL) | | | |
|---|---|---|---|---|
| | Expt. #1 | Expt. #2 | Expt. #3 | Mean ± SD |
| ssAAV2-hrGFP | $2.7 \times 10^{11}$ | $2.0 \times 10^{11}$ | $3.9 \times 10^{11}$ | $2.8 \times 10^{10} \pm 9.7 \times 10^{10}$ |
| ssAAV2-hrGFP-AD | $5.3 \times 10^{11}$ | $3.9 \times 10^{11}$ | $2.4 \times 10^{11}$ | $3.9 \times 10^{11} \pm 1.4 \times 10^{11}$ |

Titers of the polyA-containing (ssAAV2-hrGFP) and polyA-deleted (ssAAV2-8 hrGFP-AD) vectors generated by three separate packaging runs (Expts. #1, #2, and #3). Each packaging run was carried out by using ten 150-mm culture dishes for each vector. Vector titers were determined by qPCR assays. Data are represented as Mean±SD.

Results

The Presence of 3'-End ITR Sequence in mRNA Produced by polyA-Deleted rAAV2 5 Vectors.

The following two polyA-deleted rAAV2 vectors were generated (FIG. 2A): (i) a single-stranded (ss) AAV2-hrGFP-AD, derived from a commercially available vector, ssAAV2-hrGFP, carrying a humanized recombinant green fluorescence protein (hrGFP) driven by the cytomegalovirus promoter (CMVp), and the human growth hormone (hGH) polyA signal, and (ii) a self-complementary (sc) AAV2-EGFP-AD, generated from its parent vector scAAV2-EGFP, which contains the enhanced green fluorescence protein (EGFP) driven by the chicken β-actin/CMV hybrid promoter (CBAp) and the bovine growth hormone (bGH) polyA signal.
There is no polyA signal (5'-AATAAA-3'; SEQ ID NO: 13)-like sequence within the ITR. Southern blot analysis revealed that deletion of the hGH polyA signal had no effect on viral genome rescue and replication, as determined by time-dependent accumulation of the monomeric (m) and dimeric (d) forms of rAAV DNA replicative intermediates (FIG. 17A), using either hrGFP- (left panel) or polyA- (right panel) probes. The viral genomes were also successfully packaged into viral capsids at approximately similar titers, as determined by quantitative DNA slot-blots (FIG. 17B). The vector titers generated following three independent production runs, as determined by quantitative PCR (qPCR) are shown in Table 1. A slight overall increase in the titers of the polyA-deleted vectors most likely reflects the relatively shorter length of the vector genome. Southern blot analyses following both neutral and alkaline agarose gel electrophoresis (FIG. 17C) revealed that both ssAAV2 and ssAAV2-AD genomes migrated at the expected positions using the CMV probe (two left panels), whereas no signal was observed with polyA-deleted vectors using the polyA probe (two right panels). Similar results were obtained with scAAV2 and scAAV2-AD vectors (FIG. 17D). Furthermore, SDS-polyacrylamide gel electrophoresis followed by silver staining revealed the presence of similar levels of viral structural proteins VP1, VP2 and VP3, roughly at the same ratio of 1:1:10 in all vector stocks (data not shown).

Figure 2F:
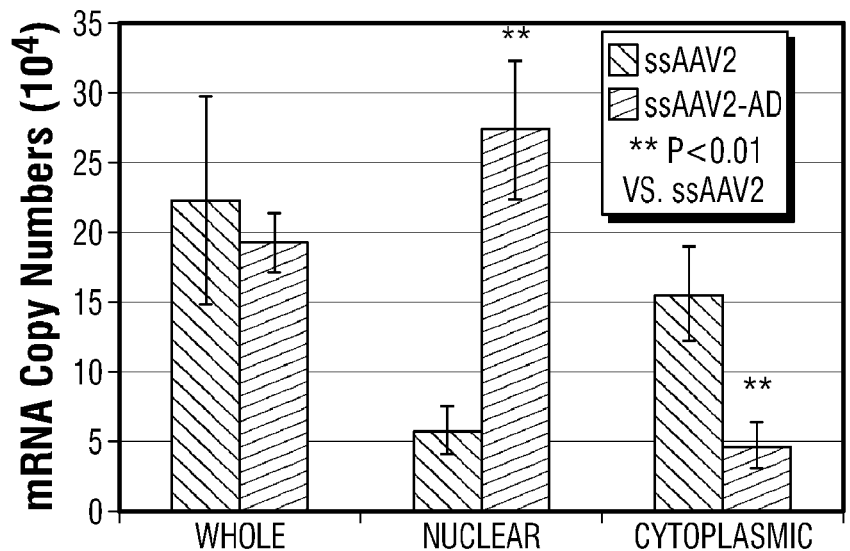
Figure 2G:
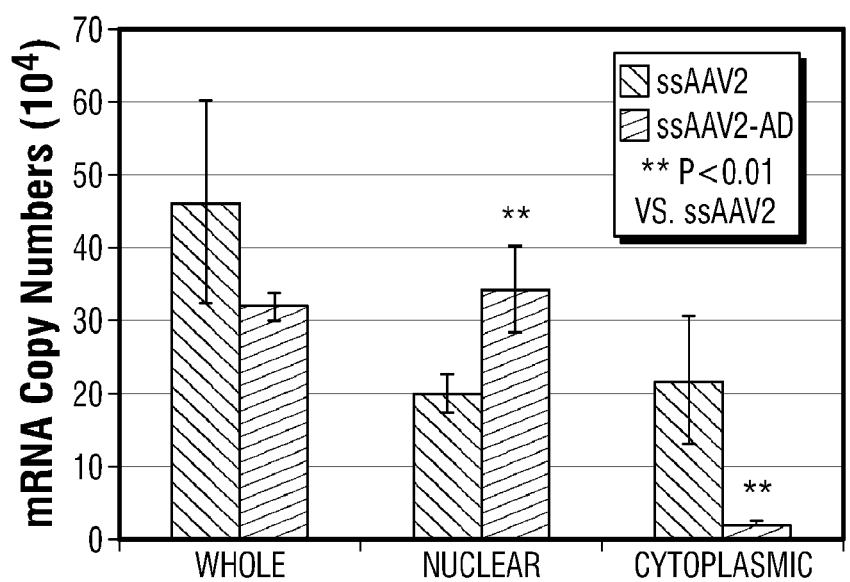
Figure 11:
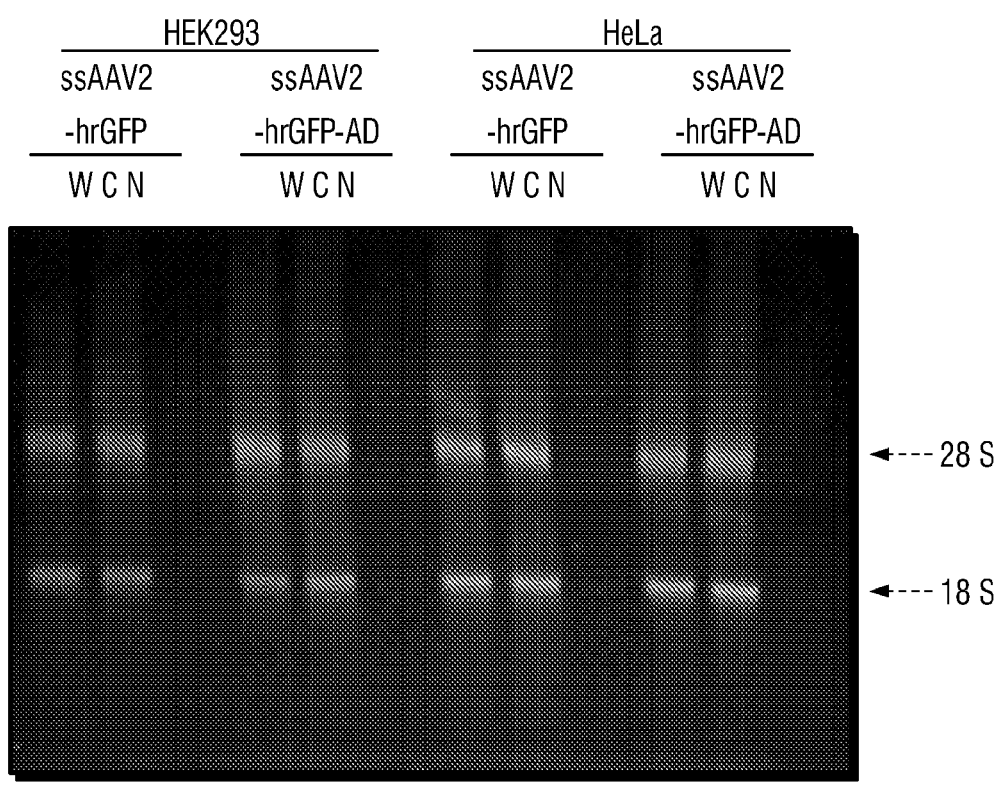
FIG. 11 shows ethidium bromide-stained neutral agarose gel electrophoresis of total RNA, indicating sharp bands of 18S and 28S ribosomal RNA. W: whole cell extracts; N: nuclear fraction; C: cytosolic fraction.
Figure 12A:
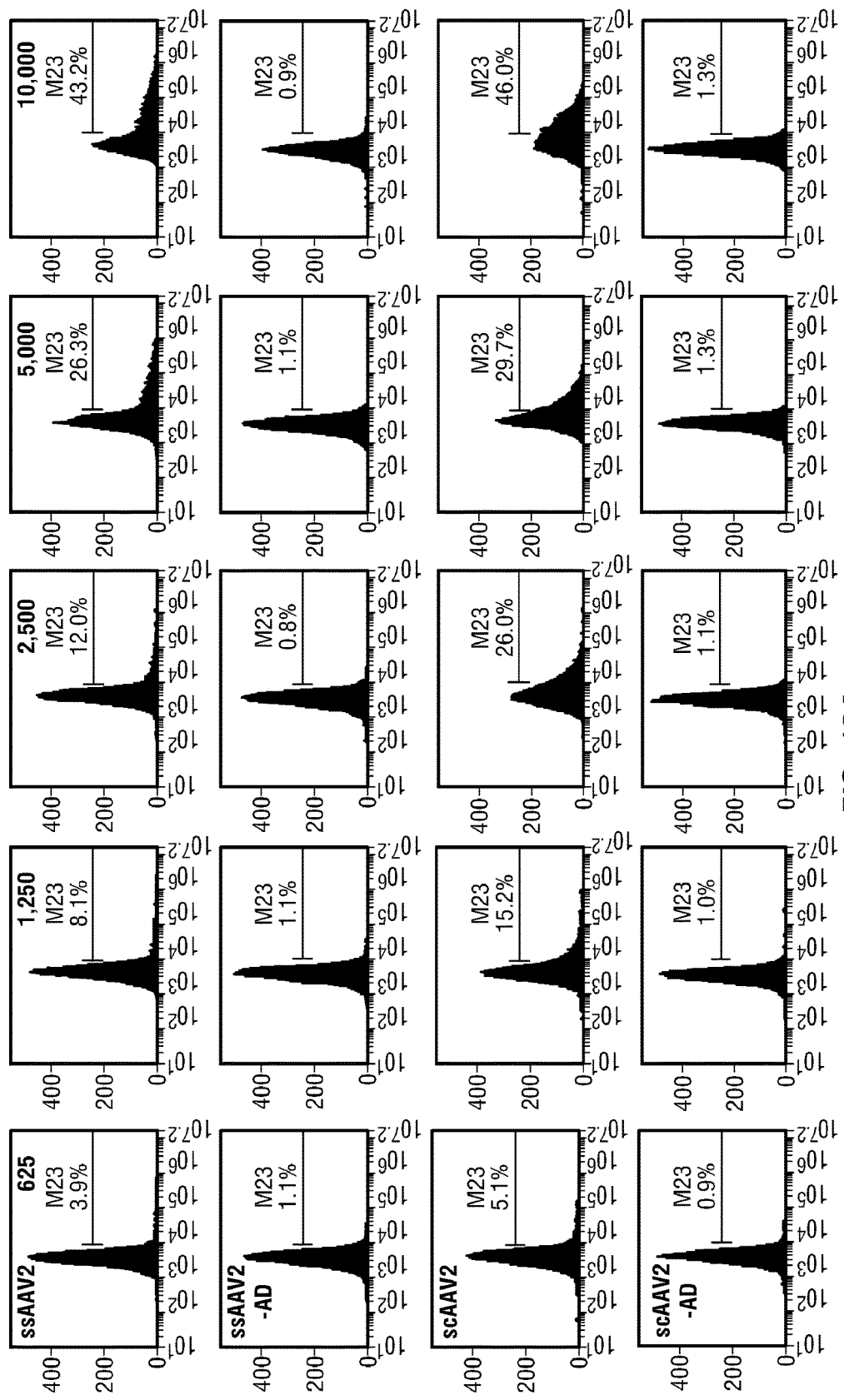
FIG. 12A and FIG. 12B shows the flow cytometric analysis of transgene expression following rAAV2 vector transduction. HEK293 (FIG. 12A) or HeLa (FIG. 12B) cells were transduced with increasing MOIs of the indicated rAAV2 vectors under identical conditions and transgene expression was determined 72 hrs post-transduction. For each sample, $8 \times 10^3$ cells were analyzed. The percentages of GFP-positive cells are indicated in red.
Figure 12B:
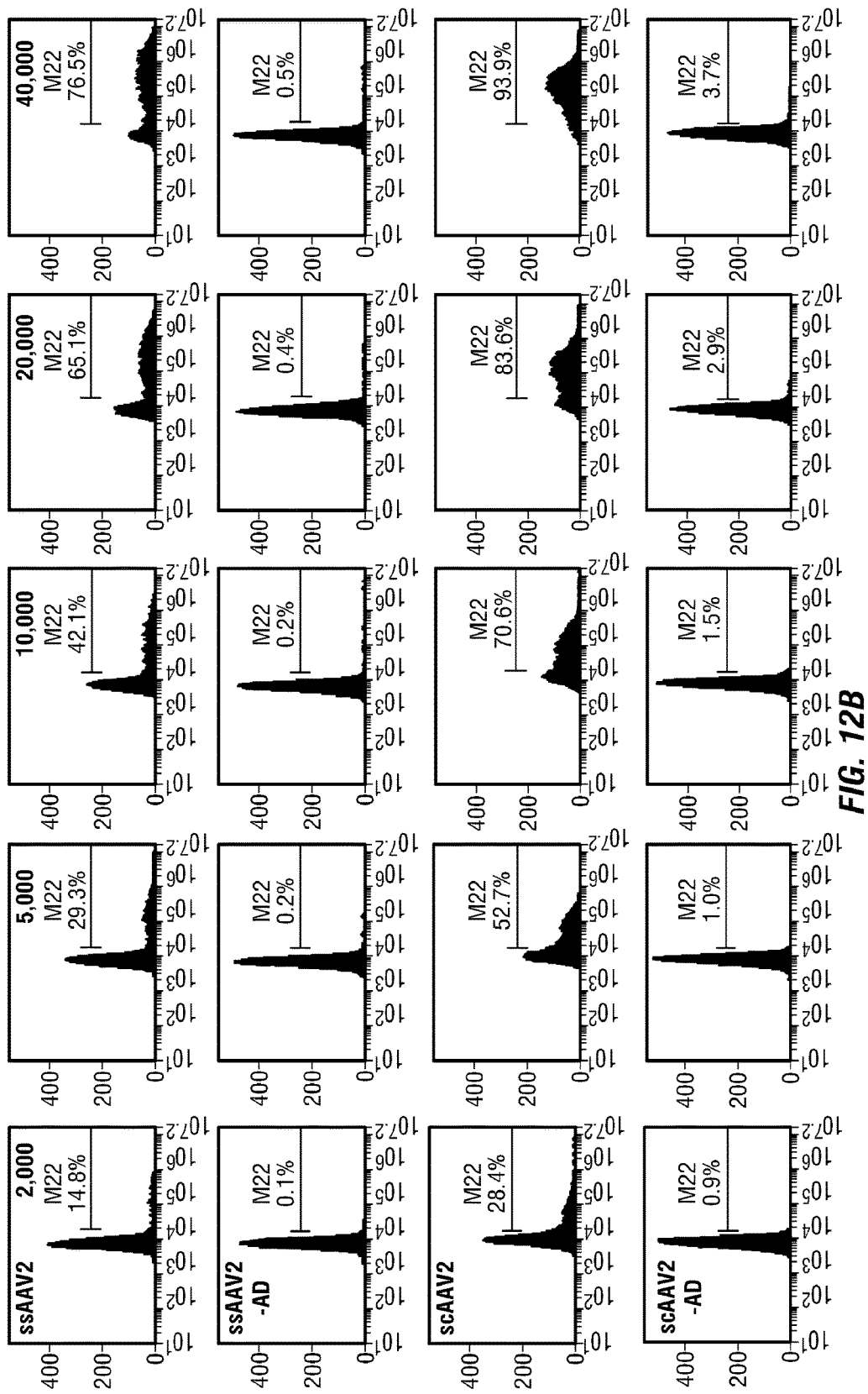

To examine whether the right ITR is transcribed as part of the mRNA, both HEK293 and HeLa cells were transduced with either ssAAV2-hrGFP or ssAAV2-hrGFP-AD vectors. Total RNAs were isolated 24 hrs' post-transduction, and reverse transcribed using primers specific for the terminal A-sequence in the viral ITR. The results of qPCR assays (FIG. 2B, +RTase) revealed that in both cell types, the mRNA transcripts derived from ssAAV2-hrGFP-AD vectors contained the whole ITR sequence. Surprisingly, a small fraction of transcripts produced by ssAAV2-hrGFP vectors also contained these sequences. No mRNA transcripts could be detected in these assays in the absence of reverse transcriptase (FIG. 2B, −RTase), ruling out the presence of contaminating viral DNA in total RNA samples. As controls, total RNAs were reverse transcribed using either random primers or oligo-d(T) primers, followed by qPCR analyses. β-actin mRNA was used as an appropriate control. The use of random primers (FIG. 2C) clearly demonstrated that in either cell type, both vectors expressed similar levels of mRNAs. On the other hand, the use of oligo-d(T) primers (FIG. 2D) allowed the detection of mRNAs expressed from ssAAV2-hrGFP vectors, but not from ssAAV2-hrGFP-AD vectors, indicating that the transcripts generated by the latter contained no polyA tails. To explore the intra-cellular distribution of mRNA, HEK293 and HeLa cells were transduced with ssAAV2-hrGFP or ssAAV2-hrGFP-AD vectors and total RNAs were isolated from whole cells (W), or cytoplasmic (C) and nuclear (N) fractions. Intact RNAs were indicated by the presence of sharp 28S and 18S rRNA bands electrophoresed on neutral agarose gels (FIG. 11), and proteins extracted from each fraction analyzed on Western blots validated the purity of cytoplasmic and nuclear fractions (FIG. 2E). Reverse transcription using random primers, followed by qPCR assays, shown in FIG. 2F and FIG. 2G, revealed that mRNAs transcribed from ssAAV2-hrGFP vectors were successfully transported into the cytoplasm, whereas mRNA transcripts produced by ssAAV2-hrGFP-AD vectors accumulated predominantly in the nucleus in both cells.

Protein Translation Mediated by polyA-Deleted rAAV2 Vectors.

Figures 1, 13A:
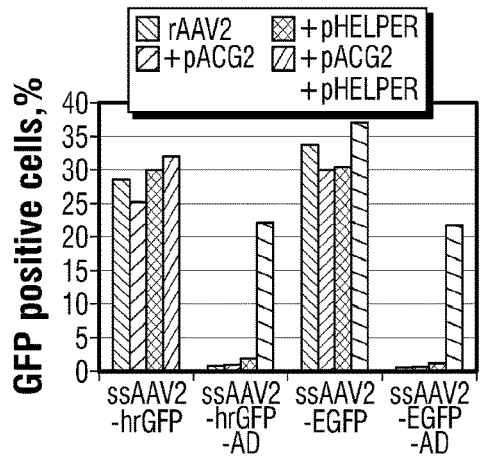
FIG. 13A, FIG. 13B, FIG. 13C, FIG. 13D, and FIG. 13E illustrate rAAV2 vector-mediated transgene expression in the presence of pACG2 and pHelper plasmids.
Figures 2, 13A:
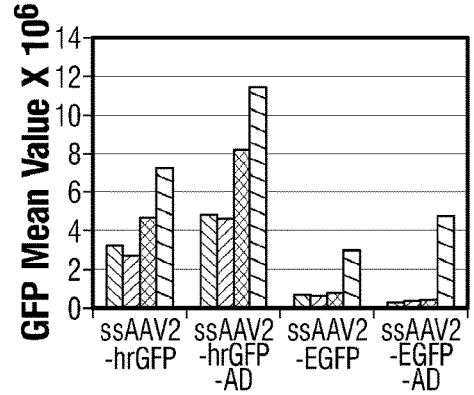
Figure 13B:
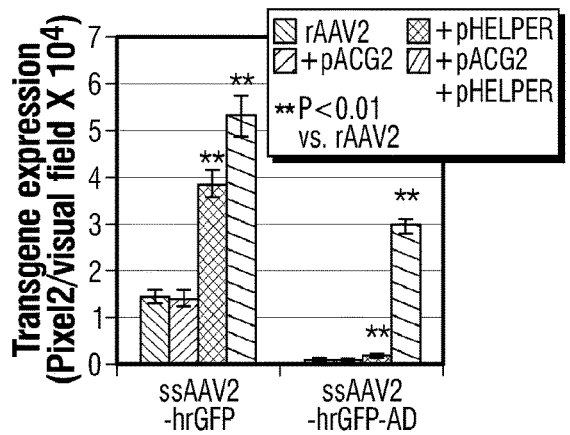
Figures 1, 13C:
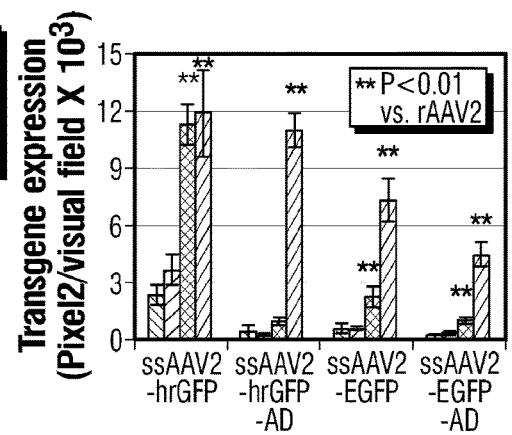
Figures 2, 13C:
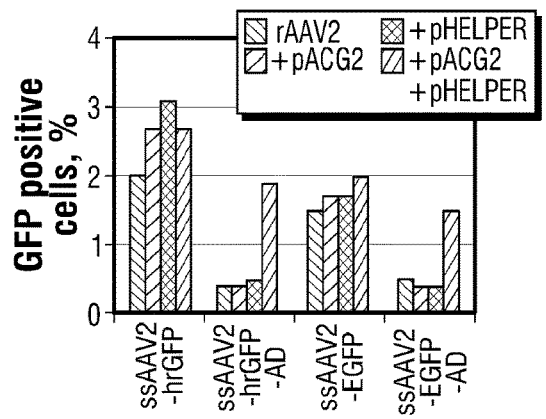
Figures 3, 13C:
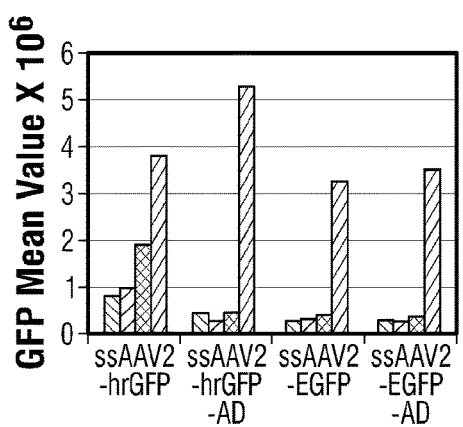
Figure 13D:
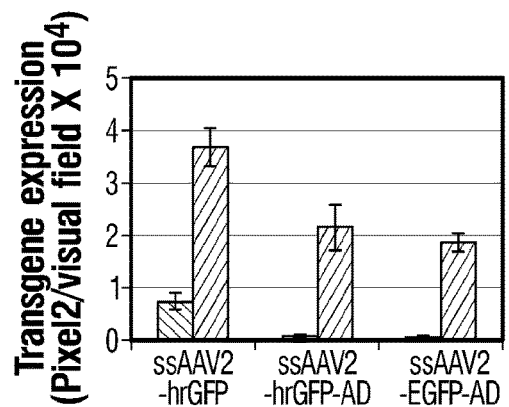
Figures 1, 13E:
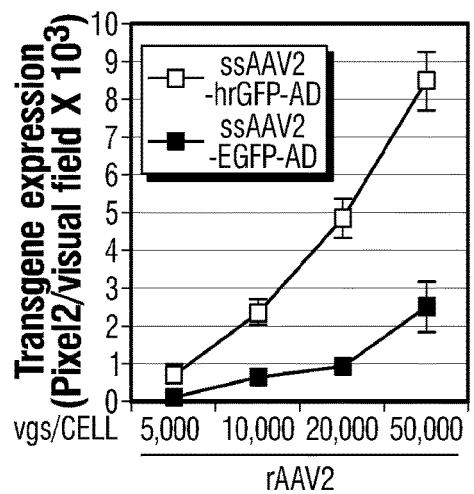
Figures 2, 13E:
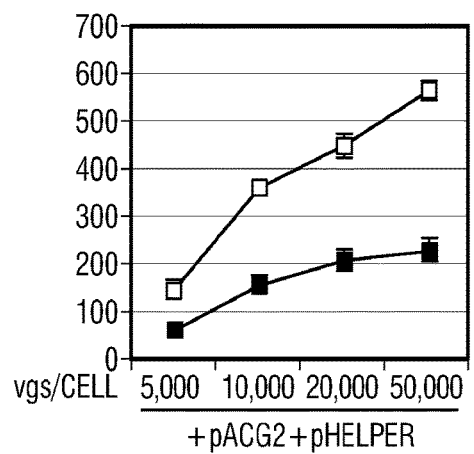

A panel of human cell lines was transduced with both sets of polyA-containing and polyA-deleted ssAAV2 and scAAV2 vectors at a multiplicity of infection (MOI) of 2,000 vector genomes (vgs)/cell. As shown in FIG. 3A, the use of both conventional ssAAV2-hrGFP and scAAV2-EGFP vectors resulted in robust transgene expression 72 hrs post-transduction as expected, but transgene expression was also detectable in cells transduced with both polyA-deleted rAAV2 vectors. To rule out any possible effect of the vector dose (42), a series of experiments was also performed using various vector MOIs, ranging from 625 to 40,000 vgs/cell. The flow cytometry data, shown in FIG. 13A and FIG. 13B, demonstrated that both ssAAV2-hrGFP and scAAV2-EGFP vectors led to a dose-dependent increase in both the percentage of GFP-positive cells and the GFP mean value in each positive cell, and although the transgene expression mediated by both polyA-deleted ssAAV2 and scAAV2 vectors was restricted to a limited number of cells, the mean value of each GFP-positive cell increases correlated with increase in the of M.O.I, which corroborated these results.

Figure 14A:
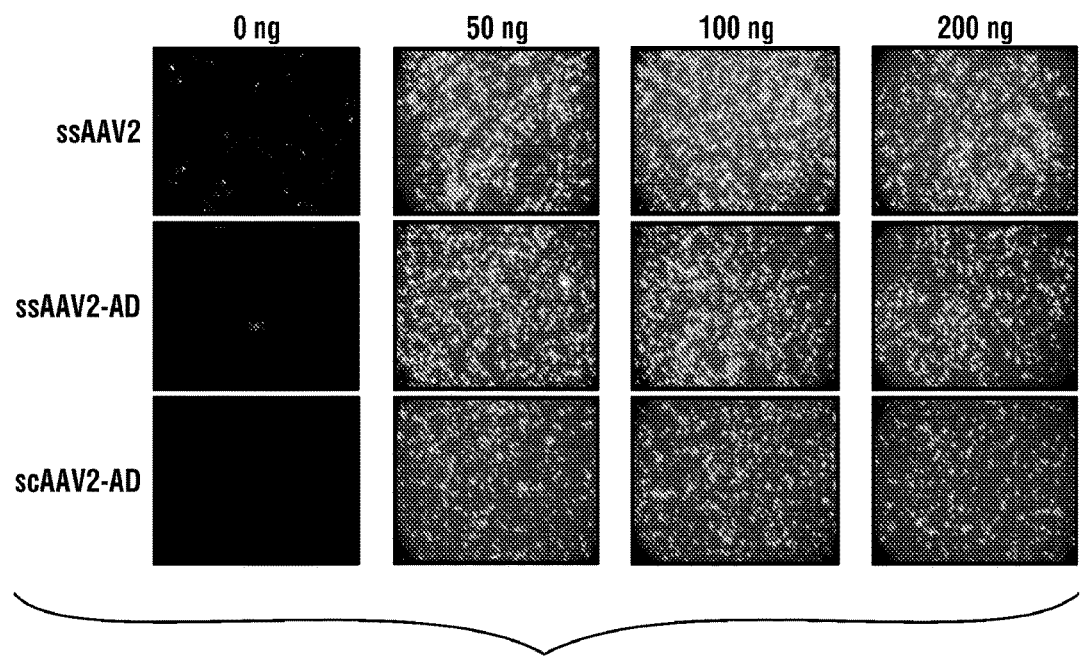
FIG. 14A, FIG. 14B, and FIG. 14C show rAAV2 vector-mediated transgene expression in the presence of pACG2 and pHelper plasmids.

It was hypothesized that the WT AAV2 genes (rep and cap) and adenoviral early genes (E2a, E4orf6, VA RNAs) may restore transgene expression mediated by polyA-deleted rAAV2 vectors. To this end, HEK293 cells were transduced with both polyA-containing and polyA-deleted ssAAV2 or scAAV2 vectors, with or without co-transfection with pACG2 and pHelper plasmids. As shown in FIG. 3B, the presence of WT AAV2 and adenoviral genes dramatically enhanced transgene expression mediated by both polyA-deleted rAAV2 vectors to levels similar to that mediated by polyA-containing rAAV2 vectors. The detailed quantitation of the data, shown in FIG. 3C, revealed that transfection with plasmid pACG2 alone had no significant effect; pHelper alone modestly increased transgene expression; and co-transfection with pACG2 and pHelper plasmids dramatically enhanced transgene expression mediated by both polyA-deleted rAAV2 vectors. Flow cytometry analyses revealed that not only the percentage of GFP-positive cells (left panel), but also the GFP mean value (right panel) in each positive cell were significantly enhanced in the presence of pACG2 and pHelper plasmids (FIG. 14A).

Figures 1, 3E:
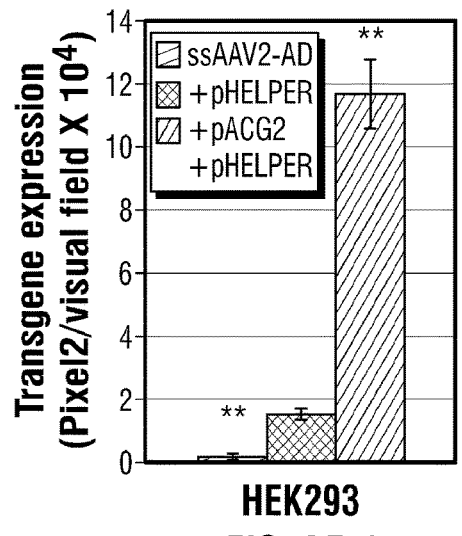
Figures 2, 3E:
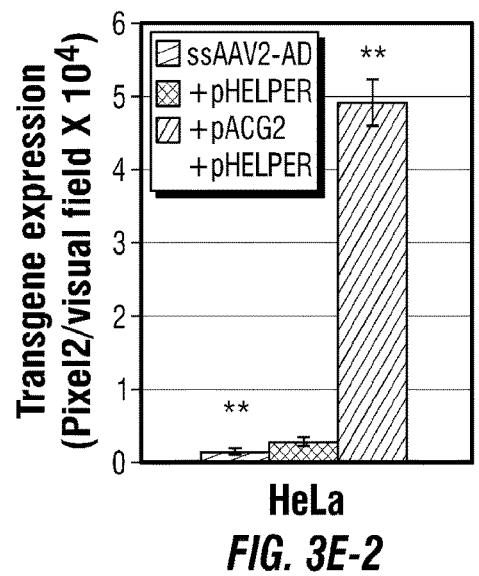
Figures 3, 3E:
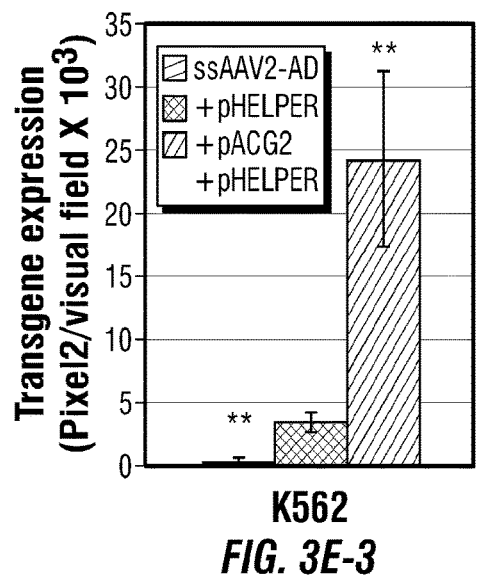
Figures 3, 3E, 4:
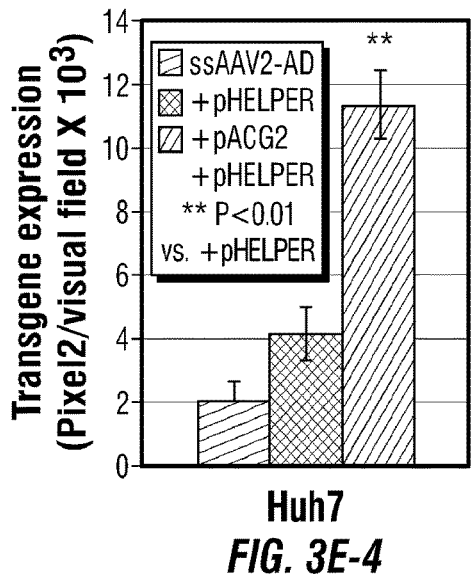
Figure 14B:
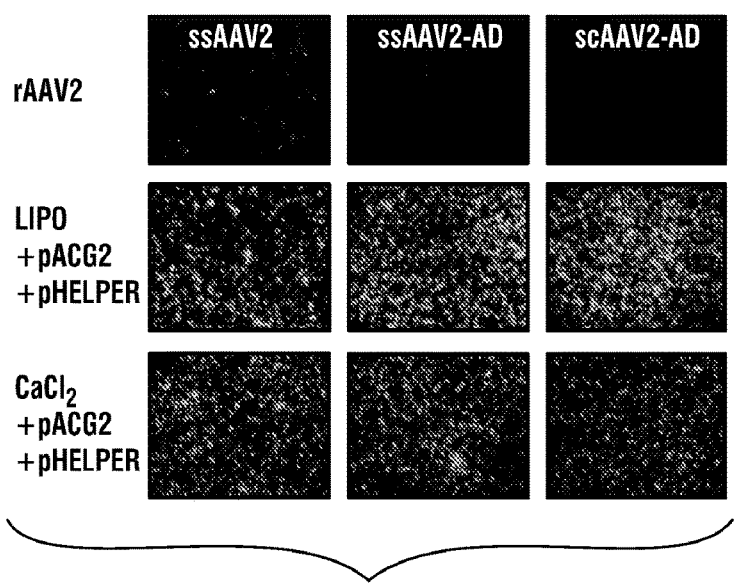
Figure 14C:
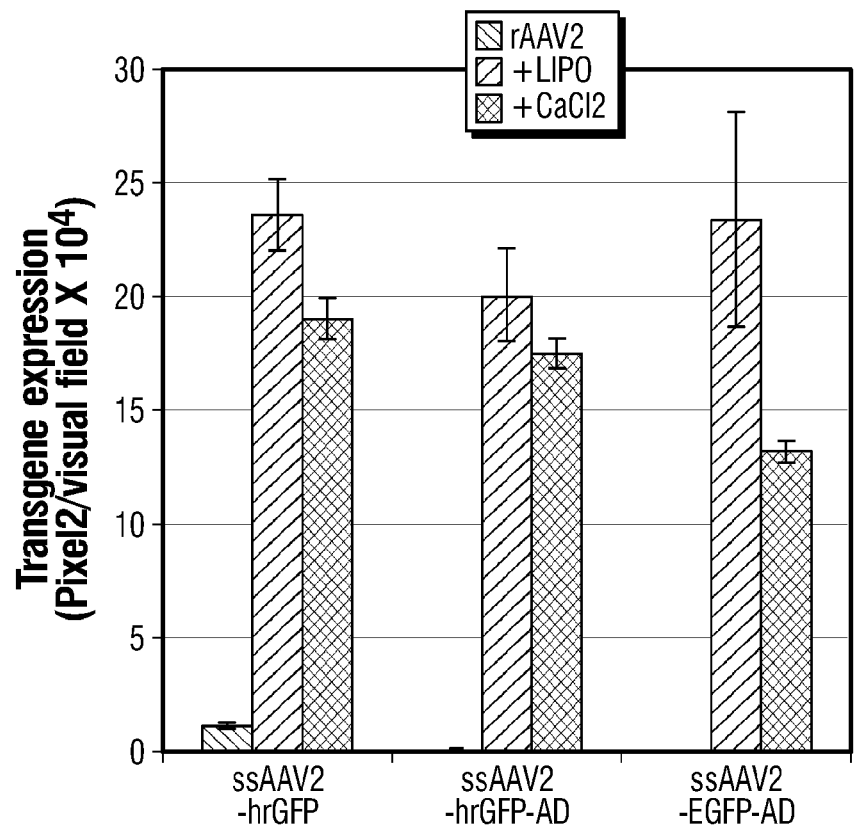
Figure 15A:
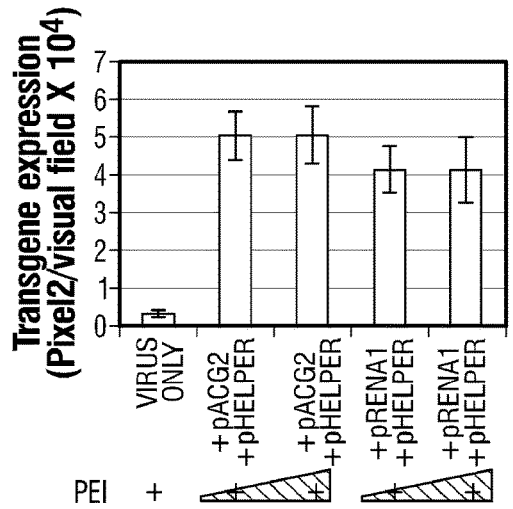
FIG. 15A, FIG. 15B, FIG. 15C, FIG. 15D, FIG. 15E, FIG. 15F, and FIG. 15G show the role of AAV Rep genes in cytoplasmic transport and translation from poly-A deleted rAAV2 mRNA transcripts.
Figure 15B:
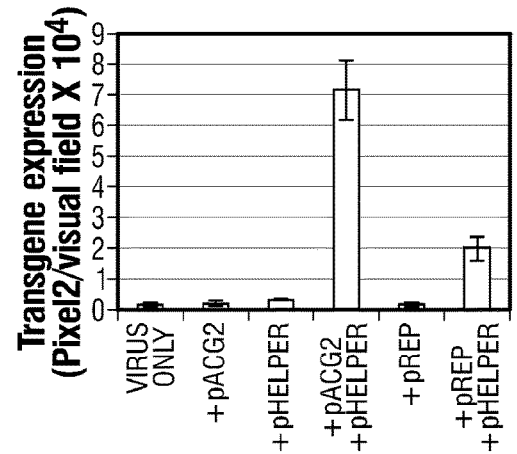
Figure 15C:
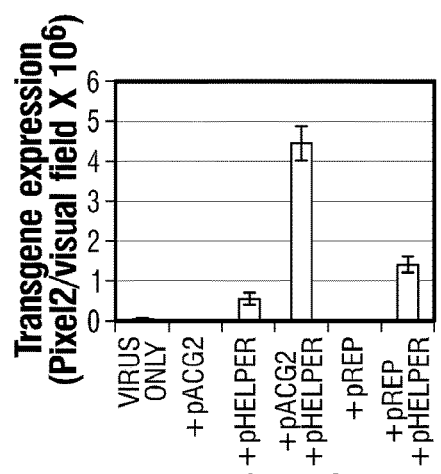
Figure 15D:
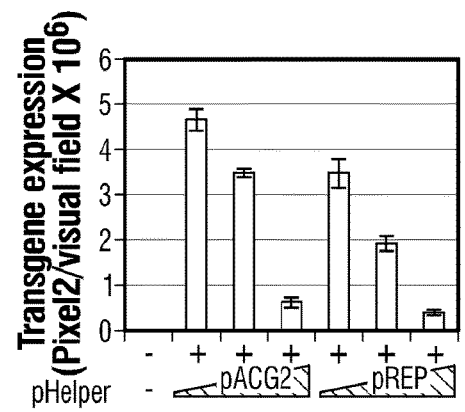
Figure 15E:
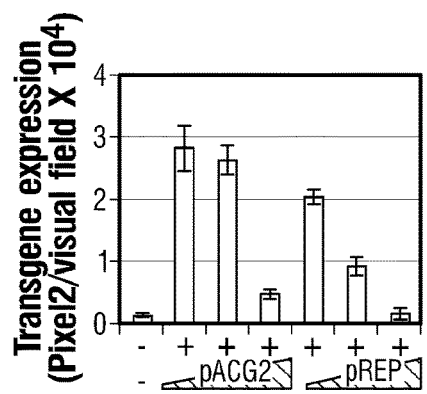
Figure 15F:
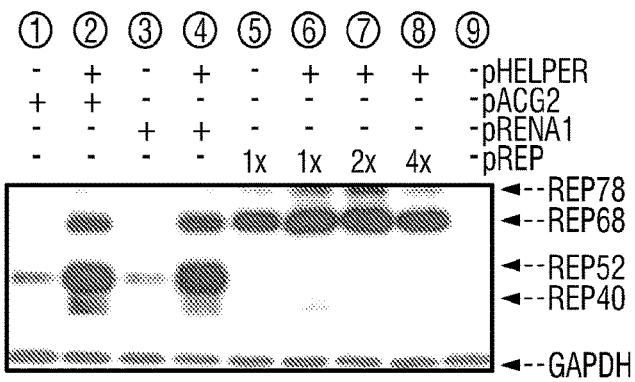
Figure 15G:
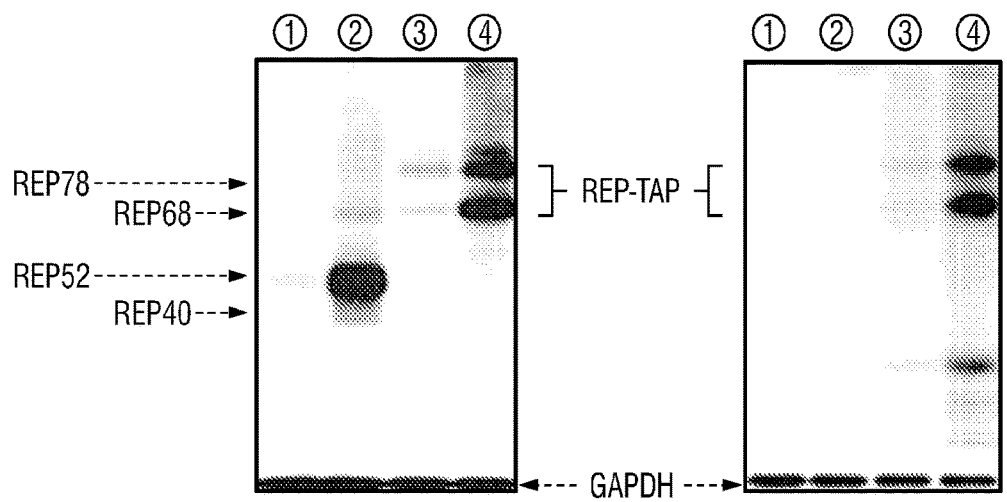

Similar results were obtained when pACG2 and pHelper plasmids were transfected 48 hrs post-transduction with rAAV2 vectors (FIG. 14B), and at low M.O.I. (FIG. 14C). The use of HeLa cells also yielded similar results (FIG. 14D). The extent of transgene expression from both polyA-containing and polyA-deleted AAV2 vectors was also determined as a function of time and MOI. As can be seen in FIG. 3D, the helper function of WT AAV2 and adenoviral genes could be observed as early as 24 hrs post-transfection of plasmids, a time-point consistent with when these proteins are expected to be expressed. It is also evident that the extent of transgene expressions correlated with the vector MOI. (FIG. 14E). Interestingly, however, the extent of transgene expression did not correlate with increasing amounts of plasmids transfected into HEK293 cells (FIG. 15A). The use of two additional transfection methods, Lipofectamine 2000 and calcium phosphate, yielded similar results (FIG. 15B and FIG. 15C). Most importantly, the enhancing effect of pACG2 and pHelper plasmids was observed in four different human cell lines: HEK293 (embryonic kidney), HeLa (cervical carcinoma), K562 (myelogenous leukemia), and Huh7 (hepatocellular carcinoma) (FIG. 3E). Thus, it was concluded that the WT AAV2 and adenovirus early gene products are capable of restoring the extent of transgene expression from polyA-deleted vectors similar to that from their polyA-containing counterparts. Furthermore, data using scAAV2 vectors suggested that such restoration of transgene expression is independent of the formation of viral double-stranded genomes.

WT AAV2 and Adenoviral Helper Function-Independence of Viral Genome Replication.

Figure 4A:
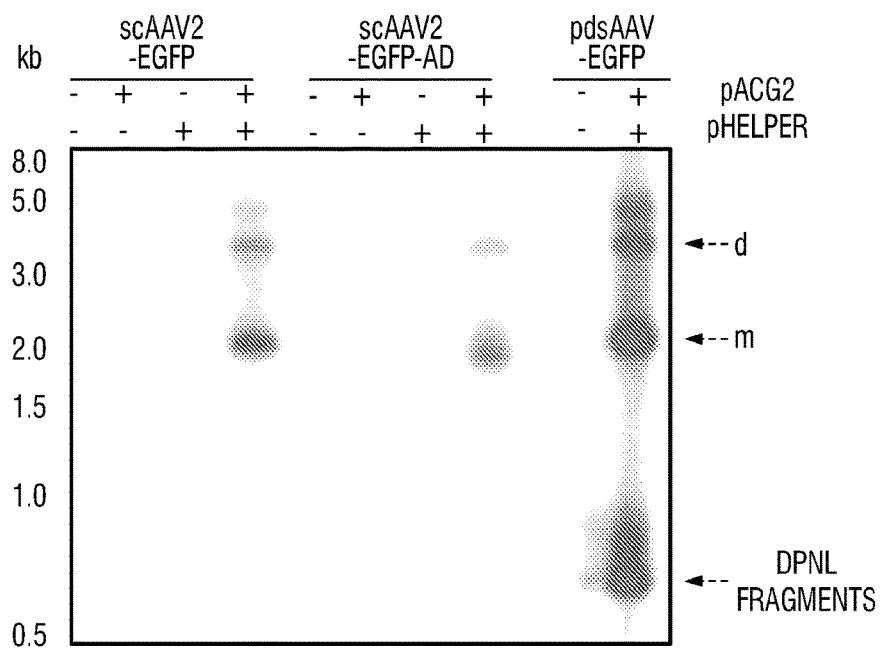
FIG. 4A and FIG. 4B show Southern blot analysis of rAAV2 viral genome replication.
Figure 4B:
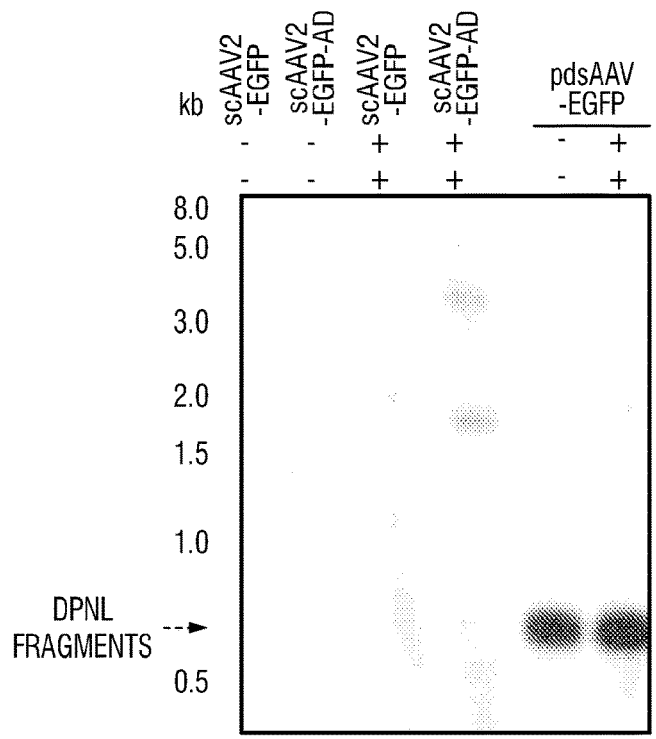

To examine the possibility that the observed increase in transgene expression from polyA-deleted rAAV2 vectors by AAV2 Rep and adenoviral proteins was due to viral genome replication, systemic studies were performed using both HEK293 and HeLa cells, taking advantage of the fact that HeLa cells do not express adenoviral E1a and E1b genes, which are essential for AAV genome replication. DNA replication assays showed that both polyA-containing and polyA-deleted rAAV2 viral vectors underwent efficiently replication in HEK293 cells in the presence of both pACG2 and pHelper, as expected (FIG. 4A). However, in HeLa cells, only minimal replication could be detected following overexposure of Southern blots (FIG. 4B), an observation consistent with previous studies (43). Transfection of the same amount of plasmid pdsAAV-EGFP in HEK293 (left panel) and HeLa (right panel) cells, used as an appropriate control, further corroborated these results. Thus, restoration of transgene expression from polyA-deleted rAAV2 vectors by AAV2 Rep proteins and adenoviral early proteins is independent of rAAV2 DNA replication.

Cytoplasmic Transport of polyA-Deleted, ITR-Containing mRNA Transcripts and Translation of the Encoded Proteins, in the Presence of AAV2 Rep and Adenoviral Proteins.

To explore whether ITR-containing, polyA-deleted mRNA transcripts could be translated into proteins in the cytoplasm, HEK293 cells were transduced with ssAAV2-hrGFP-AD vectors at either low MOI (L; 5,000 vgs/cell) or high MOI (H; 50,000 vgs/cell). HEK293 cells transduced with ssAAV2-hrGFP vectors at 5,000 vgs/cell (L) were used as controls. Once again, a low-level transgene expression occurred from the polyA-deleted vectors, which correlated with the MOIs (FIG. 5A). Total RNAs isolated from whole cells and nuclear and cytoplasmic fractions were quantitated for the presence of mRNA transcripts as described above. These results, shown in FIG. 5B, clearly indicated that although the total amount of mRNA expressed from ssAAV2-hrGFP-AD (H) vectors was significantly higher than from ssAAV2-hrGFP (L) vectors, and that the cytoplasmic fraction also contained higher amounts, transgene expression was significantly lower, suggesting that a majority of polyA-deleted mRNA transcripts fail to translocate to the cytoplasm, and that those transcripts in the cytoplasm are translated inefficiently. These data also indicated that cellular distribution of the mRNA will not be altered in the case of greatly increased abundance of mRNA, produced by viral infection at an extremely high M.O.I.

It was then hypothesized that the helper proteins facilitate mRNA transport to the cytoplasm. HEK293 cells were transduced with ssAAV2-hrGFP (FIG. 5C) or ssAAV2-hrGFP-AD (FIG. 5D) vectors, followed by either mock-transfection or transfection with pHelper or/and pACG2 plasmids. Total RNA isolated 24 hrs post-transduction from various fractions were subjected to reverse transcription using random primers followed by qPCR assays. As can be seen in FIG. 5C and FIG. 5D, the presence of both pACG2 and pHelper significantly enhanced mRNA transcripts levels in all cohorts, although the levels of the cytoplasmic mRNA transcripts produced from polyA-deleted vectors were approximately 2-fold lower than that produced from polyA-containing vectors in the presence of AAV2 and adenoviral proteins, correlated well with the protein expression levels. Thus, it was concluded that WT AAV2 and adenoviral proteins facilitate cytoplasmic transport of polyA-deleted mRNA transcripts as well as translation of the encoded proteins.

AAV2 Rep Binds with 3'-ITR in mRNA Transcripts.

Since pACG2 plasmid expresses both AAV2 Rep and Cap proteins, and AAV2 Rep proteins are known to interact with the ITRs in the viral DNA (8,9), the inventors reasoned that such interaction might also occur with the ITR sequence in the mRNA transcripts. To this end, the following recombinant plasmids were used (FIG. 6A): (i) pACG2; (ii) pRena1, in which the majority of cap gene sequence is deleted; (iii) pRep, in which the WT rep gene is driven by the SV40 promoter (SV40p) and the start codon of the small Rep proteins is mutated and (iv) pRep-TAP, in which a TAP tag is placed at the C-terminus of the rep open reading frame which allows immunoprecipitation of protein-mRNA complexes (10).

Figure 16E:
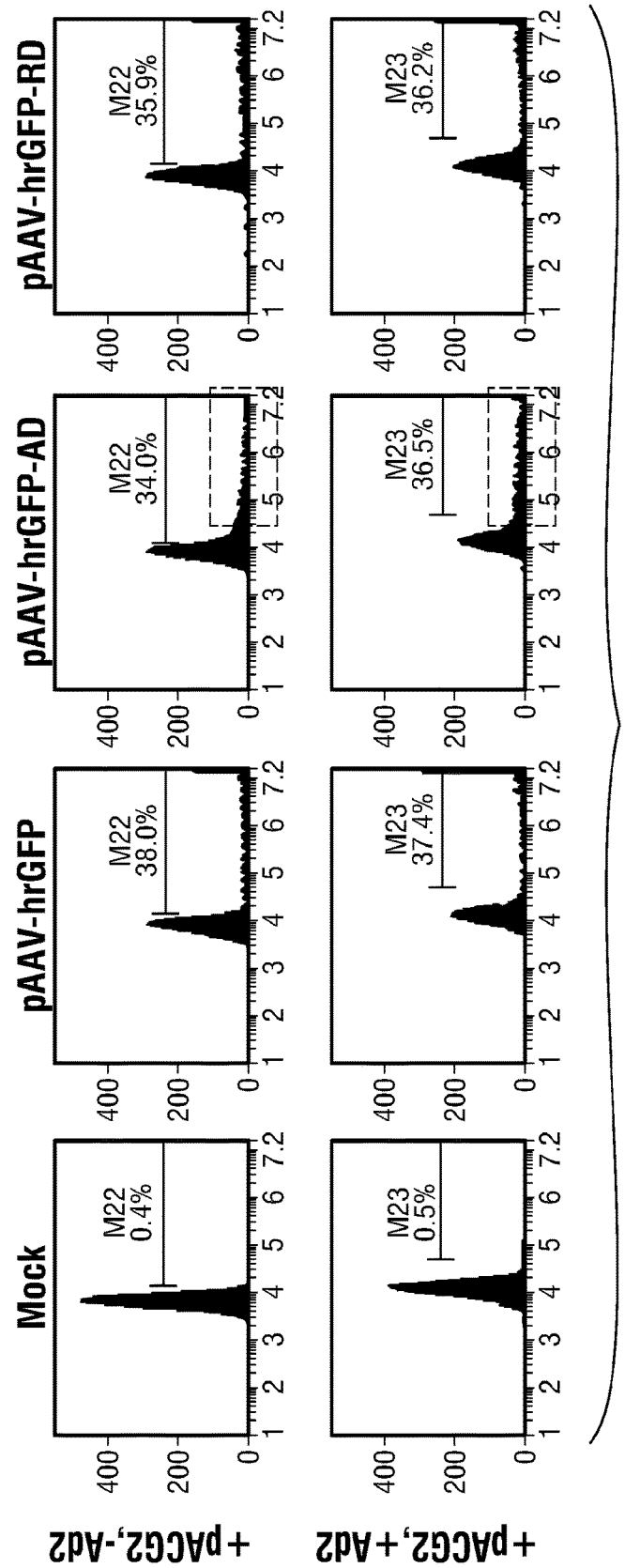
Figures 2, 18B:
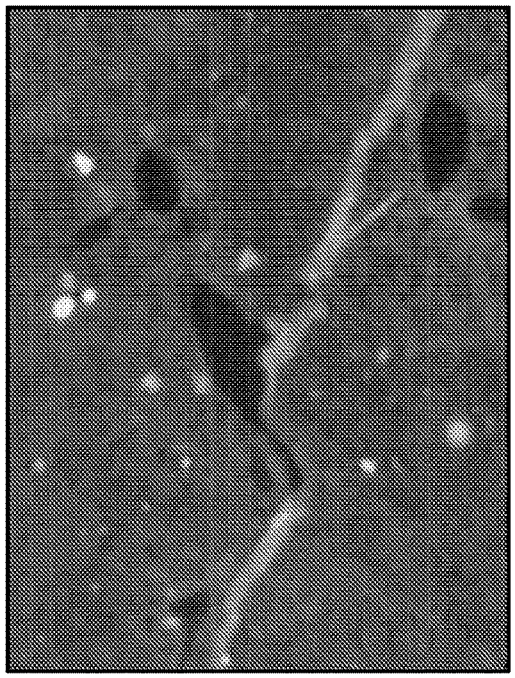
Figures 1, 18B:
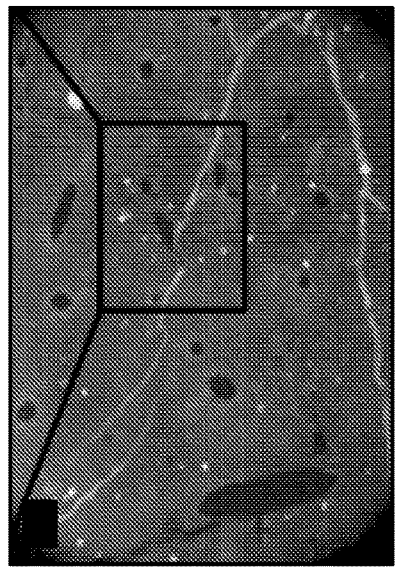
Figure 18A:
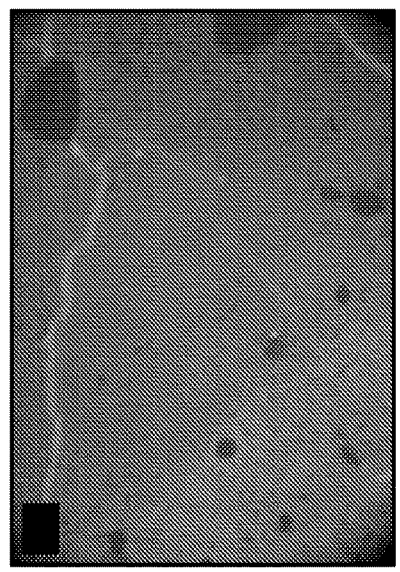

Since the increase in transgene expression from polyA-deleted vectors in the presence of pACG2+pHelper was roughly the same as that with pRena1+pHelper (FIG. 6B; FIG. 16A), it was concluded that the AAV2 Cap proteins did not play a significant role in the observed increase. However, the initial studies indicated that pRep could only partially restore transgene expression from ssAAV2-hrGFP-AD vectors (FIG. 16B and FIG. 16C). In subsequent experiments, using a range of concentration of pACG2 and pRep, it was observed that low amounts of pRep were required to restore transgene expression, since higher amounts of either pACG2 or pRep plasmids led to a significantly reduction (FIG. 6C; FIG. 16D and FIG. 16E). Western blot analyses were also performed to detect Rep proteins expression in HeLa cells, using an anti-Rep monoclonal antibody 1F, which recognizes all four Rep proteins (FIG. 6D). As can be seen, pACG2 (lane 1) or pRena1 (lane 3) expressed low levels of all four Rep proteins, and co-transfection with pHelper (lanes 2 and 4) enhanced Rep protein expression. Plasmid pRep only expressed Rep78 and Rep68, but not Rep52 and Rep40 (lane 5). However, co-transfection with pHelper (lane 7) had no effect on the SV40p-driven Rep proteins expression. In accordance with hrGFP expression data (FIG. 6C), reducing the pRep concentration to one-eighth (lane 6) resulted in educed expression of Rep78 and Rep68 proteins, level similar to those from pACG2 with pHelper (lane 2). Similar results were obtained with HEK293 cells (FIG. 16F). Thus, it was concluded that the level of large Rep proteins is essential for the increase in transgene expression from polyA-deleted vectors.

To obtain direct evidence that ITRs at the ends of the polyA-deleted mRNA transcripts interact with AAV2 Rep proteins, co-immunoprecipitation (co-IP) assays were performed, using TAP-tag method for pulling down protein-mRNA complexes (10). Such a modification did not alter the ability of Rep proteins to restore transgene expression from polyA-deleted rAAV2 vectors (FIG. 6E). The specificity of polyclonal TAP antibody was demonstrated by Western blot analyses (FIG. 16G). HEK293 cells were transfected with pACG2 (lane 1); pACG2 and pHelper (lane 2); pRep-TAP (lane 3) or pRep-TAP and pHelper (lane 4). Total proteins were extracted and subjected to Western blot analysis 48 hrs post-transfection, using either 1F antibody (left panel) or anti-TAP polyclonal antibody (right panel). These results document that TAP antibodies recognize TAP-tagged Rep proteins. The efficiency of immunoprecipitation assays was also evaluated (FIG. 6F). HEK293 cells were either mock transfected (lanes 1 and 2) or transfected with pRep-TAP and pHelper (lanes 3 and 4), and 48 hrs post-transfection, whole cell extracts were subjected to IP assays using anti-TAP antibody (lanes 2 and 4). Immunoprecipitates were electrophoresed and detected on Western blots using 1F antibody. Five percent of whole cell lysates were also electrophoresed as protein loading controls (lanes 1 and 3). Thus, it was concluded that ~20-25% of total Rep-TAP proteins could be immunoprecipitated.

HEK293 cells were then transfected with pRep-TAP and pHelper plasmids, and transduced with either ssAAV2-hrGFP or ssAAV2-hrGFP-AD vectors. Consistent with previous data, both vectors resulted in the production of similar level of mRNA transcripts 24 hrs post-transduction (FIG. 6G). Rep-TAP proteins from whole cell lysates were subsequently immunoprecipitated using anti-TAP antibody, followed by total RNA extraction from the co-immunoprecipitates. IgG was used as an appropriate control. RNA samples were then subjected to reverse transcription assays using either random primers (FIG. 6H) or oligo-d(T) primers (FIG. 6I), followed by qPCR assays using primers specific for hrGFP. As can be seen, when random primers were used, the co-immunoprecipitated mRNA transcripts generated from ssAAV2-hrGFP-AD vectors were ~4-fold higher than those from ssAAV2-hrGFP vectors, which is consistent with previous data showing that ~15% of mRNA transcripts produced by ssAAV2-hrGFP vectors contain the ITR sequences (FIG. 2B). In addition, the results using oligo-d(T) primers indicated that the co-immunoprecipitated mRNA transcripts from ssAAV2-hrGFP-AD vectors did not contain the polyA tails. Since the IgG control groups showed no differences using either random or oligo-d(T) primers, reflected the background of co-IP assays, it was thus concluded that AAV2 ITR sequences are present at the 3'-ends of mRNA transcripts produced by polyA-deleted vectors, and that these novel mRNA elements have the ability to mediate efficient cytoplasmic transport and transgene expression from polyA-deleted mRNA transcripts through the recruitment of AAV2 Rep proteins.

Substantial Protein Expression Mediated by the polyA-Deleted, ITR-Containing Transgene Cassette Independent of rAAV2 Vectors.

Figure 7A:
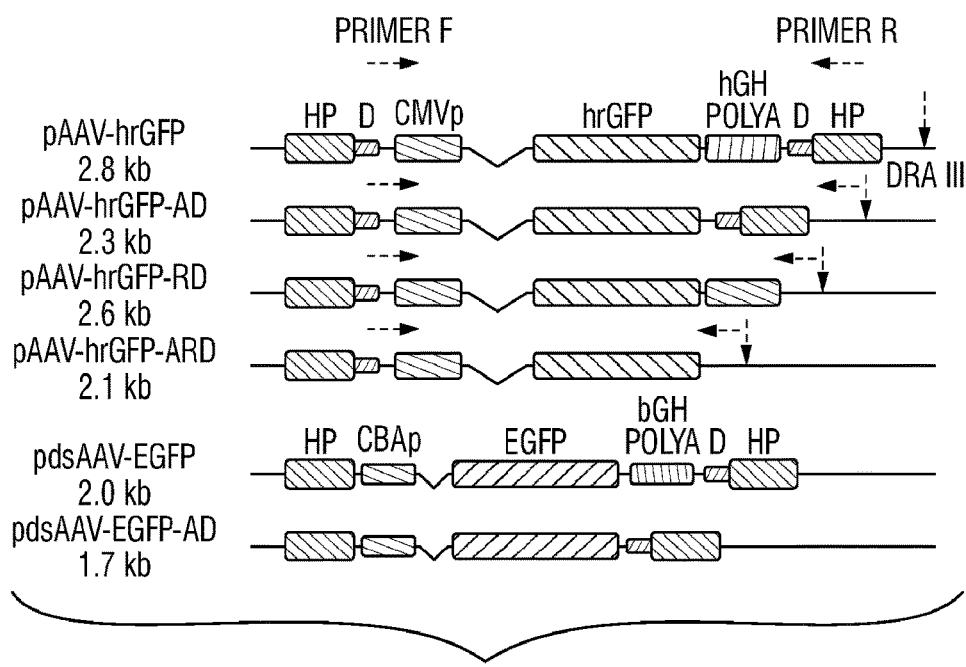
Figures 3, 7B:
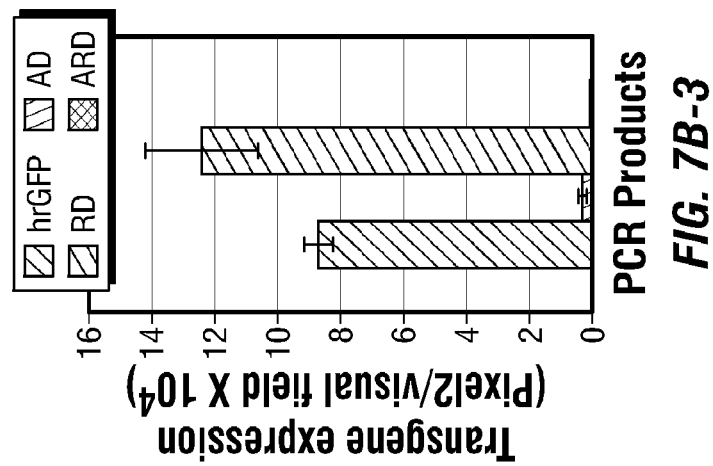
Figures 2, 7B:
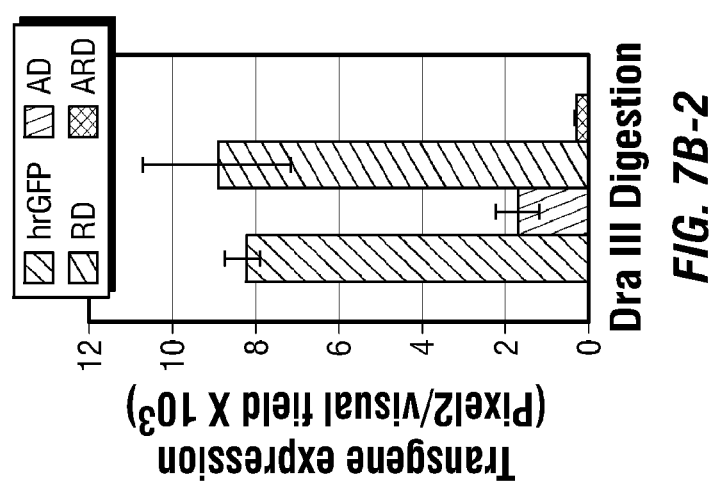
Figures 1, 7B:
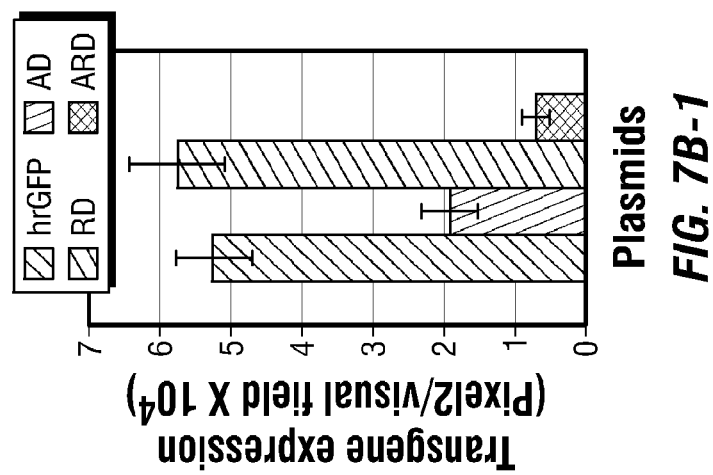

To further corroborate these results, additional experiments were performed using recombinant plasmids, instead of rAAV2 vectors. The following recombinant plasmids were generated from a commercially available plasmid pAAV-hrGFP (FIG. 7A): (i) pAAV-hrGFP-AD, in which the polyA sequence was deleted; (ii) pAAV-hrGFP-RD, in which the AAV2 right ITR was deleted; and (iii) pAAV-hrGFP-ARD, in which both polyA and the right ITR sequences were deleted. When each of these plasmids were transfected into HEK293 cells, robust transgene expression occurred from the parent plasmid (pAAV-hrGFP) as well as that from which the right ITR was deleted (pAAV-hrGFP-RD) (FIG. 7B, left panel). Surprisingly, however, detectable levels of transgene expression also occurred from the plasmids that lacked the polyA sequence (pAAV-hrGFP-AD), suggesting a minimal polyA-like function mediated by the right ITR. Similar results were obtained when the plasmids were linearized following digestion with DraIII (FIG. 7B, middle panel), or the PCR-amplified DNA products of the expression cassettes from each plasmid (FIG. 7B; right panel). Thus, it was concluded that AAV2 right ITR, in its linear, double-stranded DNA configuration, mediates detectable levels of transgene expression from a polyA-deleted cassette, at ~5-10% of that with a conventional hGH polyA sequence.

Figure 7E:
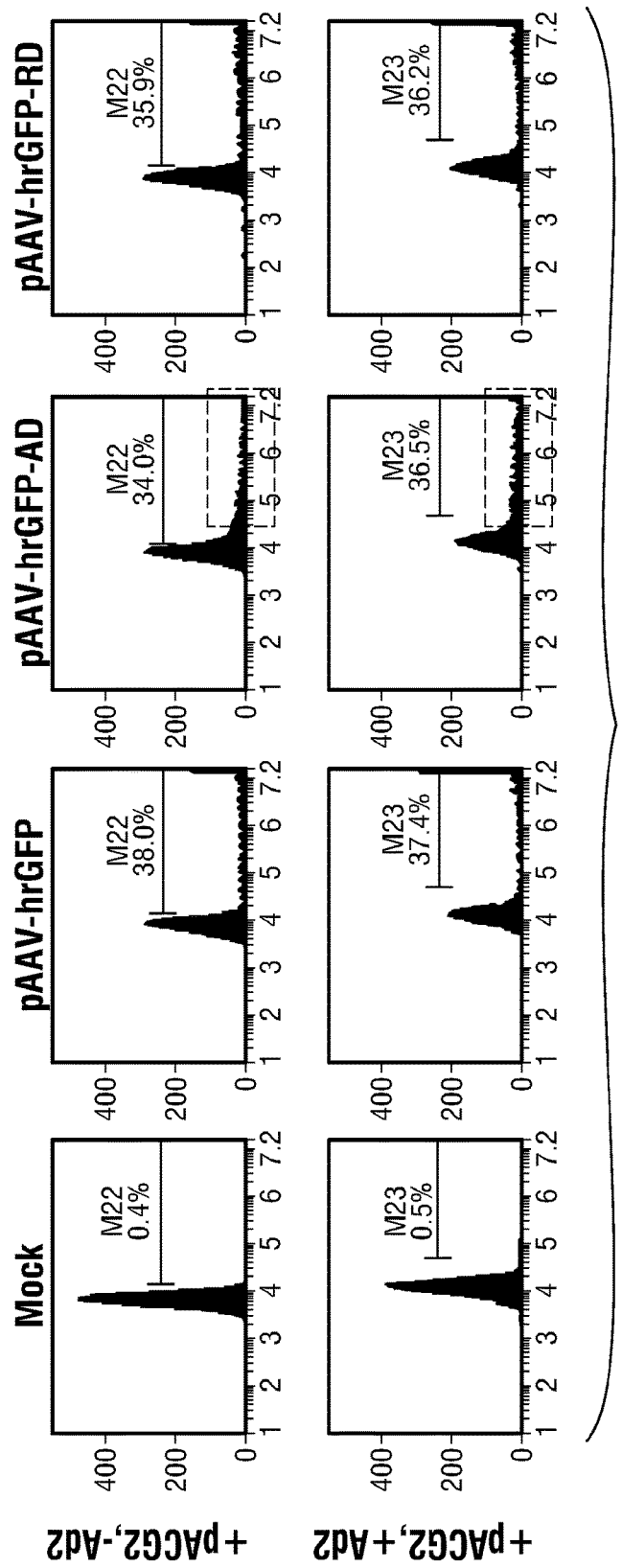

To examine whether the WT AAV2 or adenovirus early genes could facilitate transgene expression from the polyA-deleted cassettes, PCR amplicons from the three plasmids were transfected into HEK293 cells, with or without plasmids pACG2 and pHelper. The presence of adenoviral genes enhanced transgene expression from each cassette (FIG. 7C), most likely due to augmented transcription and mRNA export. Interestingly, in the presence of AAV2 rep and cap genes, the levels of transgene expression from cassettes lacking the polyA sequence, or both polyA and the ITR sequences, were approximately the same as that from the intact transgene cassette containing a conventional hGH polyA sequence (FIG. 7C). To further substantiate these results, a second polyA-deleted plasmid (pdsAAV-EGFP-AD) was generated from its parent plasmid pdsAAV-EGFP (FIG. 7A). Following transfections of these plasmids in HEK293 cells, the pACG2 and pHelper plasmid-mediated augmentation of transgene expression mediated by both AAV plasmids was readily evident (FIG. 7D). When HeLa cells were mock-transfected, or transfected with pAAV-hrGFP, pAAV-hrGFP-AD, or pAAV-hrGFP-RD plasmids, in the presence of pACG2 and co-infection with adenovirus, similar percentage of cells were GFP-positive, as determined by FACS analysis (FIG. 7E), corroborating that the presence of both WT AAV2 and adenoviral genes significantly enhances transgene expression in each individual cell.

Productive Life Cycle of the Wild-Type AAV2 in the Complete Absence of a Conventional Poly A Signal.

Figure 8A:
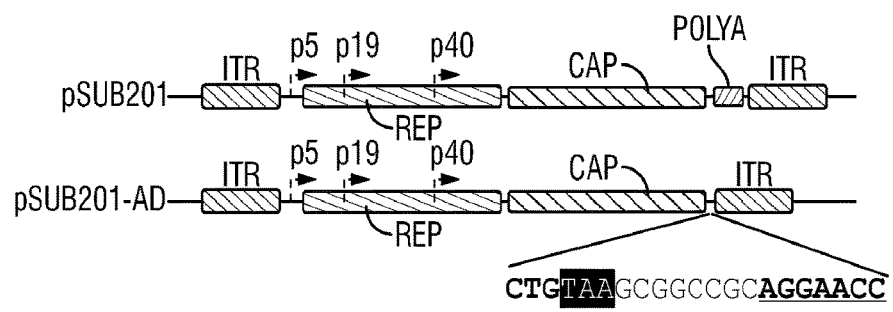
FIG. 8A, FIG. 8B, FIG. 8C, FIG. 8D, FIG. 8E, and FIG. 8F show gene expression, genome replication and progeny virus production from plasmids containing polyA-deleted WT AAV2 genome.
Figure 8B:
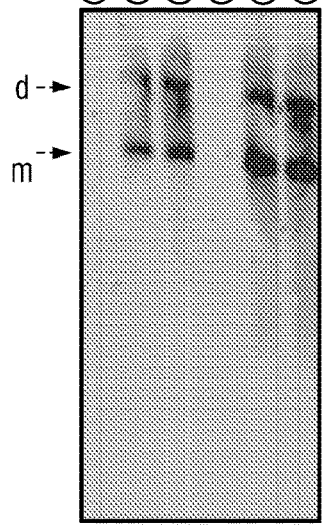
Figure 8C:
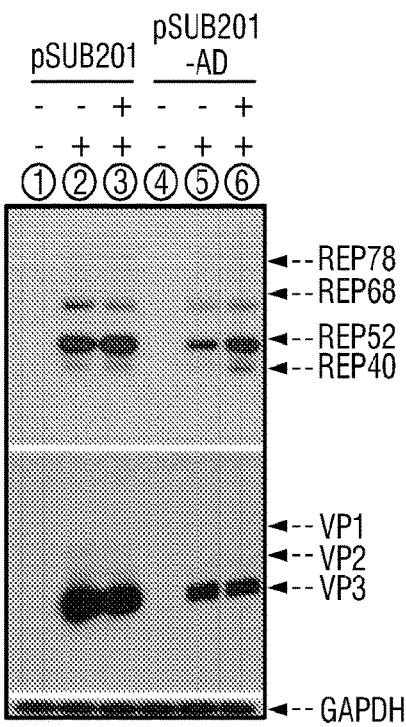

The major conclusions using rAAV2 vectors were: 1) poly A-deleted rAAV2 vectors express minimal transgene products; 2) in the presence of WT AAV2 rep and adenoviral genes, poly A-deleted rAAV2 vectors express robust transgene products. Taken together, it was hypothesized that a conventional polyA sequence is not necessary in nature rep gene-containing WT AAV2 life cycle. Upon infection, WT AAV2 lacking a polyA sequence has the ability to maintain low level of Rep and Cap proteins. In the case of co-infection with adenovirus, the minimal Rep proteins, together with adenoviral proteins, will intrigue robust WT AAV2 Rep and Cap expression. Thus, A recombinant plasmid containing the polyA-deleted WT AAV2 genome, designated pSub201-AD, was generated based on PCR strategy from the previously reported plasmid, pSub201, which contains the WT AAV2 genome (FIG. 8A), and encodes the viral Rep and Cap proteins (44). The stop codon (TAA) for the cap gene in pSub201-AD is adjacent to the right inverted terminal repeat (ITR), with a Not I restriction enzyme site in the middle (CTGTAAGCGGCCGCAGGAACC; SEQ ID NO: 10). Rescue and replication assays were performed following transfection of the two AAV2 plasmids, with pHelper and/or pACG2 in HEK293 cells. At various times post-transfections, low molecular (low-Mr) DNA samples were isolated as described previously (33), digested extensively with Dpn I, and subjected to Southern blot analysis as detailed in the Methods. As can be seen in FIG. 8B, no rescue and replication of the AAV2 genome from either plasmid occurred in the absence of helper plasmids that express the WT AAV2 rep and cap genes (pACG2), and the adenoviral E2a, E4mf6 and VA RNA genes (pHelper) (lane 1 and 4). However, in the presence of only pHelper, efficient rescue and replication of the WT AAV2 genomes occurred from both pSub201 and pSub201-AD plasmids (lanes 2, 3 and 5, 6, respectively), as evident by the accumulation of monomeric (m) and dimeric (d) forms of AAV DNA replicative intermediates. Since it is well-accepted that rescue and replication of AAV2 genome absolutely require the presence of functional AAV2 Rep proteins, and since rescue and replication of both polyA-containing (lane 2), and poly A-deleted WT AAV2 genomes (lane 5), occurred efficiently in the presence of only pHelper plasmid, these results suggest that adequate levels of the AAV2 Rep proteins are expressed from polyA-deleted pSub201-AD plasmid. This was further confirmed by Western blot analysis 48 hrs post-transfections, as shown in the upper panel in FIG. 8C. Similarly, the viral cap genes were also expressed to nearly the same levels from both pSub201 and pSub201-AD plasmids, in the presence of pHelper (lower panel in FIG. 8C).

Figure 8D:
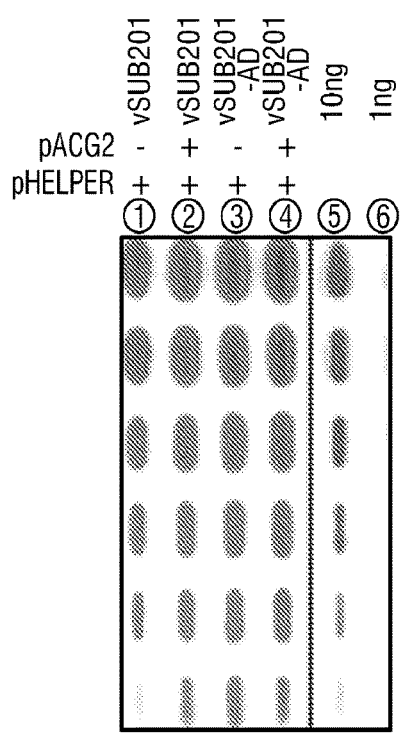
Figure 8E:
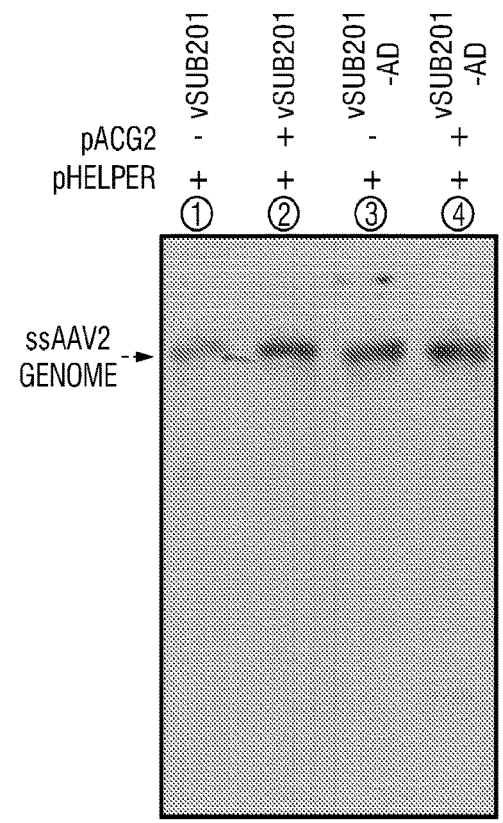
Figure 8F:
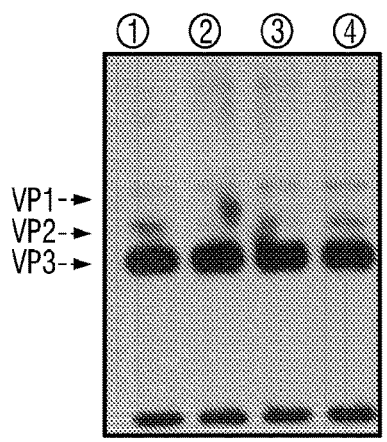

The inventors next examined whether polyA-deleted WT AAV2 genomes could undergo successful encapsidation into viral capsids, which are expressed from the same genome. To this end, a standard double- or triple-plasmid transfection protocol was used to generate AAV progeny virions (34). Following digestion with Benzonase to degrade any unencapsidated DNA, equivalent amounts of virus stocks were deproteinized to release the rAAV genomes and two-fold serial dilutions were analyzed on quantitative DNA slot blots using a $^{32}$P-labeled DNA probe as described previously (45). These results, shown in FIG. 8D, demonstrate that the presence of pHelper plasmid is necessary and sufficient for efficient packaging of the polyA-deleted WT AAV2 genomes. Analysis of purified DNA from both viral stocks on alkaline-agarose gels, followed by Southern blots assay (35) revealed similar levels of the ~4.5 kb viral genomes (FIG. 8E), as well as the viral capsid proteins on SDS-polyacrylamide gels, followed by Western blot analysis, revealing the expected 1:1:10 ratio of VP1:VP2:VP3 proteins (FIG. 8F).

To address the possibility that rescue and replication of the AAV2 genomes from recombinant plasmids might not truly reflect a natural course of infection, viral DNA replication and protein expression assays were performed using viral stocks generated from plasmids pSub201 and pSub201-AD, respectively. HEK293 cells were infected at 37° C. for 2 hrs with each virus stock, with and without co-transfection with plasmids pACG2 and/or pHelper plasmids, and low-M$_r$ DNA samples isolated 72 hrs post-infections were analyzed on Southern blots as described above. These results, shown in FIG. 9A, demonstrate that both virus stocks were biologically active, as evident by the accumulation of the characteristic m and d replicative DNA intermediates, but only in the presence of the helper-plasmids (lanes 2, 3 and 5, 6, respectively), further corroborating that pHelper plasmid alone is necessary and sufficient for efficient replication of polyA-deleted AAV2. The kinetics and the extent of AAV2 genome replication from both viruses were nearly the same, as determined by time-dependent accumulation of the AAV DNA replicative intermediates (FIG. 9B). Furthermore, Western blot analyses revealed that similar levels of both viral rep and cap genes were also expressed from both virus stocks (FIG. 9C).

Since adenovirus, and not pHelper plasmid, is the natural helper for WT AAV2, to mimic a natural infection, viral DNA replication and gene expression assays were also performed using both AAV2 viral stocks in the absence or presence of co-infection with WT adenovirus serotype 2 (Ad2). As can be seen in FIG. 9D, whereas no replication occurred in the absence of co-infection with Ad2 (lanes 1 and 4), at a multiplicity-of-infection (M.O.I) of as low as 0.5, was sufficient for efficient replication of AAV DNA (lanes 2 and 5). The levels of AAV2 Rep protein expression were also similar (FIG. 9E, lanes 2 and 5), although a relatively higher M.O.I of Ad2 co-infection was required for the Cap protein expression (FIG. 9E, lane 6). These results, nonetheless, corroborate that in the presence of Ad2, the polyA-deleted AAV2 is capable of expressing both viral gene products, undergo successful DNA replication, and produce progeny virions. Following secondary infections, the progeny virions are generated at similar levels, as determined by quantitative DNA slot-blots (FIG. 9F), and are indistinguishable from their WT counterparts with reference to their genomes, as determined by Southern blots (FIG. 9G), and to their capsid proteins, as determined by Western blots (FIG. 9H).

DISCUSSION

Figure 10C:
Figure 10D:
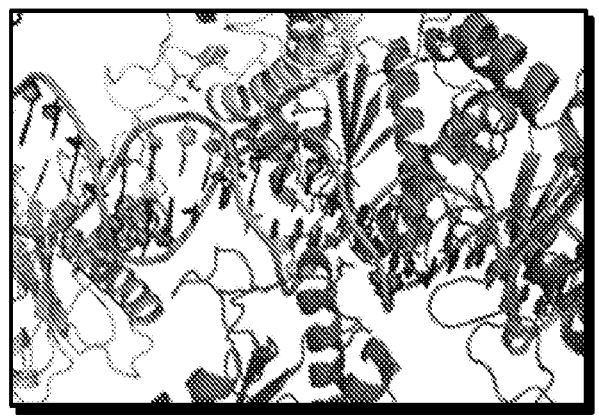

The formation of the double-stranded RNA structure at the 3'-end untranslated region (UTR) of a messenger RNA, for example, by the binding of microRNA, can halt the protein translation from this mRNA. Here, a novel method has been developed for introducing an RNA element into the 3'-UTR of a polyA-deleted mRNA and this mRNA element has the ability to form a hairpin, double-stranded RNA structure independent of other non-coding RNAs, such as microRNA, siRNA, etc. The inventors propose a model, which is shown in FIG. 1, for the function of this novel mRNA element. Double-stranded rAAV2 genomes, following second-stranded DNA synthesis, transcribe mRNAs containing polyA tails. Such mRNAs are exported into the cytoplasm efficiently and lead to robust transgene expression. When the polyA signal is deleted from rAAV2 genomes, all mRNA transcripts are terminated with ITR sequences. It is reasonable to propose that the ITR sequences in mRNA transcripts are folded into T-shaped hairpin double-stranded RNA structures, similar to the ITR as a DNA element. Indeed, computational prediction of the mRNA structure of the 3'-ITR, depicted in FIG. 10, suggests a similar secondary structure prediction whether folding either ITR-RNA or ITR-DNA (e.g., SEQ ID NOs: 11 and 12, found respectively in FIG. 10A and FIG. 10B). A model of the N-terminal 193 amino acids of AAV2 Rep78 with either the ITR-RNA or ITR-DNA sequence is depicted in FIG. 10C and FIG. 10D. Experimental data also clearly demonstrated that without the help of AAV2 Rep proteins, the polyA-deleted, ITR-containing transcripts are stably expressed but exported inefficiently out of the nucleus and those in the cytoplasm lead to minimal levels of translation into proteins. However, the terminal ITR sequences interact with AAV2 large Rep proteins, which in turn, mediate efficient translocation of mRNA transcripts devoid of a conventional polyA tail into cytoplasm where abundant protein translation ensues. Thus, through the introduction of a novel hairpin RNA element at the 3'-UTR of an mRNA, the translation of protein products can be precisely regulated.

The double membrane of the nuclear envelope in eukaryotes protects the genetic DNA information. The mRNA transcripts are transported into the cytoplasm as a messenger ribonucleoprotein (mRNP) complex. Such export is thought to occur through nuclear pore complexes (NPCs) (49). A recent report (50) suggested an alternative route for mRNA to exit the nucleus, by membrane budding, which is similar to the mechanism utilized by herpesviruses to export assembled viral capsids from the nucleus (51,52). The use of recently developed single-molecule imaging techniques (53, 54), which allow the visualization and characterization of these non-canonical mRNPs, might be useful in addressing this question. Furthermore, it was reported that solitary long terminal repeat (sLTR) of human endogenous retrovirus 9, which is embedded within introns in the human genome, might be expressed as non-coding (nc) transcripts and such ~200 bp ncRNAs may function as decoy targets to bind with cellular proteins, such as NF-Y (55).

Regardless of the underlying molecular mechanism of transcription, transport and translation of mRNA transcripts generated from polyA-deleted, replication-incompetent recombinant AAV2 vectors, in which both the viral rep and cap genes are deleted, it is noteworthy that these studies using rAAV2 vectors and WT AAV2 virus corroborate each other. Although WT AAV2 genome has an additional 5'-AATAAA-3' sequence within the rep encoding region, this sequence is not responsible for the expression of capsid proteins from polyA-deleted virus. Theoretically, post-infection, AAV needs strategies to reduce its protein expression at a minimal level until co-infection with helper viruses. Otherwise, it might be eliminated by the host immune system before massive replication. Two well-known strategies have been acknowledged in the past 30 years, one of which is the nature of single-stranded DNA genome. Conversion from the single- to the double-stranded form, either through the second-strand DNA synthesis (56,57), or through the annealing of single-stranded molecules with opposing polarities (58), is significantly enhanced in the presence of adenovirus. The other strategy is the use of weak, but inducible, promoters that ensures robust promoter activity only in the presence of helper virus.

REFERENCES

The following references, to the extent that they provide exemplary procedural or other details supplementary to those set forth herein, are specifically incorporated herein in their entirety by express reference thereto:

1. Hoggan, M D et al., Studies of small DNA viruses found in various adenovirus preparations: physical, biological, and immunological characteristics. *Proc. Natl. Acad. Sci. USA*, 55:1467-74 (1966).
2. Kotin, R M et al., Site-specific integration by adeno-associated virus. *Proc. Natl. Acad. Sci. USA*, 87:2211-5 (1990).
3. Samulski, R J et al., Targeted integration of adeno-associated virus (AAV) into human chromosome 19. *EMBO J.*, 10:3941-50 (1991).
4. Srivastava, A et al., Nucleotide sequence and organization of the adeno-associated virus 2 genome. *J. Virol.*, 45:555-64 (1983).
5. McLaughlin, S K et al., Adeno-associated virus general transduction vectors: analysis of proviral structures. *J. Virol.*, 62:1963-73 (1988).
6. Nonnenmacher, M and Weber, T. Intracellular transport of recombinant adeno-associated virus vectors. *Gene Ther.* 19:649-658 (2012)
7. Flotte, T R and K I Berns. Adeno-associated virus: a ubiquitous commensal of mammals. *Hum. Gene Ther.*, 16:401-7 (2005).
8. Ashktorab, H and A. Srivastava. Identification of nuclear proteins that specifically interact with adeno-associated virus type 2 inverted terminal repeat hairpin DNA. *J. Virol.*, 63:3034-9 (1989).
9. Im, D S and N. Muzyczka. Factors that bind to adeno-associated virus terminal repeats. *J. Virol.*, 63:3095-104 (1989).
10. Nash, K et al., Identification of cellular proteins that interact with the adeno-associated virus rep protein. *J. Virol.*, 83:454-69 (2009).
11. Qing, K et al., Adeno-associated virus type 2-mediated gene transfer: role of cellular FKBP52 protein in transgene expression. *J. Virol.*, 75:8968-76 (2001).
12. Mah, C K et al., Adeno-associated virus type 2-mediated gene transfer: role of epidermal growth factor receptor protein tyrosine kinase in transgene expression. *J. Virol.*, 72:9835-43 (1998).

13. Qing, K et al., Role of tyrosine phosphorylation of a cellular protein in adeno-associated virus 2-mediated transgene expression. *Proc. Natl. Acad. Sci. USA*, 94:10879-84 (1997).
14. Qing, K et al., Adeno-associated virus type 2-mediated gene transfer: correlation of tyrosine phosphorylation of the cellular single-stranded D sequence-binding protein with transgene expression in human cells in vitro and murine tissues in vivo. *J. Virol.*, 72:1593-9 (1998).
15. Cool, D et al., cDNA isolated from a human T-cell library encodes a member of the protein-tyrosine-phosphatase family. *Proc. Natl. Acad. Sci. USA*, 86:5257-61 (1989).
16. Mosinger, B et al., Cloning and characterization of a mouse cDNA encoding a cytoplasmic protein-tyrosine-phosphatase. *Proc. Natl. Acad. Sci. USA*, 89:499-503 (1992).
17. Qing, K et al., Adeno-associated virus type 2-mediated gene transfer: role of cellular T-cell protein tyrosine phosphatase in transgene expression in established cell lines in vitro and transgenic mice in vivo. *J. Virol.*, 77:2741-6 (2003).
18. Zhong, L et al., Self-complementary adeno-associated virus 2 (AAV)-T cell protein tyrosine phosphatase vectors as helper viruses to improve transduction efficiency of conventional single-stranded AAV vectors in vitro and in vivo. *Mol. Ther.*, 10:950-7 (2004).
19. Zhao, W et al., AAV-mediated gene transfer: Identification of a cellular protein serine/threonine phosphatase involved in augmenting vector transduction efficiency. *Mol. Ther.*, 13:S1-S2 (2006).
20. Jayandharan, G et al., Strategies for improving the transduction efficiency of single-stranded adeno-associated virus vectors in vitro and in vivo. *Gene Ther.*, 15:1287-93 (2008).
21. Jayandharan, G R et al., Optimized adeno-associated virus (AAV)-protein phosphatase-5 helper viruses for efficient liver transduction by single-stranded AAV vectors: therapeutic expression of factor IX at reduced vector doses. *Hum. Gene Ther.*, 21:271-83 (2010).
22. Ma, W et al., A simple method to increase the transduction efficiency of single-stranded adeno-associated virus vectors in vitro and in vivo. *Hum. Gene Ther.*, 22:633-40 (2012).
23. Lebkowski, J S et al., Adeno-associated virus: a vector system for efficient introduction and integration of DNA into a variety of mammalian cell types. *Mol. Cell Biol.*, 8:3988-96 (1998).
24. Mingozzi, F and K A High. Therapeutic in vivo gene transfer for genetic disease using AAV: progress and challenges. *Nat. Rev. Genet.*, 12:341-55 (2011).
25. Bainbridge, J W et al., Effect of gene therapy on visual function in Leber's congenital amaurosis. *N. Engl. J. Med.*, 358:2231-9 (2008).
26. Maguire, A M et al., Safety and efficacy of gene transfer for Leber's congenital amaurosis. *N. Engl. J. Med.*, 358: 2240-8 (2008).
27. Cideciyan, A V et al., Human gene therapy for RPE65 isomerase deficiency activates the retinoid cycle of vision but with slow rod kinetics. *Proc. Natl. Acad. Sci. USA*, 105:15112-7 (2008).
28. Nathwani, A C et al., Adenovirus-associated virus vector-mediated gene transfer in hemophilia B. *N. Engl. J. Med.*, 365:2357-65 (2011).
29. Hwu, W L et al., Gene therapy for aromatic L-amino acid decarboxylase deficiency. *Sci. Transl. Med.*, 4:134ra61 (2012).
30. Flotte, T R et al., Expression of the cystic fibrosis transmembrane conductance regulator from a novel adeno-associated virus promoter. *J. Biol. Chem.*, 268: 3781-90 (1993).
31. Haberman, R P et al., Novel transcriptional regulatory signals in the adeno-associated virus terminal repeat A/D junction element. *J. Virol.*, 74:8732-9 (2000).
32. Laughlin, C A et al., Spliced adenovirus-associated virus RNA. *Proc. Natl. Acad. Sci. USA*, 76:5567-71 (1979).
33. Wu, J et al., Self-complementary recombinant adeno-associated viral vectors: packaging capacity and the role of rep proteins in vector purity. *Hum. Gene Ther.* 18:171-82 (2007).
34. Ling, C et al., High-efficiency transduction of liver cancer cells by recombinant adeno-associated virus serotype 3 vectors. *J. Vis. Exp.*, 22(49):P12538 (2011).
35. Wang, Y et al., Limitations of encapsidation of recombinant self-complementary adeno-associated viral genomes in different serotype capsids and their quantitation. *Hum. Gene Ther. Methods*, 23:225-33 (2012).
36. Zhong, L et al., Next generation of adeno-associated virus 2 vectors: point mutations in tyrosines lead to high-efficiency transduction at lower doses. *Proc. Natl. Acad. Sci. USA*, 105:7827-32 (2008).
37. Cheng, B et al., Development of optimized AAV3 serotype vectors: mechanism of high-efficiency transduction of human liver cancer cells. *Gene Ther.*, 19:375-84 (2012).
38. Zuker, M., Mfold web server for nucleic acid folding and hybridization prediction. *Nucl. Acids Res.*, 31:3406-15 (2003).
39. Arnold, K et al., The SWISS-MODEL workspace: a web-based environment for protein structure homology modelling. *Bioinformatics*, 22:195-201 (2006).
40. Hickman, A B et al., The nuclease domain of adeno-associated virus rep coordinates replication initiation using two distinct DNA recognition interfaces. *Mol. Cell*, 13:403-14 (2004).
41. Emsley, P et al., Features and development of Coot. *Acta. Crystallogr. D Biol. Crystallogr.*, 66:486-501 (2010).
42. Ding, W et al., rAAV2 traffics through both the late and the recycling endosomes in a dose-dependent fashion. *Mol. Ther.*, 13:671-82 (2006).
43. Ni, T H et al., Cellular proteins required for adeno-associated virus DNA replication in the absence of adenovirus coinfection. *J. Virol.*, 72:2777-87 (1998).
44. Samulski, R J et al., A recombinant plasmid from which an infectious adeno-associated virus genome can be excised in vitro and its use to study viral replication. *J. Virol.*, 61:3096-101 (1987).
45. Ma, W et al., A simple method to increase the transduction efficiency of single-stranded adeno-associated virus vectors in vitro and in vivo. *Hum. Gene Ther.*, 22:633-40 (2011).
46. Flotte, T R et al., Gene expression from adeno-associated virus vectors in airway epithelial cells. *Am. J. Respir. Cell Mol. Biol.*, 7:349-56 (1992).
47. Verdin, E and C VanLint. Internal transcriptional regulatory elements in HIV-1 and other retroviruses. *Cell Mol. Biol., (Noisy-le-grand)* 41:365-9 (1995).
48. Shi, Q et al., Modulation of the specificity and activity of a cellular promoter in an adenoviral vector. *Hum. Gene Ther.*, 8:403-10 (1997).
49. Aitchison, J D and M P Rout. The yeast nuclear pore complex and transport through it. *Genetics*, 190:855-83 (2012).

50. Speese, S D et al., Nuclear envelope budding enables large ribonucleoprotein particle export during synaptic Wnt signaling. *Cell*, 149:832-46 (2012).
51. Muranyi, W et al., Cytomegalovirus recruitment of cellular kinases to dissolve the nuclear lamina. *Science*, 297:854-7 (2002).
52. Mettenleiter, T C et al., Herpesvirus assembly: a tale of two membranes. *Curr. Opin. Microbiol.*, 9:423-9 (2006).
53. Mor, A et al., Dynamics of single mRNP nucleocytoplasmic transport and export through the nuclear pore in living cells. *Nat. Cell Biol.*, 12:543-52 (2010).
54. Grunwald, D et al., Nuclear export dynamics of RNA-protein complexes. *Nature*, 475:333-41 (2011).
55. Xu, L A et al., A Novel Function of RNAs Arising From the LTR of Human Endogenous Retrovirus-9 in Cell Cycle Arrest. *J. Virol.*, 87(1):25-36 (2013).
56. Fisher, K J et al., Transduction with recombinant adeno-associated virus for gene therapy is limited by leading-strand synthesis. *J. Virol.*, 70:520-32 (1996).
57. Ferrari, F K et al., Second-strand synthesis is a rate-limiting step for efficient transduction by recombinant adeno-associated virus vectors. *J. Virol.*, 70:3227-34 (1996).
58. Nakai, H et al., Recruitment of single-stranded recombinant adeno-associated virus vector genomes and intermolecular recombination are responsible for stable transduction of liver in vivo. *J. Virol.*, 74:9451-63 (2000).
Pearson and Lipman, *Proc. Natl. Acad. Sci. USA*, 85(8): 2444-8 (1988).

Example 2—Productive Life Cycle of AAV2 in the Complete Absence of a Conventional Polyadenylation Signal Polyadenylation is the addition of a tail of multiple adenosine monophosphates to the 3'-ends of mRNA molecules, which is important for the nuclear export, translation, and stability of mRNA[1]. With the exception of histone mRNAs, all eukaryotic mRNAs, are polyadenylated[2], and all eukaryotic genes, including viral genomes, contain a polyA signal (5'-AATAAA-3'; SEQ ID NO:13) at the end of their DNA sequences to process the addition of a polyA tail during transcription. The core histone (H2A, H2B, H3 and H4) mRNAs instead contain a 3' stem-loop structure followed by a purine-rich sequence, termed histone downstream element, and a distinct set of cellular factors facilitate the nuclear export of these mRNAs[3]. A non-pathogenic human parvovirus, the adeno-associated virus 2 (AAV2), contains a single-stranded DNA genome, which is transcriptionally-inactive, is flanked by inverted terminal repeats (ITRs) that form T-shaped hairpin structures[4], and requires co-infection with a helper-virus for a productive infection. The present example provides evidence that a conventional polyA signal is dispensable for AAV2, and it can be substituted by the viral ITR to mediate efficient viral gene expression. Furthermore, AAV2 genomes devoid of a conventional polyA signal, undergo gene expression, complete genome replication, encapsidation, and progeny virion production. Although it remains to be seen whether polyA-deleted AAVs exist in nature, the results identify the first eukaryotic organism that can maintain its life cycle without polyadenylation. In the absence of a helper-virus, it appears that the dispensable nature of a polyA signal is yet another mechanism by which AAV2 limits viral gene expression.

Adeno-associated virus (AAV) was first discovered as a contaminant of adenovirus stocks in the 1960s[5]. The most extensively studied serotype of AAV is type 2 (AAV2), which serves as a prototype for the AAV family. The AAV2 genome is a single-stranded DNA of approximately 4.7 kb[4]. The viral genome is flanked by inverted terminal repeats (ITRs) that form T-shaped, base-paired hairpin structures, and contain cis-elements required for viral genome replication, encapsidation[6], integration into as well as rescue from host chromosomal DNA[7]. As illustrated in FIG. 26A, the left open reading frame, rep, encodes four nonstructural proteins required for replication (Rep78, Rep68, Rep52, and Rep40), whereas the right open reading frame, cap, encodes three structural proteins that make up the viral capsid (VP1, VP2, and VP3). Three viral promoters are identified by their relative map position within the viral genome: p5, p19, and p40. Productive AAV2 infection requires helper functions that can be supplied either by co-infecting helper viruses or by DNA damaging agents. Helper viruses shown to promote AAV replication include adenovirus[8], herpes simplex virus (HSV)[9], vaccinia virus[10], cytomegalovirus[11], Epstein-Barr virus, varicella-zoster virus[12], and human papillomavirus (HPV)[13]. Previous studies have documented that all major AAV2 viral transcripts are polyadenylated[14] and subsequently, a potential 250 nucleotides polyA signal, containing the critical sequence AATAAA (SEQ ID NO: 13), was identified in AAV2 genome.

In recent studies with rAAV vectors, in which in addition to the viral rep and cap genes, the signal for polyadenylation (polyA) was deleted, detectable levels of transgene expression could still be obtained, and the extent of which could be dramatically improved in the presence of AAV2 Rep proteins. In this example, wild-type (WT) AAV was shown to also be able to maintain its productive life-cycle in the absence of polyadenylation.

Experimental Methods

Cell Lines and Cultures.

HEK293 cell line was purchased from the American Type Culture Collection, and maintained in complete DMEM media (Mediatech, Inc.) supplemented with 10% heat-inactivated fetal bovine serum (FBS, Sigma-Aldrich), 1% penicillin and streptomycin (P/S, Lonza). Cells were grown as adherent culture in a humidified atmosphere at 37° C. in 5% $CO_2$ and were sub-cultured after treatment with trypsin-versene mixture (Lonza) for 2-5 min at room temperature, washed and re-suspended in complete medium.

Plasmids.

Plasmid pSub201 was provided by Dr. Jude Samulski, University of North Carolina at Chapel Hill. The whole-gene cassette was amplified by NotI site-linked primers 201AD-F and 201AD-R, as indicated below. The amplicons were digested with NotI and $T_4$ ligase-mediated ligation with NotI-digested pAAV-hrGFP (which was purchased from Agilent Technologies), to generate pSub201-AD. Plasmid pACG2 has previously been described.[16,]. All plasmids were sequenced prior to usage.

Primers and Oligonucleotide Probes.

Primers 201AD-F (5'-CGATGCGGCCG CTGTAGT-TAATGATTA-3; SEQ ID NO:14) and 201AD-R (5'-CGAT-GCGGCCGC TTACAGATTACGAGTCA-3; SEQ ID NO:15) were used to amplify the WT AAV2 gene cassette in FIG. 26A. [32]P- or DIG-labeled oligonucleotide probes (Rep2Cap2, 405 bp) isolated from pSub201 by digestion with PstI were used for hybridization to the viral genomes in DNA slot-blot and Southern blot assays.

DNA Transfection Assays.

Cells were seeded in 6-well plates at $5 \times 10^5$ cells per well in complete DMEM and incubated at 37° C. overnight before experiments. The plasmids were incubated with linear polyethylenimine (PEI, Polysciences, Inc. Cat#23966) at 37° C. in serum-free and antibiotic-free DMEM for 10 min. The DNA-PEI mixture was then added into cell culture and incubated 37° C. for 6 hrs. Cells were then washed with complete DMEM twice and incubated at 37° C. for 48 hrs.

WT AAV2 Viruses.

Viruses were packaged using a protocol described previously[17]. Briefly, HEK293 cells were co-transfected by three plasmids in the presence of PEI to produce each of the viral stocks. Cells were harvested 72 hrs' post-transfection, subjected to three rounds of freeze-thaw, digested with benzonase and purified by iodixanol gradient ultra-centrifugation followed by ion exchange chromatography using HiTrap SP HP column. The physical particle titers of viral stocks were determined by quantitative DNA slot-blot analyses.

Viral DNA Rescue and Replication Assays.

PEI-mediated plasmid transfections were carried out as described above with equivalent amounts of each of the AAV2 plasmid, together with pHelper and/or pACG2 in HEK293 cells. At various times post-transfection, low-molecular-weight (low-$M_r$) DNA samples were isolated by the procedure described previously[16], digested extensively with DpnI, and then electrophoresed on 1.2% neutral agarose gels, followed by transfer to nylon membranes. Subsequently, the membranes were hybridized with DIG-labeled DNA probe overnight, followed by washing and expose to BIOMAX MR® X-ray film at −70° C.

Viral DNA Extraction from Purified Viral Stocks.

Equivalent amounts of viral stock were digested with benzonase at 37° C. for 1 hr in a total volume of 50 µL. An equal volume of 100 mM NaOH was added followed by incubation at 65° C. for 30 min. Viral DNA was then purified by DNA Clean & Concentrator-25® (ZYMO Research, Cat#D4034).

Southern Blot Assays.

Viral DNA was purified as stated above and electrophoresed on 1.2% neutral agarose gels, followed by transfer to nylon membranes. Briefly, the gel was stained with 1 mg/mL ethidium bromide for 20 min. The DNA was visualized by UV trans-illumination and photographed. The gel was equilibrated with solution I (0.25 M HCl) for 20 min and with solution II (1 M NaCl, 0.5 M NaOH) for 40 min at room temperature. DNA was transferred to Immobilon-NY+® membranes (Millipore, Bedford, Mass.) in 20×SSC. The membrane was pre-hybridized for 30 min at 42° C. in 25 mL hybridization solution (DIG Easy Hyb, DIG High Prime DNA Labeling and Detection Starter Kit II, Roche, Cat. No. 11585614910). Subsequently, the membranes were hybridized with denatured DIG-labeled DNA probe in total volume of 25 mL hybridization solution at 42° C. for 18-20 hrs. Membranes were then washed twice in 50 mL wash solution I (2×SSC, 0.1% SDS) at room temperature for 5 min, twice in 50 mL wash solution II (0.1×SSC, 0.1% SDS) at 68° C. for 15 min, and incubated for 30 min in 20 mL blocking solution, washed in 20 mL wash buffer for 15 min., and then equilibrated 5 min in 20 mL detection buffer. The membranes were exposed to BIOMAX MR® X-ray films (Kodak, Rochester, N.Y.) for 15 min at room temperature after being incubated in 1 mL chemiluminescent substrate for alkaline phosphatase (CSPD) for 15 min.

Western Blot Assays.

Western blot analyses were performed as described previously[22]. Briefly, cells were harvested and disrupted in a radio-immunoprecipitation assay (RIPA) lysis buffer (50 mM Tris-HCl, pH 8.0, 150 mM NaCl, 0.1% SDS, 1% NP-40, 0.25% sodium deoxycholate and 1 mM EDTA with protease inhibitor cocktail, 1 mM NaF and 1 mM $Na_3VO_4$). Total protein concentration was measured using a Bradford reagent (Bio-Rad, Hercules, Calif., USA). Following normalization for protein concentration, samples were separated using 12% SDS-PAGE electrophoresis, electro-transferred to a nitrocellulose membrane (Bio-Rad), and probed with relevant primary antibodies at 4° C. overnight. The membrane was then incubated with horseradish peroxidase-conjugated secondary antibodies (GE Healthcare, Cat#NA931, 1:5000 dilution), and detected with an enhanced chemi-luminescence substrate (MEMD Millipore, Cat#WBKLS0100). All membranes were stripped and re-probed for anti-GAPDH antibody as a loading control. Antibodies against Rep proteins (monoclonal 1F) were provided by Dr. Nicholas Muzyczka, University of Florida. Antibodies against GAPDH (polyclonal) were purchased from Thermo Scientific, Cat#PA1-988. Antibodies against TAP-tag (polyclonal) were purchased from GenScript, Cat#A00683-40. Antibodies against IκB (polyclonal, C-21) and Lamin B (polyclonal, C-20) were purchased from Santa Cruz Biotechnology.

Results

A recombinant plasmid containing the polyA-deleted AAV2 genome, designated pSub201-AD, was generated from the previously reported plasmid, pSub201, which contains the WT AAV2 genome, and encodes the viral Rep and Cap proteins[15]. The stop codon (TAA) for the cap gene in pSub201-AD is adjacent to the right inverted terminal repeat (ITR), with a NotI restriction enzyme site in the middle. Rescue and replication assays were performed following transfection of the two AAV plasmids, with pHelper and/or pACG2 in HEK293 cells. At various times post-transfection, low-molecular-weight (low-$M_r$) DNA samples were isolated as described previously[16], digested extensively with DpnI, and subjected to Southern blot analysis as detailed below. No rescue and replication of the AAV2 genome from either plasmid occurred in the absence of helper plasmids that express the WT AAV2 rep and cap genes (pACG2), and the adenoviral Eta, E4orf6 and VA RNA genes (pHelper). However, in the presence of either helper-plasmid, efficient rescue and replication of the WT AAV2 genomes occurred from both pSub201 and pSub201-AD plasmids, as evident by the accumulation of monomeric (m) and dimeric (d) forms of AAV DNA replicative intermediates. Since it is well accepted that rescue and replication of AAV2 genome absolutely require the presence of functional AAV2 Rep proteins, and since rescue and replication of both polyA-containing (lane 2), and polyA-deleted WT AAV2 genomes (lane 5), occurred efficiently in the presence of only pHelper plasmid, these results suggested that adequate levels of the AAV2 Rep proteins were expressed from polyA-deleted pSub201-AD plasmid. This was further confirmed by Western blot analysis 48 hrs' post-transfection. Similarly, the viral cap genes were also expressed to nearly the same levels from both pSub201 and pSub201-AD plasmids.

The inventors next examined whether polyA-deleted WT AAV2 genomes could undergo successful encapsidation into viral capsids, which are expressed from the same genome. To this end, a standard double- or triple-plasmid transfection protocol was used to generate AAV progeny virions[17]. Following digestion with Benzonase to degrade any unencapsidated DNA, equivalent amounts of virus stocks were deproteinized to release the rAAV genomes and two-fold serial dilutions were analyzed on quantitative DNA slot blots using a $^{32}P$-labeled DNA probe as described previously[18]. These results demonstrated that the presence of pHelper plasmid is necessary and sufficient for efficient packaging of the polyA-deleted WT AAV2 genomes. Analysis of purified DNA from both virus stocks on alkaline-agarose gels, followed by Southern blots revealed similar levels of the ~4.5 kb viral genomes, as well as the viral capsid proteins on SDS-polyacrylamide gels, followed by Western blot analysis, revealing the expected 1:1:10 ratio of VP1:VP2:VP3 proteins.

To address the possibility that rescue and replication of the AAV2 genomes from recombinant plasmids might not truly reflect a natural course of infection, viral DNA replication and protein expression assays were performed using viral stocks generated from plasmids pSub201 and pSub201-AD, respectively. HEK293 cells were infected at 37° C. for 2 hrs with each virus stock, with and without co-transfection with plasmids pACG2 and/or pHelper plasmids, and low-$M_r$ DNA samples isolated 72 hrs' post-infection were analyzed on Southern blots as described above. These results demonstrated that both virus stocks were biologically active, as evident by the accumulation of the characteristic m and d replicative DNA intermediates, but only in the presence of either of the helper-plasmids, further corroborating that pHelper plasmid alone is necessary and sufficient for efficient replication of polyA-deleted AAV2. The kinetics and the extent of AAV2 genome replication from both viruses were nearly the same, as determined by time-dependent accumulation of the AAV DNA replicative intermediates. Furthermore, Western blot analyses revealed that similar levels of both viral Rep and cap genes were also expressed from both virus stocks.

Since adenovirus, and not pHelper plasmid, is the natural helper for WT AAV2, to mimic a natural infection, viral DNA replication and gene expression assays were also performed using both AAV2 viral stocks in the absence or presence of co-infection with WT adenovirus serotype 2 (Ad2), as described above. Whereas no replication occurred in the absence of co-infection with Ad2, at a multiplicity-of-infection (MOI) of as low as 0.5, was sufficient for efficient replication of AAV DNA. The levels of AAV2 Rep protein expression were also similar although a relatively higher M.O.I of Ad2 co-infection was required for the Cap protein expression. These results, nonetheless, corroborated that in the presence of Ad2, the polyA-deleted AAV2 is capable of expressing both viral gene products, undergo successful DNA replication, and produce progeny virions. Following secondary infections, the progeny virions are generated at similar levels, as determined by quantitative DNA slot-blots, and are indistinguishable from their WT counterparts with reference to their genomes, as determined by Southern blots, and capsid proteins, as determined by Western blots.

It is evident that the polyA-deleted viral genomes are capable of expressing minimal yet detectable levels of viral gene products, the extent of which is dramatically increased in the presence of the AAV2 Rep and adenovirus proteins. Using rAAV2 vectors, it was possible to demonstrate that in the absence of a conventional polyA signal, the viral 3'-end ITR is transcribed as part of the mRNA, which interact with the AAV Rep proteins to mediate efficient transport to the cytoplasm, resulting in robust transgene expression from polyA-deleted mRNA transcripts. Similarly, Upon infection, polyA-deleted WT AAV2 has the ability to maintain a minimal level of expression of Rep proteins, and in the presence of co-infection with adenovirus, the Rep proteins interact with the 3'-ends of the polyA-less mRNA transcripts, mediate efficient transport to the cytoplasm, and lead to optimal levels of expression of viral Rep and Cap proteins. These studies demonstrated that a conventional polyA signal was dispensable for WT AAV2, and could be substituted by the viral ITR to mediate efficient viral gene expression.

The single-stranded nature of the wild-type (WT) AAV2 genome, which renders it transcriptionally-inactive, raises the intriguing possibility that AAV2 utilizes this feature to minimize expression of the viral genes during a natural infection. Previous studies have documented the 5'-ITR in the viral genome contains the binding site for a host cell protein, FKBP52, phosphorylated forms of which strongly inhibit the viral second-strand DNA synthesis, another mechanism employed by AAV2 to limit viral gene expression[19]. In more recent studies, the 3'-ATR was shown to contain binding sites for a cellular NF-κB-repression factor, a negative regulator of transcription[20]. Thus, in the absence of a helper-virus, the dispensable nature of a polyA signal is apparently another mechanism by which AAV2 limits the viral gene expression. These studies identify the first eukaryotic organism that can maintain its life cycle without polyadenylation.

REFERENCES

The following references, to the extent that they provide exemplary procedural or other details supplementary to those set forth herein, are specifically incorporated herein in their entirety by express reference thereto:

Atchison, R W, Casto, B C and Hammon, W M, "Adenovirus-associated defective virus particles," *Science*, 149: 754-756 (1965).

Battle, D J and Doudna, J A, "The stem-loop binding protein forms a highly stable and specific complex with the 3' stem-loop of histone mRNAs," *RNA*, 7:123-132 (2001).

Buller, R M, Janik, J E, Sebring, E D and Rose, J A, "Herpes simplex virus types 1 and 2 completely help adenovirus-associated virus replication," *J. Virol.*, 40:241-247 (1981).

Cao, M, Zhu, H, Bandyopadhyay, S, You, H and Hermonat, P L "HPV-16 E1, E2 and E6 each complement the Ad5 helper gene set, increasing rAAV2 and wt AAV2 production," *Gene Ther.*, 19:418-424 (2012).

Cheng, B et al., "Development of optimized AAV3 serotype vectors: mechanism of high-efficiency transduction of human liver cancer cells," *Gene Ther.*, 19:375-384, (2012).

Georg-Fries, B, Biederlack, S, Wolf, J and zur Hausen, H, "Analysis of proteins, helper dependence, and seroepidemiology of a new human parvovirus," *Virology*, 134:64-71 (1984).

Guhaniyogi, J and Brewer, G, "Regulation of mRNA stability in mammalian cells," *Gene*, 265:11-23 (2001).

Hoggan, M D, Blacklow, N R and Rowe, W P, "Studies of small DNA viruses found in various adenovirus preparations: physical, biological, and immunological characteristics," *Proc. Nat'l. Acad. Sci. USA*, 55:1467-1474 (1966).

Jayandharan, G R et al., "Activation of the NF-kappaB pathway by adeno-associated virus (AAV) vectors and its implications in immune response and gene therapy," *Proc. Nat'l. Acad. Sci. USA*, 108:3743-3748 (2011).

Laughlin, C A, Westphal, H and Carter, B J, "Spliced adenovirus-associated virus RNA," *Proc. Nat'l. Acad. Sci. USA*, 76:5567-5571 (1979).

Ling, C et al., "High-efficiency transduction of liver cancer cells by recombinant adeno-associated virus serotype 3 vectors," *J. Visual. Exp.*, 22(49):2538 (2011).

Marzluff, W F, Wagner, E J and Duronio, R J, "Metabolism and regulation of canonical histone mRNAs: life without a poly(A) tail," *Nat. Rev. Genet.*, 9:843-854, (2008).

McLaughlin, S K, Collis, P, Hermonat, P L and Muzyczka, N, "Adeno-associated virus general transduction vectors: analysis of proviral structures," *J. Virol.*, 62:1963-1973 (1988).

McPherson, R A, Rosenthal, L J and Rose, J A, "Human cytomegalovirus completely helps adeno-associated virus replication," *Virology*, 147:217-222 (1985).

Qing, K. et al., "Adeno-associated virus type 2-mediated gene transfer: role of cellular FKBP52 protein in transgene expression," *J. Virol.*, 75:8968-8976 (2001).

Samulski, R J, Chang, L S and Shenk, T, "A recombinant plasmid from which an infectious adeno-associated virus genome can be excised in vitro and its use to study viral replication," *J. Virol.*, 61:3096-3101 (1987).

Schlehofer, J R, Ehrbar, M and zur Hausen, H, "Vaccinia virus, herpes simplex virus, and carcinogens induce DNA amplification in a human cell line and support replication of a helpervirus dependent parvovirus," *Virology*, 152: 110-117 (1986).

Srivastava, A., Lusby, E W and Berns, K I, "Nucleotide sequence and organization of the adeno-associated virus 2 genome," *J. Virol.*, 45:555-564 (1983).

Wang, Y et al., "Limitations of encapsidation of recombinant self-complementary adeno-associated viral genomes in different serotype capsids and their quantitation," *Hum. Gene Ther. Meth.*, 23:225-233 (2012).

Wu, J et al., "Self-complementary recombinant adeno-associated viral vectors: packaging capacity and the role of rep proteins in vector purity," *Hum. Gene Ther.*, 18(2):171-82 (2007).

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A recombinant adeno-associated viral (rAAV) vector comprising at least a first expression cassette that comprises a promoter operably linked to at least a first nucleic acid segment that encodes at least a first mammalian polypeptide, wherein the first expression cassette lacks a polyA signal sequence, and wherein the mRNA produced from the vector lacks a polyA sequence at its 3'-end, but includes an inverted terminal repeat (ITR) at its 3'-end.

2. The rAAV vector of claim 1, wherein the 3'-end of the mRNA further comprises a stable RNA element capable of forming a stable, hairpin, double-stranded RNA structure that regulates transcription of the mRNA, its translocation across a mammalian cell membrane, its translation into mature polypeptide, or a combination thereof.

3. A composition comprising the rAAV vector of claim 2, wherein-the composition also comprises one or more endogenous or exogenously-provided cellular proteins, regulatory elements, siRNAs, helper plasmids, or any combination thereof, wherein the cellular proteins mediate the regulation of translation of the mRNA produced from the vector.

4. A composition comprising the rAAV vector of claim 3, wherein the composition further comprises one or more endogenous or exogenously-provided cellular proteins, regulatory elements, siRNAs, helper plasmids, or any combination thereof that regulate translocation of the vector across a mammalian cell membrane.

5. A composition comprising the rAAV vector of claim 3, wherein the one or more endogenous or exogenously-provided cellular proteins is Rep78/68.

6. The rAAV vector of claim 1, further comprising a reporter gene, such as that encoding GFP.

7. A composition comprising the rAAV vector of claim 1, wherein the composition comprises a helper plasmid that encodes one or more cellular or viral proteins, or a combination thereof that regulates expression of at least a first encoded mammalian polypeptide.

8. The rAAV vector of claim 1, wherein the promoter is an inducible promoter.

9. The rAAV vector of claim 1, wherein the vector is a self-complementary rAAV (scAAV).

10. The rAAV vector according to claim 1, further comprising at least a first enhancer operably linked to the at least a first nucleic segment.

11. The rAAV vector according to claim 1, further comprising at least a first mammalian intron sequence operably linked to the at least a first nucleic segment.

12. The rAAV vector according to claim 1, wherein the at least a first mammalian polypeptide is of human, non-human primate, murine, feline, canine, porcine, ovine, bovine, equine, epine, caprine, or lupine origin.

13. The rAAV vector according to claim 1, wherein the at least a first nucleic acid segment encodes a biologically-active human polypeptide.

14. The rAAV vector according to claim 1, comprised within an infectious adeno-associated viral particle, virion, or a plurality of infectious AAV particles.

15. The recombinant adeno-associated viral (rAAV) vector of claim 1, wherein a detectable level of transgene expression is observed from the vector.

16. The recombinant adeno-associated viral (rAAV) vector of claim 1, wherein the vector undergoes complete gene expression, genome replication, encapsidation and progeny virion production.

17. A virion or an infectious viral particle comprising the rAAV vector in accordance with claim 1.

18. The virion or an infectious viral particle of claim 17, wherein the virion or infectious viral particle is a recombinant adeno-associated virus serotype 1 (rAAV1), a recombinant adeno-associated virus serotype 2 (rAAV2), recombinant adeno-associated virus serotype 3 (rAAV3), a recombinant adeno-associated virus serotype 4 (rAAV4), a recombinant adeno-associated virus serotype 5 (rAAV5), a recombinant adeno-associated virus serotype 6 (rAAV6), a recombinant adeno-associated virus serotype 7 (rAAV7), a recombinant adeno-associated virus serotype 8 (rAAV8), a recombinant adeno-associated virus serotype 9 (rAAV9), a recombinant adeno-associated virus serotype 10 (rAAV10), a recombinant adeno-associated virus serotype 11 (rAAV11), or a recombinant adeno-associated virus serotype 12 (rAAV12).

19. An isolated mammalian host cell comprising:
(a) the rAAV vector in accordance with claim 1;
(b) a virion or infectious viral particle comprising the rAAV vector in accordance with (a); or
(c) a plurality of infectious viral particles prepared from the rAAV vector in accordance with (a).

20. The isolated mammalian host cell according to claim 19, wherein the cell is a human host cell.

21. A composition comprising:
(1) (a) the rAAV vector in accordance with claim 1;
(b) a virion or infectious viral particle comprising the rAAV vector in accordance with (a); or
(c) a plurality of infectious viral particles prepared from the rAAV vector in accordance with (a); and
(2) a pharmaceutically-acceptable buffer, carrier, vehicle, or diluent.

22. The composition according to claim 21, further comprising a lipid, a liposome, a lipid complex, an ethosome, a niosome, a nanoparticle, a microparticle, a liposphere, a nanocapsule, or any combination thereof.

23. A kit comprising:
(1) a component selected from the group consisting of:
(a) the rAAV vector in accordance with claim 1;
(b) a virion or infectious viral particle comprising the rAAV vector in accordance with (a); or
(c) a plurality of infectious viral particles prepared from the rAAV vector in accordance with (a); and
(2) instructions for using the component in the diagnosis, prevention, treatment, or amelioration of one or more symptoms of a dystrophy, disease, disorder, abnormal condition, or a protein deficiency in a human.

* * * * *